(12) United States Patent
Kleiner et al.

(10) Patent No.: US 11,911,293 B2
(45) Date of Patent: Feb. 27, 2024

(54) TOOLS FOR SPINAL SURGERY

(71) Applicant: Spinal Surgical Strategies, Inc., Incline Village, NV (US)

(72) Inventors: Jeffrey B. Kleiner, Denver, CO (US); Michael J. Milella, Incline Village, NV (US); Edward J. Grimberg, Jr., Golden, CO (US)

(73) Assignee: SPINAL SURGICAL STRATEGIES, INC., Incline Village, NV (US)

( * ) Notice: Subject to any disclaimer, the term of this patent is extended or adjusted under 35 U.S.C. 154(b) by 172 days.

(21) Appl. No.: 17/049,545

(22) PCT Filed: Apr. 26, 2019

(86) PCT No.: PCT/US2019/029447
§ 371 (c)(1),
(2) Date: Oct. 21, 2020

(87) PCT Pub. No.: WO2019/210235
PCT Pub. Date: Oct. 31, 2019

(65) Prior Publication Data
US 2021/0251774 A1 Aug. 19, 2021

Related U.S. Application Data

(60) Provisional application No. 62/798,811, filed on Jan. 30, 2019, provisional application No. 62/668,118, (Continued)

(51) Int. Cl.
*A61F 2/46* (2006.01)
*A61F 2/28* (2006.01)
(Continued)

(52) U.S. Cl.
CPC .............. *A61F 2/4601* (2013.01); *A61F 2/28* (2013.01); *A61F 2/447* (2013.01); *A61F 2/4611* (2013.01); *A61B 17/1671* (2013.01); *A61F 2002/2835* (2013.01); *A61F 2002/30579* (2013.01); *A61F 2002/30593* (2013.01); *A61F 2002/4627* (2013.01); *A61F 2002/4628* (2013.01); *A61F 2002/4681* (2013.01)

(58) Field of Classification Search
CPC .......................... A61F 2/4611; F41A 19/00–70
See application file for complete search history.

(56) References Cited

U.S. PATENT DOCUMENTS 8,127,658 B1 * 3/2012 Cottle ..................... F41C 23/14
89/129.02
9,078,767 B1 * 7/2015 McLean ................ A61F 2/4425
(Continued)

OTHER PUBLICATIONS

International Application No. PCT/US2019/029447, International Search Report and Written Opinion dated Jul. 17, 2019, 8 pages.

*Primary Examiner* — Matthew J Lawson
(74) *Attorney, Agent, or Firm* — Corner Counsel, LLC

(57) ABSTRACT

Tools adapted for spinal surgery are provided. More specifically, tools having an elongate cylindrical cannula connected to a plurality of sharp-edged blades are provided for imparting a force for displacing vertebral bodies. Apparatuses and methods for accurate, rapid, and reliable placement of surgical cages or other medical implants in a patients spine are also provided.

9 Claims, 37 Drawing Sheets

Related U.S. Application Data filed on May 7, 2018, provisional application No. 62/663,851, filed on Apr. 27, 2018, provisional application No. 62/663,841, filed on Apr. 27, 2018.

(51) Int. Cl.
  *A61F 2/44* (2006.01)
  *A61B 17/16* (2006.01)
  *A61F 2/30* (2006.01)

(56) References Cited

U.S. PATENT DOCUMENTS

| | | | |
|---|---|---|---|
| 9,186,193 B2* | 11/2015 | Kleiner | A61B 17/8816 |
| 9,335,110 B1* | 5/2016 | Heizer | F41A 19/38 |
| 9,445,918 B1* | 9/2016 | Lin | A61F 2/4684 |
| 2004/0010312 A1* | 1/2004 | Enayati | A61F 2/446 |
| | | | 623/17.11 |
| 2005/0043101 A1* | 2/2005 | Knapp | F41A 19/39 |
| | | | 463/47.6 |
| 2006/0101693 A1* | 5/2006 | Langlotz | F41A 19/16 |
| | | | 42/69.01 |
| 2007/0055277 A1 | 3/2007 | Osorio et al. | |
| 2007/0213583 A1 | 9/2007 | Kim et al. | |
| 2007/0276365 A1* | 11/2007 | Song | A61F 2/4611 |
| | | | 606/60 |
| 2008/0300598 A1* | 12/2008 | Barreiro | A61F 2/442 |
| | | | 606/90 |
| 2011/0184447 A1 | 7/2011 | Leibowitz et al. | |
| 2011/0319898 A1 | 12/2011 | O'Neil et al. | |
| 2014/0257489 A1* | 9/2014 | Warren | A61F 2/442 |
| | | | 606/86 A |
| 2014/0277490 A1* | 9/2014 | Perloff | A61F 2/4455 |
| | | | 623/17.16 |
| 2015/0073555 A1* | 3/2015 | To | A61F 2/442 |
| | | | 623/17.16 |
| 2015/0190242 A1* | 7/2015 | Blain | A61F 2/447 |
| | | | 623/17.12 |
| 2015/0250606 A1* | 9/2015 | McLean | A61F 2/4611 |
| | | | 623/17.15 |
| 2016/0022438 A1* | 1/2016 | Lamborne | A61F 2/447 |
| | | | 623/17.16 |
| 2016/0047613 A1* | 2/2016 | Hudson, III | F41A 19/10 |
| | | | 42/14 |
| 2016/0106551 A1* | 4/2016 | Grimberg, Jr. | A61F 2/4601 |
| | | | 623/17.16 |
| 2017/0333200 A1* | 11/2017 | Arnin | A61F 2/4611 |
| 2022/0218494 A1* | 7/2022 | Kuyler | A61F 2/4601 |

* cited by examiner

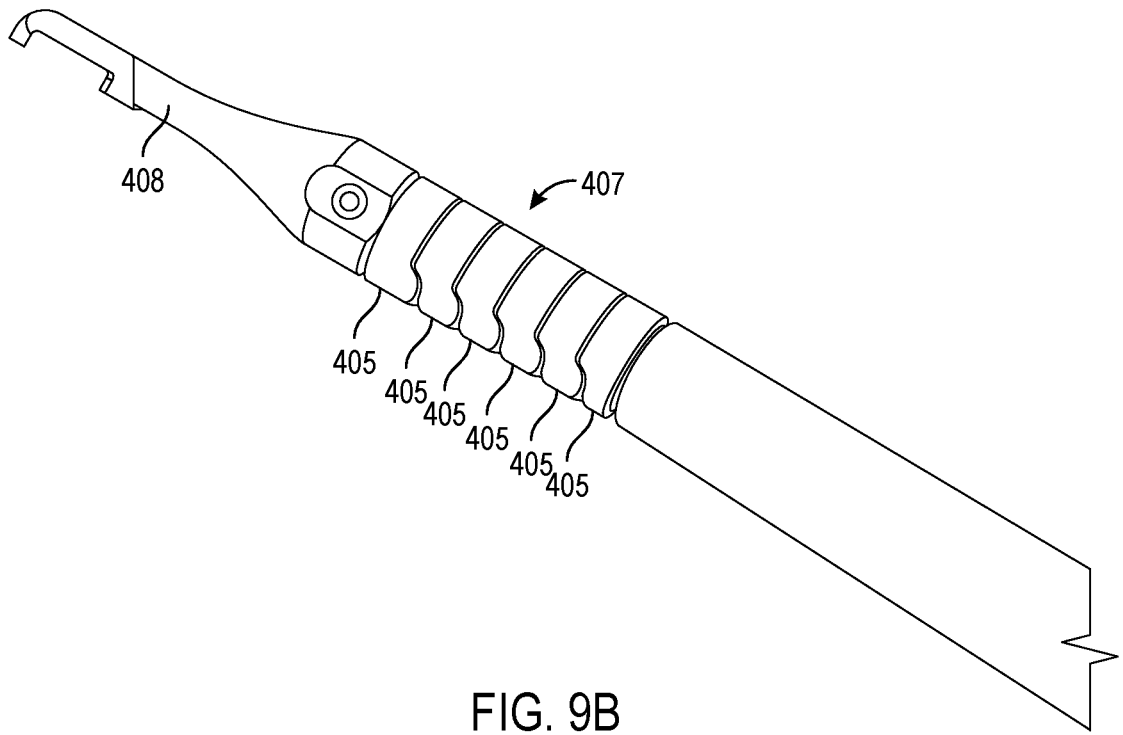
FIG. 9B
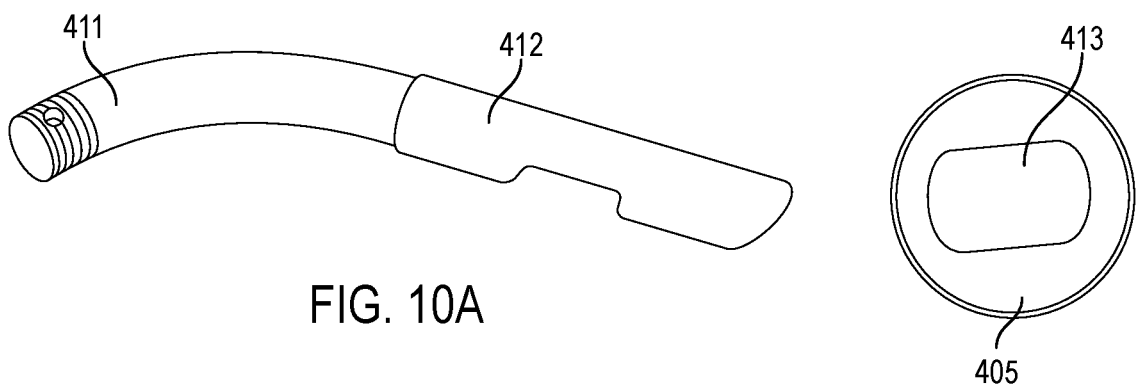
FIG. 10A
FIG. 10B

TOOLS FOR SPINAL SURGERY

CROSS-REFERENCE TO RELATED APPLICATIONS

This application claims the benefit of priority to U.S. Provisional Patent Applications 62/663,841, filed 27 Apr. 2018; 62/663,851, filed 27 Apr. 2018; 62/668,118, filed 7 May 2018; and 62/798,811, filed 30 Jan. 2019. The disclosure of each of the above-referenced patent applications is incorporated by reference in its entirety.

FIELD OF THE INVENTION

The present disclosure relates to the field of medical devices and is generally directed toward tools and methods for surgical procedures, and especially spinal fusion procedures, associated with an intervertebral disc space.

BACKGROUND OF THE INVENTION

Various types of spinal surgery require the preparation and/or cleaning of the space between adjacent vertebrae, known as the intervertebral disc space. By way of non-limiting example, spondylosyndesis, or spinal fusion, is a surgical technique used to combine two or more vertebrae into a single, rigid working unit; where fusion is intended to occur between adjacent vertebral bodies of a patient's spine, the surgeon typically prepares an opening at the site of the intended fusion by removing some or all of the disc material that exists between the adjacent vertebral bodies to be fused. Because the outermost layers of bone of the vertebral end plate are relatively inert to new bone growth, the surgeon must work on the end plate to remove at least the outermost cell layers of bone to gain access to the blood-rich, vascular bone tissue within the vertebral body. In this manner, the vertebrae are prepared in a way that encourages new bone growth onto or through an implant that is placed between the vertebrae.

Current methods of forming and preparing a disc space between vertebrae are known to include various grasping instruments, drills, rotating burrs, chisels, and other scraping implements. There has been a long felt and unmet need to provide a disc space preparation tool which is capable of spreading or separating vertebral bodies and further capable of cleaning, scouring, and/or removing tissue from a disc space.

According to the American Academy of Orthopedic Surgeons, about 250,000 spinal fusion surgeries are performed every year, mostly on adults between the ages of 45 to 64. Spinal fusion is a process by which two or more of the vertebrae that make up the spinal column are fused together with bone grafts and internal devices (such as rods) that heal into a single solid bone. Spinal fusion can eliminate unnatural motion between the vertebrae and, in turn, reduce pressure on nerve endings. In addition, spinal fusion can be used to treat, for example, injuries to spinal vertebrae caused by trauma; protrusion and degeneration of the cushioning disc between vertebrae (sometimes called slipped disc or herniated disc); abnormal curvatures (such as scoliosis or kyphosis); and weak or unstable spine caused by infections or tumors.

Individuals who suffer degenerative disc disease, natural spine deformations, a herniated disc, spine injuries or other spine disorders may require surgery on the affected region to relieve the individual from pain and prevent further injury to the spine and nerves. Spinal surgery may involve removal of damaged joint tissue, insertion of a tissue implant and/or fixation of two or more adjacent vertebral bodies. In some instances a medical implant is also inserted, such as a fusion cage. The surgical procedure will vary depending on the nature and extent of the injury. Generally, there are five main types of lumbar fusion, including: posterior lumbar fusion ("PLF"), posterior lumbar interbody fusion ("PLIF"), anterior lumbar interbody fusion ("ALIF"), circumferential 360 fusion, and transforaminal lumbar interbody fusion ("TLIF"). More recently, direct lateral interbody fusion ("D-LIF") has become available. A posterior approach is one that accesses the surgical site from the patient's back, an anterior approach is one that accesses the surgical site from the patient's front or chest, and a direct lateral approach is on that accesses the surgical site from the patient's side. There are similar approaches for fusion in the interbody or cervical spine regions. For a general background on some of these procedures and the tools and apparatus used in certain procedures, see U.S. Prov. Pat. Appl. No. 61/120,260 filed on Dec. 5, 2008, the entire disclosure of which is incorporated by reference in its entirety. In addition, further background on procedures and tools and apparatus used in spinal procedures is found in U.S. patent application Ser. No. 12/632,720 filed on Dec. 7, 2009, the entire disclosure of which is incorporated by reference in its entirety.

Vertebrectomy, or the removal or excision of a vertebra, is another type of spinal surgery that may be necessary to alleviate pain and/or correct spinal defects, such as when disk material above and below a particular vertebra protrudes from the spine and contacts the spinal cord. Once the problematic vertebra is removed, a specialized fusion cage (also called a vertebrectomy cage) may be inserted into its place to restore structural continuity to the spine.

Some disadvantages of traditional methods of spinal surgery include, for example, the pain associated with the procedure, the length of the procedure, the complexity of implements used to carry out the procedure, the prolonged hospitalization required to manage pain, the risk of infection due to the invasive nature of the procedure, and the possible requirement of a second procedure to harvest autograft bone from the iliac crest or other suitable site on the patient for generating the required quantity of cancellous and/or cortical bone.

Fusion cages provide a space for inserting a bone graft between adjacent portions of bone. Such cages are often made of titanium and are hollow, threaded, and porous in order to allow a bone graft contained within the interior of the cage of grow through the cage into adjacent vertebral bodies. Such cages are used to treat a variety of spinal disorders, including degenerative disc diseases such as Grade I or II spondylolistheses of the lumbar spine.

Surgically implantable intervertebral fusion cages are well known in the art and have been actively used to perform spinal fusion procedures for many years. Their use became popularized during the mid 1990's with the introduction of the BAK Device from the Zimmer Inc., a specific intervertebral fusion cage that has been implanted worldwide more than any other intervertebral fusion cage system. The BAK system is a fenestrated, threaded, cylindrical, titanium alloy device that is capable of being implanted into a patient as described above through an anterior or posterior approach, and is indicated for cervical and lumbar spinal surgery. The BAK system typifies a spinal fusion cage in that it is a highly fenestrated, hollow structure that will fit between two vertebrae at the location of the intervertebral disc.

Spinal fusion cages may be placed in front of the spine, a procedure known as anterior lumbar interbody fusion, or ALIF, or placed in back of the spine. The cages are generally inserted through a traditional open operation, though laparoscopic or percutaneous insertion techniques may also be used. Cages may also be placed through a posterior lumbar interbody fusion, or PLIF, technique, involving placement of the cage through a midline incision in the back, or through a direct lateral interbody fusion, or D-LIF, technique, involving placement of the cage through an incision in the side.

A typical procedure for inserting a common threaded and impacted fusion cage is as follows. First, the disc space between two vertebrae of the lumbar spine is opened using a wedge or other device on a first side of the vertebrae. The disk space is then prepared to receive a fusion cage. Conventionally, a threaded cage is inserted into the bore and the wedge is removed. A disk space at the first side of the vertebrae is then prepared, and a second threaded fusion cage inserted into the bore. Alternatively, the disk space between adjacent vertebrae may simply be cleared and a cage inserted therein. Often, only one cage is inserted obliquely into the disk space. Use of a threaded cage may be foregone in favor of a rectangular or pellet-shaped cage that is simply inserted into the disk space. Lastly, bone graft material may be inserted into the surgical area using separate tools and devices.

U.S. Pat. No. 4,743,256 issued to Brantigan ("Brantigan") discloses a traditional spinal back surgical method involving the implantation of a spinal fusion cage. The cage surfaces are shaped to fit within prepared endplates of the vertebrae to integrate the implant with the vertebrae and to provide a permanent load-bearing strut for maintaining the disc space. Brantigan teaches that these cages typically consist of a homogeneous nonresorbable material such as carbon-reinforced polymers such as polyether ether ketone (PEEK) or polyether ketone ether ketone ketone ("PEKEKK"). Although these cages have demonstrated an ability to facilitate fusion, a sufficient fusion is sometimes not achieved between the bone chips housed within the cage and the vertebral endplates. In particular, achieving a complete fusion in the middle portion of the cage has been particularly problematic. As shown in FIG. 6 herein, the upper U and lower L surfaces of these cages C have large transverse pores P which facilitate bone ingrowth, and these pores lead to an inner void space IVS which houses bone graft (not shown) which facilitates the desired fusion. In any case, Brantigan teaches the separate process and procedure for the insertion of a fusion cage and the insertion of bone graft. Indeed, local bone graft harvested from the channel cuts into the vertebrae to receive the plug supplements the fusion.

U.S. Pat. Appl. 20070043442 of Abernathie et al. ("Abernathie") discloses another traditional spinal back surgical method involving the implantation of a spinal fusion cage. Abernathie relates generally to an implantable device for promoting the fusion of adjacent bony structures, and a method of using the same. More specifically, Abernathie relates to an expandable fusion cage that may be inserted into an intervertebral space, and a method of using the same. Abernathie includes an aperture in the fusion cage to allow bone growth therethrough, as a separate procedure to the insertion of the fusion cage.

Traditional fusion cages are available in a variety of designs and composed of a variety of materials. The cages or plugs are commonly made of an inert metal substrate such as stainless steel, cobalt-chromium-molybdenum alloys, titanium or the like having a porous coating of metal particles of similar substrate metal, preferably titanium or the like as disclosed, for example, in the Robert M. Pilliar U.S. Pat. No. 3,855,638 issued Dec. 24, 1974 and U.S. Pat. No. 4,206,516 issued Jun. 10, 1980. These plugs may take the form of flat sided cubical or rectangular slabs, cylindrical rods, cruciform blocks, and the like.

U.S. Pat. No. 5,906,616 issued to Pavlov et al. ("Pavlov") discloses a fusion cage of various cylindrical and conical shapes and a method of insertion. Like Brantigan, Pavlov teaches the separate process and procedure for the insertion of a fusion cage and the insertion of bone graft. U.S. Pat. No. 5,702,449 ("McKay") discloses a spinal implant comprising a cage made of a porous biocompatible material reinforced by an outer sleeve made of a second material which is relatively stronger under the compressive load of the spine than the biocompatible material. U.S. Pat. No. 6,569,201 issued to Moumene et al. ("Moumene") teaches a bone fusion device having a structural bioresorbable layer disposed upon the outer surface of a non-resorbable support. As the bioresorbable structural layer resorbs over time, the load upon the bone graft housed within the non-resorbable support increases. Published PCT Application No. WO 99/08627 ("Gresser") discloses a fully bioresorbable interbody fusion device, as well as homogeneous composite devices containing at least 25% resorbable materials. U.S. Pat. No. 7,867,277 issued to Tohmeh discloses a spinal fusion implant of bullet shaped end.

U.S. Pat. No. 7,846,210 issued to Perez-Cruet et al. ("Perez-Cruet") discloses an interbody device assembly consisting of a fusion device and an insertion device. The insertion device positions the fusion device between two vertebrae, provides bone graft material, and then detaches from the fusion device, leaving the fusion device in place to restore disc space height. However, the Perez-Cruet device is designed to receive bone graft material from its insertion device and distribute the material away from the fusion device. In most embodiments of the fusion device, a center plate is positioned immediately downstream of the received bone graft material and directs the bone graft to opposing sides of the fusion device. (See, for example, FIG. 20 depicting plate 308 directing bone graft material 392 along the exterior sides of the fusion device 302). As such, the Perez-Cruet fusion device is unlikely to completely fill the areas near of its fusion cage and deliver bone graft material to the surrounding bone graft site. Furthermore, none of the Perez-Cruet fusion device embodiments feature a defined interior space or a cage-style design. Indeed, the Perez-Cruet fusion device explicitly teaches away from a contained-interior, fusion-cage-style device, asserting that its fusion device fills all of the disc space as opposed to a cage design, which contains the bone material. Furthermore, the Perez-Cruet does not feature a distal tip that functions to precisely position the fusion device and stabilize the device during delivery of bone graft material.

U.S. Pat. No. 7,985,256 issued to Grotz et al. ("Grotz") discloses an expandable spinal implant for insertion between opposed vertebral end plates. The implant is a cylinder block of slave cylinders; a central cavity between the cylinders receives bone graft material and pistons positioned within the cylinders provide a corrective bone engaging surface for expanding against a first vertebral end plate. The insertion tool used to place the spinal implant includes a handle and hollow interior for housing hydraulic control lines and a bone graft supply line. The Grotz system does not allow precise positioning or delivery of bone graft material without an implant and requires a complex and bulky insertion tool.

U.S. Pat. Appl. 2010/0198140 to Lawson ("Lawson") discloses a tool comprising a cannula with an open slot at the distal end and a closed tip. Lawson's tool employs tamps to push bone aside and open up a void for filling; solid bone pellets are then rammed down the hollow interior of the cannula by a tamper and delivered to the surgical site. Lawson does not allow precise positioning or delivery of viscous bone graft material and has no capability to interconnect or integrate with an implant such as a bone graft fusion cage.

U.S. Pat. Appl. 2010/0262245 to Alfaro et al. ("Alfaro") discloses a delivery system for an intervertebral spacer and a bone grafting material comprising a spacer disengagingly attached to a hollow handle. The handle comprises a chamber and bone grafting material-advancing means for introducing bone grafting material from the chamber into the spacer and the intervertebral spaces. The Alfaro system does not allow precise positioning or delivery of bone graft material through a distal tip that precisely positions the fusion device and stabilizes the device during delivery of bone graft material, and does not allow primarily lateral injection of bone graft fusion material.

Therefore, there is a long-felt need for an apparatus and method for near-simultaneous and integrated precision delivery of bone graft material during the placement of surgical cages or other medical implants in a patient's spine. Particularly, there is a long-felt need for devices and methods of accurately, easily, and quickly placing a surgical cage in a desired position during a spinal surgery. The present invention solves these needs, and particularly provides a device which allows a user, generally a surgeon, to selectively attach and detach a surgical cage from leaves, tabs, or other engaging elements of the device. Since fusion cages generally distract the disk space, they volumetrically dilute the concentration of bone placed prior to cage insertion. Since fusion success is proportional to the amount of bone graft delivered to the surgical site, a cage which allows filling of the disk space in its distracted position results in fusion success. The improved fusion yield from filling the entire potential grafting space allows the surgeon to perform minimally invasive spinal surgery with greater confidence that the fusion will heal and not have to resort to multiple (and morbid) sites for placement of bone graft. The present invention also provides spinal fusion cages and other surgical implants that include a selectively attachable element, such as a plate, shim, veneer, or similar element, that augments a height of the surgical implant when the implant is intended for implantation in a patient with a greater-than-usual distance between target vertebrae. Furthermore, the additive shims can allow for correction of spinal deformity by being available in angled applications to correct scoliosis, kyphosis or hyperlordosis.

SUMMARY OF THE INVENTION

Embodiments of the present invention disclose a disc space preparation tool, comprising a cylindrical cannula; a grip, selected from the group consisting of a T-type grip, a pistol-type grip, and a handlebar-type grip, at a proximal end of the disc space preparation tool; and a plurality of sharp-edged blades at a distal end of the disc space preparation tool, wherein the sharp-edged blades are reconfigurable between at least a first configuration and a second configuration, wherein a shape of at least one of the sharp-edged blades is substantially linear in the first configuration and arcuate in the second configuration.

In embodiments, the plurality of sharp-edged blades may comprise four sharp-edged blades.

In embodiments, a material of the plurality of sharp-edged blades may comprise a nickel-titanium alloy.

In embodiments, the plurality of sharp-edged blades may be in the first configuration when a user imparts a first force on the grip and in the second configuration when a user imparts a second force on the grip. By way of non-limiting example, the first force may be a pulling force and the second force may be a pushing force, or the first force may be a pushing force and the second force may be a rotational force.

In embodiments, at least a proximal portion of the plurality of sharp-edged blades may be disposed within an interior of the cylindrical cannula when the plurality of sharp-edged blades is in the first configuration.

In embodiments, the plurality of sharp-edged blades may define and surround a void space, wherein the void space is approximately cylindrical when the plurality of sharp-edged blades is in the first configuration and approximately spheroid when the plurality of sharp-edged blades is in the second configuration.

In embodiments, the plurality of sharp-edged blades may comprise a whisk structure. In embodiments, the disc space preparation tool may further comprise a spring interconnected to a proximal end of the plurality of sharp-edged blades, the spring permitting displacement of the plurality of sharp-edged blades relative to an axis of the cylindrical cannula. The disc space preparation tool may still further comprise a hollow connective element and one or more stays, interconnected to the grip and the spring and permitting the user to selectively move the plurality of sharp-edged blades in a desired direction.

In embodiments, the disc space preparation tool may comprise a suction means for conveying a negative pressure to the plurality of sharp-edged blades.

In embodiments, the disc space preparation tool may further comprise a shaft interconnecting the grip to the cylindrical cannula, wherein the shaft and the cylindrical cannula form an angle therebetween. The angle may preferably be between about 3 degrees and about 25 degrees, and more preferably between about 5 degrees and about 15 degrees.

In embodiments, at least one of the cylindrical cannula and the grip may comprise a material selected from the group consisting of aluminum, iron, titanium, steel, medical grade plastic, and PEEK. Where the material is steel, the steel may be selected from the group consisting of stainless steel, martensitic steel, grade 316L austenitic steel, and grade 316LVM austenitic steel. Where the steel is stainless steel, the stainless steel may be selected from the group consisting of surgical stainless steel and grade 316 stainless steel.

In embodiments, the cylindrical cannula may comprise a flexible material and may be resiliently deformable.

In embodiments, the disc space preparation tool may further comprise a means for selectively rotating the plurality of sharp-edged blades with respect to at least one of the cylindrical cannula and the grip.

In various embodiments, a plurality of surgical tools is provided wherein the plurality of surgical tools comprises tools of different sizes and/or shapes. Thus, a user or surgeon is provided with numerous different cylindrical cannula and distal end combinations so that the appropriate tool may be selected for the appropriate application. One of skill in the art will recognize that different patient characteristics and operating conditions may dictate different device selection. Accordingly, the present invention contemplates providing a plurality of tools which offers such discretion.

Other embodiments of the present invention provide a means for a user to selectively activate or actuate features of an intervertebral workspace tool in order to scrape or otherwise collect various tissue disposed within the disc space. For example, it is contemplated that tools of the present invention comprise movable features, such as selectively engageable clam shell or shovel-type devices which are activated and/or controlled by features at a proximal end of the device adapted for user interaction. In alternative embodiments, user operated features are provided such as pressure applying means. Pressure applying means of the present invention may comprise, for example, a working cylindrical cannula and distal end to which a vacuum pressure is supplied, thereby drawing debris toward at least a distal end of the tool(s).

In various embodiments, one or more disc space preparation tools are provided, the one or more disc space preparation tools being capable of transmitting or applying a positive pressure to a disc space. For example, a quantity of fluid or gas may be directed through portions of a disc space preparation tool by a positive pressure for impacting various regions and materials within the disc space.

In further embodiments, the present invention comprises various fenestrations, portals, and/or apertures adapted for transmitting a pressure (e.g. a positive or negative pressure) induced by a device located external to the workspace and transmitted through portions of a tool. Vacuum pressures may be selectively applied to various portions of an intervertebral work space tool based on necessity and/or user preference.

In various embodiments, tools of the present invention are made from a biocompatible material such as a thermal plastic (e.g. PEEK), a polymer, metal, combination thereof or otherwise, such as desired and/or is appropriate.

In various embodiments, one or more portions of tools of the present invention comprise rasps, teeth, or structures having various combinations of plateaus and/or valleys for contact with a vertebral body, end plate, and various material and features located within a vertebral body. The plurality of rasps, teeth, or scales facilitate insertion of the device into the intervertebral work space while not substantially preventing or impeding removal of the device. In embodiments, the teeth or geometry of portions of the tools are adapted to facilitate the removal of at least the outer most cell layers of bone to gain access to vascular bone tissue within the disc space and otherwise clean or clear the work space. For example, various features shown and described in U.S. Pat. No. 7,461,803 to Boerner and U.S. Pat. No. 7,632,276 to Fishbein, which are incorporated by reference herein in their entireties, and variations thereof, may be incorporated into embodiments of the present invention.

In various embodiments, the present invention comprises channels or flutes for guiding materials that have been dislodged or scraped away from portions of the intervertebral workspace. For example, a distal end of a disc space preparation tool according to embodiments of the present invention may comprise channels or apertures which direct material that has been scraped by additional features of the tool into a region or volume of the disc space preparation tool that is adapted for securing and/or temporarily retaining the dislodged material. In further embodiments, additional features are employed to compliment such channels or retaining apertures. For example, in one embodiment, a vacuum pressure is applied through a cylindrical cannula portion of a disc space preparation tool which facilitates maintaining debris and/or dislodged materials within receiving apertures of the present invention while the device is manipulated or removed from the intervertebral workspace.

In various embodiments, the present invention comprises features and devices for physically sealing, closing, or otherwise containing receiving apertures. For example, receiving apertures or fenestrations which are generally open during surgical procedures may be selectively sealed or closed by a user through the use of features disposed at a proximal end of the device.

Incorporated by reference in their entireties are the following U.S. patents and patent applications directed generally to methods and apparatus related to spinal procedures, thus providing written description support for various aspects of the present disclosure. The U.S. patents and pending applications incorporated by reference are as follows: U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and 2008/0255564 to Michelson.

A variety of known vacuum pumps and devices may be utilized in combination with aspects of the present invention. By way of example, U.S. Pat. No. 5,282,744 to Meyer, U.S. Pat. No. 4,580,978 to Motola et al., U.S. Pat. No. 4,991,570 to Bullard, U.S. Pat. No. 5,311,640 to Holland, and U.S. Patent Application Publication No. 2007/0172790 to Doucette, Jr. et al., which are incorporated by reference in their entireties herein, generally relate to the field of dentistry. Various features and aspects described in these references may be incorporated into aspects of the present invention.

In various embodiments, a positive pneumatic pressure may be applied to a disc space through portions of a tool. For example, air or other gases and/or fluids may be provided to a disc space to blast or clear a surgical work area or disc space. U.S. Pat. No. 6,004,191 to Schur et al., U.S. Pat. No. 4,430,062 to Henrichsen et al., U.S. Pat. Nos. 4,877,399, 6,216,573 to Moutafis et al., U.S. Pat. No. 7,122,017 to Moutafis et al., U.S. Pat. No. 6,960,182 to Moutafis et al., U.S. Pat. No. 5,944,686 to Patterson et al., and U.S. Patent Application Publication No. 2005/0267443 to Staid et al., which are incorporated by reference herein in their entireties relate to various devices and methods for delivering a volume of air or fluid to a desired location. In various embodiments, the present invention comprises delivering force or pressurized air, gas, fluids, and various combinations thereof to a disc space and a distal end of a disc space preparation tool. For example, ambient air, inert gases, oxygen, water, saline, and various combinations thereof may be directed to a disc space through features of the present invention (e.g. channels housed within a disc space preparation tool). One of skill in the art will recognize that such features may direct such substances to a portion of a disc space (e.g. a disc end plate) and/or to a portion of the tool which has become contaminated with various fluid, tissue, debris etc. (e.g. a distal end).

In various embodiments, an elongate cylindrical cannula is comprised of one or more flexible materials, thus creating a cylindrical cannula which is resiliently deformable. For example, cylindrical cannulas of the present invention may comprise helical spring members designed to yield a certain amount under appropriate moments forces yet generally restore themselves to a linear elongate arrangement absent a certain magnitude of force. Alternatively, a cylindrical cannula may be comprised of elastically deformable plastics allowing for flexible movement away from its axis under external force and return to or approximately to an initial position in the absence of such a force. Thus, embodiments of the present invention contemplate an elongate cylindrical cannula adapted for receiving and transmitting a compressive force applied by a surgeon, yet provides enough compliance in moment to accommodate various obstructions and prevent or reduce the risk of devices becoming "wedged" or lodged into a disc space. In various embodiments, various polyethylenes, polyvinylchloride, urethanes, PEEK, elastically deformable metals, and other similar materials may comprise flexible elongate cylindrical cannulas of the present invention. In one embodiment, a flexible cylindrical cannula comprises a biocompatible material (e.g. PEEK). However, as one of ordinary skill in the art will recognize, the cylindrical cannula is not an implantable device. Thus, in alternative embodiments, the cylindrical cannula is comprised various surgical grade materials suitable for surgical tools generally.

In various embodiments, the present invention comprises various imaging devices for providing feedback to a user.

A variety of instrumentation techniques have become available to assist with lumbar interbody stabilization. These include different approaches for placing fusion cages (oblique, lateral, anterior or posterior), using stackable cages, expandable cages and the application of cage coatings.

By way of providing additional background, context, and to further satisfy the written description requirements of 35 U.S.C. § 112, the following references are incorporated by reference in their entireties for the express purpose of explaining the nature of the surgical procedures in which fusion cages are used and to further describe the various tools and other apparatus commonly associated therewith: U.S. Pat. No. 6,569,201 to Moumene et al.; U.S. Pat. No. 6,159,211 to Boriani et al.; U.S. Pat. No. 4,743,256 to Brantigan; U.S. Pat. Appl. 2007/0043442 to Abernathie et al.; U.S. Pat. Nos. 3,855,638 and 4,206,516 to Pilliar; U.S. Pat. No. 5,906,616 issued to Pavlov et al.; U.S. Pat. No. 5,702,449 to McKay; U.S. Pat. No. 6,569,201 to Moumene et al.; PCT Appl. No. WO 99/08627 to Gresser; U.S. Pat. Appl. 2012/0022651 to Akyuz et al.; U.S. Pat. Appl. 2011/0015748 to Molz et al.; U.S. Pat. Appl. 2010/0249934 to Melkent; U.S. Pat. Appl. 2009/0187194 to Hamada; U.S. Pat. No. 7,867,277 issued to Tohmeh; U.S. Pat. No. 7,846,210 to Perez-Cruet et al.; U.S. Pat. No. 7,985,256 issued to Grotz et al.; U.S. Pat. Appl. 2010/0198140 to Lawson; and U.S. Pat. Appl. 2010/0262245 to Alfaro et al.

By way of providing additional background and context, the following references are also incorporated by reference in their entireties for the purpose of explaining the nature of spinal fusion and devices and methods commonly associated therewith: U.S. Pat. No. 7,595,043 issued to Hedrick et al.; U.S. Pat. No. 6,890,728 to Dolecek et al.; U.S. Pat. No. 7,364,657 to Mandrusov, and U.S. Pat. No. 8,088,163 to Kleiner.

In addition, by way of providing additional background and context, the following references are also incorporated by reference in their entireties for the purpose of explaining the nature of spinal fusion and devices and methods commonly associated therewith: US Pat. No. D647,202 entitled "Bone Marrow Harvesting Device" to Seifert issued Oct. 18, 2011; U.S. Pat. No. 7,897,164 entitled "Compositions and Methods for Nucleus Pulposus Regeneration" to Seifert issued Mar. 1, 2011; US Pat. Appl. No. 2010/0112029 entitled "Compositions and Methods for Nucleus Pulposus Regeneration" to Seifert issued May 6, 2010; US Pat. Appl. No. 2010/0021518 entitled "Foam Carrier for Bone Grafting" to Scifert issued Jan. 28, 2010; U.S. Pat. No. 7,824,703 entitled "Medical Implants with Reservoir(s), and Materials Preparable From Same" to Scifert, et al., issued Nov. 2, 2010; US Pat. Appl. No. 2006/0247791 entitled "Multi-Purpose Medical Implant Devices" to McKay, et al., issued Nov. 2, 2006; US Pat. Appl. No. 2007/0225811 entitled "Conformable Orthopedic Implant" to Seifert, et al., issued Sep. 27, 2007; U.S. Pat. No. 6,746,487 entitled "Intramedullary Trial Fixation Device" to Seifert, et al., issued Jun. 9, 2004; US Pat. Appl. No. 2013/0073041 entitled "Medical Implants With Reservoir(s), and Materials Preparable From Same" to Seifert et al., issued Mar. 21, 2013; US Pat. Appl. No. 2010/0266689 entitled "Tissue Augmentation With Active Agent For Wound Healing" to Simonton et al., issued Oct. 21, 2010; US Pat. Application No. 2011/0028393 entitled "Flowable Paste And Putty Bone Void Filler" to Vickers et al., issued Feb. 3, 2011; US Pat. Appl. No. 2009/0099660 entitled "Instrumentation To Facilitate Access Into The Intervertebral Disc Space And Introduction Of Materials Therein" to Scifert issued Apr. 16, 2009; US Pat. Appl. No. 2011/0014587 entitled "System And Methods Of Preserving An Oral Socket" to Spagnoli et al., issued Jan. 20, 2011; U.S. Pat. No. 8,148,326 entitled "Flowable Carrier Matrix and Methods for Delivering to a Patient" to Beals et al., issued Apr. 3, 2012; US Pat. Appl. No. 2008/0260598 entitled "Devices, Methods and Systems for Hydrating a Medical Implant Material" to Gross et al., issued Oct. 23, 2008; US Pat. Appl. No. 2007/0265632 entitled "Bone Cutting Template and Method of Treating Bone Fractures" to Scifert et al., issued Nov. 15, 2007; U.S. Pat. No. 8,293,232 entitled "Flowable Carrier Matrix and Methods for Delivering to a Patient" to Beals et al., issued Oct. 23, 2012; U.S. Pat. No. 8,198,238 entitled "Flowable Carrier Matrix and Methods for Delivering to a Patient" to Beals et al., issued Jun. 12, 2012; U.S. Pat. No. 7,939,092 entitled "Cohesive Osteogenic Putty and Materials Therefor" to McKay et al., issued May 10, 2011; US Pat. Appl. No. 2007/0264300 entitled "Therapeutic Agent Carrier and Method of Treating Bone Fractures" to Scifert et al., issued Nov. 15, 2007; US Pat. Appl. No. 2011/0020768 entitled "Implantable Screw and System for Socket Preservation" to Spagnoli et al., issued Jan. 27, 2011; US Pat. Appl. No. 2012/0065687 entitled "Multi-Radius Vertebral Rod with a Varying Stiffness" to Ballard et al., issued Mar. 15, 2012; US Pat. No. 2007/0225219 entitled "Intramedullary Drug Delivery Device and Method of Treating Bone Fractures" to Boden et al., issued Sep. 27, 2007; U.S. Pat. No. 7,723,291 entitled "Release of BMP, Bioactive Agents and/or Cells Via a Pump into a Carrier Matrix" to Beals et al., issued May 25, 2010; U.S. Pat. No. 7,671,014 entitled "Flowable Carrier Matrix And Methods For Delivering To A Patient" to Beals et al., issued Mar. 2, 1010; U.S. Pat. No. 7,897,564 entitled "Flowable Carrier Matrix and Methods for Delivering to a Patient" to Beals et al., issued Mar. 1, 2011; US Pat. Application No. 2011/0160777 entitled "System and Methods of Maintaining Space for Augmentation of the Alveolar Ridge" to Spagnoli et al., issued Jun. 30, 2011; US Pat. Application No. 2009/0246244 entitled "Malleable Multi-Component Implants and Materials Therefor" to McKay et al., issued Oct. 1, 2009; US Pat. Application No. 2009/0246244 entitled "Malleable Multi-Component Implants and Materials Therefor" to McKay et al., issued Oct. 1, 2009; US Pat. No. 2013/0110169 entitled "Vertebral Rod System and Methods of Use" to Hynes, et al., issued May 2, 2013; US Pat. Appl. No. 2011/0184412 entitled "Pre-Assembled Construct With One Or More Non-Rotating Connectors For Insertion Into a Patient" to Scifert, et al., issued Jul. 28, 2011; U.S. Pat. No. 7,964,208 entitled "System and Methods of Maintaining Space For Augmentation of the Alveolar Ridge" to Spagnoli, et al., issued Jun. 21, 2011; U.S. Pat. No. 8,080,521 entitled "Flowable Carrier Matrix and Methods for Delivering to a Patient" to Beals, et al., issued Dec. 20, 2011; US Pat. Appl. No. 2009/0142385 entitled "Compositions for Treating Bone Defects" to Gross, et al., issued Jun. 4, 2009; U.S. Pat. No. 7,578,820 entitled "Devices and Techniques for a Minimally Invasive Disc Space Preparation and Implant Insertion" to Moore, et al., issued Aug. 25, 2009; US Pat. Appl. No. 2010/0305575 entitled "Methods and Apparatus for Performing Knee Arthroplasty" to Wilkinson, et al., issued Dec. 2, 2010; US Pat. Appl. No. 2011/0021427 entitled "Biphasic Calcium Phosphate Cement for Drug Delivery" to Amsden, et al., issued Jan. 27, 2011; US Pat. Appl. No. 2012/0259335 entitled "Patello-Femoral Joint Implant and Instrumentation" to Scifert, et al., issued Oct. 11, 2012; US Pat. Appl. No. 2011/0106162 entitled "Composite Connecting Elements for Spinal Stabilization Systems" to Ballard, et al., issued May 5, 2011; US Pat. Appl. No. 2004/0073314 entitled "Vertebral Body and Disc Space Replacement Devices" to White, et al., issued Apr. 15, 2004; U.S. Pat. No. 7,513,901 entitled "Graft Syringe Assembly" to Scifert, et al., issued Apr. 7, 2009; US Pat. Appl. No. 2010/0004752 entitled "Vertebral Body and Disc Space Replacement Devices" to White, et al., issued Jan. 7, 2010; U.S. Pat. No. 7,615,078 entitled "Vertebral Body and Disc Space Replacement Devices" to White, et al., issued Nov. 10, 2009; U.S. Pat. No. 6,991,653 entitled "Vertebral Body and Disc Space Replacement Devices" to White, et al., issued Jan. 31, 2006; US Pat. Appl. No. 2010/0331847 entitled "Methods and Apparatus for Performing Knee Arthroplasty" to Wilkinson, et al., issued Dec. 30, 2010; US Pat. Appl. No. 2006/0116770 entitled "Vertebral Body and Disc Space Replacement Devices" to White, et al., issued Jun. 1, 2006; and U.S. Pat. No. 8,246,572 entitled "Bone Graft Applicator" to Cantor, et al., issued Aug. 21, 2012.

Although well suited for use in human patients, and although much of the discussion of the present invention is directed toward use in humans, advantages offered by the present invention may be realized in the veterinary and scientific fields for the benefit and study of all types of animals and biological systems. Additionally, although the fusion cages of the present invention are particularly well-suited for implantation into the spinal column between two target vertebrae, and although much of the discussion of the present invention is directed toward their use in spinal applications, advantages offered by embodiments of the present invention may also be realized by implantation at other locations within a patient where the fusion of two or more bony structures may be desired. As one of skill in the art will appreciate, the present invention has applications in the general field of skeletal repair and treatment, with particular application to the treatment of spinal injuries and diseases. It should be appreciated, however that the principles of the present invention can also find application in other areas, specifically where there is a desire to constrain added fluid material to particular regions. For example, the present invention finds application in methods where the objective is to confine added material to predetermined areas of interest and to prohibit the undesired translocation of such material until an operation is complete and/or until a predetermined later time.

The phrase "removably attached" and/or "detachable" is used herein to indicate an attachment of any sort that is readily releasable.

The phrase "integrated fusion cage", "spinal fusion implant", "biological implant" and/or "fusion cage" is used here to indicate a biological implant.

Embodiments of the present invention disclose a surgical implant delivery device, comprising a cannula, comprising at least one track or groove in an external surface of a distal end of the cannula; a positioning handle, comprising a grip selected from the group consisting of a T-type grip, a pistol-type grip, and a handlebar-type grip, at a proximal end of the surgical implant delivery device, the grip comprising a user-operable trigger; and an engaging portion, comprising at least one flexible strip disposed at least partially within the at least one track or groove of the cannula, each flexible strip comprising at least one engaging element, wherein the engaging portion is configured such that the at least one engaging element of the surgical implant delivery devices engages a corresponding engaging element of a surgical implant when the user-operable trigger is not actuated and disengages the corresponding engaging element of the surgical implant when the user-operable trigger is actuated.

In embodiments, the at least one engaging element may be a leaf or tab extending outwardly from a longitudinal axis of the engaging portion. The leaf or tab may be in a compressed position when the user-operable trigger is not actuated and in an uncompressed position when the user-operable trigger is actuated.

In embodiments, a material of the flexible strip may comprise a metal. The metal may be a nickel-titanium alloy.

In embodiments, the user-operable trigger may be configured to be actuated by compressing, pulling, or squeezing.

In embodiments, the user-operable trigger is operable with one hand. The user-operable trigger may be operable with one finger.

In embodiments, at least part of the at least one flexible strip may extend beyond the distal end of the cannula.

In embodiments, the at least one track or groove may comprise two tracks or grooves and the at least one flexible strip may comprise two flexible strips. The two tracks or grooves and the two flexible strips may be disposed in a rotationally symmetric configuration about the distal end of the cannula.

In embodiments, the cannula may be cylindrical. At least one of an inner diameter of the cannula and an outer diameter of the cannula may be about 8 millimeters.

In embodiments, the surgical implant may be a spinal fusion cage.

In embodiments, the cannula may be operable to receive bone graft material and deliver the bone graft material to at least one of an interior of the surgical implant and an exterior of the surgical implant.

In embodiments, the cannula may comprise a ferrous material.

In embodiments, the positioning handle may be selectively removable from the cannula.

In embodiments, the positioning handle may be welded to the cannula.

In embodiments, the distal end of the cannula may be curved or angled relative to a proximal end of the cannula.

In embodiments, a cross-section of at least the distal end of the cannula may be rectangular.

Embodiments of the present invention disclose a surgical implant system, comprising a surgical implant, comprising at least one attachment element and a selectively attachable and detachable plate; a cannula; and at least one engaging element, comprising a shape-memory material and disposed at least partially within an interior volume of a distal end of the cannula, wherein the at least one engaging element is selectively reconfigurable between a first configuration and a second configuration, wherein the at least one engaging element engages the attachment element in the first configuration and disengages from the attachment element in the second configuration.

In embodiments, the at least one engaging element may comprise a leaf or tab extending outwardly from the distal end of the cannula. The leaf or tab may, but need not, retract, or be retractable, into the interior volume of the cannula when the engaging element is in the second configuration.

In embodiments, the shape-memory material may comprise a metal. The metal may be a nickel-titanium alloy.

In embodiments, the surgical implant system may further comprise a user-operable trigger associated with the at least one engaging element, whereby the at least one engaging element is reconfigurable between the first configuration and the second configuration by actuation of the user-operable trigger. The user-operable trigger may be actuated by compressing, pulling, or squeezing, and may be operable with one hand, preferably with one finger.

In embodiments, the surgical implant system may comprise two or more attachment elements and two or more engaging elements. The attachment elements may be disposed in a rotationally symmetric arrangement about an exterior surface of the surgical implant, including, by way of non-limiting example, on top and bottom exterior faces of the surgical implant, or on left and right exterior faces of the surgical implant. The engaging elements may likewise be disposed in a rotationally symmetric arrangement about an interior surface of the cannula.

In embodiments, the cannula may be cylindrical. At least one of an inner diameter of the cannula and an outer diameter of the cannula may be about 8 millimeters.

In embodiments, the surgical implant may be a spinal fusion cage.

In embodiments, the surgical implant may be expandable. The at least one engaging element may allow a user to expand the expandable surgical implant while the surgical implant is securely attached to the engaging element, and then detach the surgical implant from the engaging element after the surgical implant has been expanded.

In embodiments, the cannula may be operable to receive bone graft material and deliver the bone graft material to at least one of an interior of the surgical implant and an exterior of the surgical implant.

In embodiments, the cannula may comprise a ferrous material.

In embodiments, the distal end of the cannula may be curved or angled relative to a proximal end of the cannula.

In embodiments, a cross-section of at least the distal end of the cannula may be rectangular.

In embodiments, the engaging element may be configured to attach or detach the selectively attachable and detachable plate from the surgical implant.

Embodiments of the present invention also disclose a surgical implant, comprising a selectively attachable and detachable plate.

In embodiments, the selectively attachable and detachable plate may augment a height of the surgical implant. The height of the surgical implant may, by way of non-limiting example, be between about 8 millimeters and about 14 millimeters when the plate is detached, and between about 16 millimeters and about 22 millimeters when the plate is attached.

In embodiments, a means by which the plate is selectively attachable and detachable may be a snug-fit mechanism, such that the plate may "snap" onto a body of the surgical implant. By way of non-limiting example, a roughened or ridged surface on one face of the selectively attachable and detachable plate may be configured to engage or interdigitate with a corresponding roughened or ridged surface on one face of the body of the surgical implant.

In embodiments, the surgical implant may further comprise at least one attachment element, configured to selectively engage and disengage an engaging element of a cannula or other surgical implant delivery device or system. The at least one attachment element may be a groove, slot, or track, and may be adapted to receive a leaf or tab of the engaging element. The at least one attachment element may be disposed on any one or more faces of an external surface of a body of the surgical implant and/or of the selectively attachable and detachable plate, such as a top face, a right face, a bottom face, and/or a left face. The attachment element may comprise a groove, slot, or track in the selectively attachable and detachable plate and a groove, slot, or track in a corresponding location of the body of the surgical implant.

In embodiments, the surgical implant may be expandable. The at least one attachment element may allow a user to expand the expandable surgical implant while the surgical implant is securely attached to an engaging element of a cannula or other surgical implant delivery device or system, and then detach the surgical implant from the engaging element after the surgical implant has been expanded.

A preferred method as disclosed herein comprises precisely inserting a fusion cage into a surgical area using a delivery device. The surgical implant device may then be selectably detached from the delivery device to remain at the surgical site.

Another method as disclosed herein comprises inserting a fusion cage into a prepared disk space using a delivery device, such that the fusion cage portion fits snugly into the prepared disk space (the fusion cage is designed in variable heights and lengths so as to fit snugly into the prepared disk space), after which the fusion cage is detached from the delivery device and left in the disk space.

Another embodiment for the delivery device comprises a detachable fusion cage that is detachable, or removably attached, by any of several means. As disclosed above, in one embodiment, the fusion cage is configured with one or more elements that engage with one or more leaves, tabs, or similar elements of an engaging portion of the device. In a preferred embodiment, the delivery device comprises a user-operable trigger and flexible strips within tracks at each end of a cannula, wherein leaves or tabs disposed on the flexible strips may selectively engage with or disengage from the fusion cage when a user actuates the trigger.

In another embodiment for the delivery device, the detachable fusion cage is detachable by way of an indent-tab, such that when the user actuates the trigger or other control element, the indent-tab is pushed outwardly, away from the engaging portion of the device, and thus is no longer attached to the rest of the delivery device.

In another embodiment for the delivery device, the detachable fusion cage is detachable by way of receipt of an electrical, mechanical, pneumatic, hydraulic or other communication imparted by the user upon the trigger or other control element.

In another embodiment for the delivery device, the detachable fusion cage is detachable by way of a Luer taper or Luer fitting connection, such as in a LuerLok® or Luer-Slip® configuration or any other Luer taper or Luer fitting connection configuration. For purposes of illustration, and without wishing to be held to any one embodiment, the following U.S. patent application is incorporated herein by reference in order to provide an illustrative and enabling disclosure and general description of means to selectably detach the fusion cage of the delivery device: U.S. Patent Appl. No. 2009/0124980 to Chen.

In another embodiment for the delivery device, the detachable fusion cage is detachable by way of a pedicle dart by threadable rotation to achieve attachment, detachment, and axial movement. Other ways include a quick key insertion, an external snap detent, or magnetic attraction or any other structure. For purposes of illustration, and without wishing to be held to any one embodiment, the following U.S. patent application is incorporated herein by reference in order to provide an illustrative and enabling disclosure and general description of means to selectably detach the fusion cage of the delivery device: U.S. Patent Appl. No. 2009/0187194 to Hamada.

In another embodiment for the delivery device, the detachable fusion cage is detachable by use of magnetism. More specifically, the detachable fusion cage can be made to feature a magnetic field pattern and a resulting force R that are adjustable and may be of different character than the rest of the delivery device. With permanent magnets, such adjustments can be made mechanically by orienting various permanent magnet polar geometries and corresponding shapes relative to one another. U.S. Pat. No. 5,595,563 to Moisdon describes further background regarding such adjustment techniques, which is hereby incorporated by reference in its entirety. Alternatively or additionally, electromagnets could be used in combination with permanent magnets to provide adjustability. In further embodiments, the magnets and corresponding fields and the resultant magnetic field pattern can include both attraction forces from placement of opposite pole types in proximity to one another and repulsion forces from placement of like pole types in proximity to one another. As used herein, "repulsive magnetic force" or "repulsive force" refers to a force resulting from the placement of like magnetic poles in proximity to one another either with or without attractive forces also being present due to opposite magnetic poles being placed in proximity to one another, and further refers to any one of such forces when multiple instances are present. U.S. Pat. No. 6,387,096 is cited as a source of additional information concerning repulsive forces that are provided together with attractive magnetic forces, which is hereby incorporated by reference. In another alternative embodiment example, one or more of surfaces of the fusion cage are roughened or otherwise include bone-engaging structures to secure purchase with vertebral surfaces. In yet other embodiments, the selectable detachable feature between the detachable fusion cage and the delivery device can include one or more tethers, cables, braids, wires, cords, bands, filaments, fibers, and/or sheets; a nonfabric tube comprised of an organic polymer, metal, and/or composite; an accordion or bellows tube type that may or may not include a fabric, filamentous, fibrous, and/or woven structure; a combination of these, or such different arrangement as would occur to one skilled in the art. Alternatively or additionally, the selectable detachable feature between the detachable fusion cage and the delivery device can be arranged to present one or more openings between members or portions, where such openings extend between end portions of the fusion cage. For purposes of illustration, and without wishing to be held to any one embodiment, the following U.S. patent application is incorporated herein by reference in order to provide an illustrative and enabling disclosure and general description of means to selectably detach the fusion cage of the delivery device: U.S. Patent Appl. No. 2011/0015748 to Molz et al.

In another embodiment for the delivery device, the detachable fusion cage is detachable by use of plasma treatment. The term "plasma" in this context is an ionized gas containing excited species such as ions, radicals, electrons and photons. (Lunk and Schmid, Contrib. *Plasma Phys.*, 28: 275 (1998)). The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces (Ratner, Ultrathin Films (by Plasma deposition), 11 *Polymeric Materials Encyclopedia* 8444-8451, (1996)). Plasma treatment is an effective method to uniformly alter the surface properties of substrates having different or unique size, shape and geometry including but not limited to bone and bone composite materials. Plasma Treatment may be employed to effect magnetic properties on elements of the delivery device, or to provide selectable detachment of the fusion cage. For purposes of illustration, and without wishing to be held to any one embodiment, the following U.S. patent application is incorporated herein by reference in order to provide an illustrative and enabling disclosure and general description of means to selectably detach the fusion cage of the delivery device: U.S. Pat. No. 7,749,555 to Zanella et al.

In another embodiment, an intervertebral bone graft delivery system is provided. The system includes a fusion cage configured to receive, allow for flow therethrough, and contain bone graft therein, the fusion cage being expandable, and having at least one opening therethrough; an installer/impactor configured to removably engage the fusion cage and having an installer/impactor handle; an expansion driver configured to insertably engage the installer/impactor and having an expansion driver handle; a cannula configured to fit over the installer/impactor and having a proximate end and a distal end configured to removably engage the fusion cage; and a plunger configured to insertably engage the cannula to move bone graft material through the cannula and outward into a surgical site via the at least one opening in the fusion cage.

In another embodiment, an intervertebral bone graft delivery system is provided. The system includes an expandable fusion cage configured to receive, allow for flow therethrough, and contain bone graft therein, the expandable fusion cage having at least one opening, a rear block aperture and a rear block detent; an installer/impactor configured to removably engage the fusion cage; a cannula configured to fit over the installer/impactor and having a proximate end and a distal end configured to removably engage the fusion cage; and a plunger configured to insertably engage the cannula to move bone graft material through the cannula and outward into a surgical site via the at least one opening. In various embodiments, the installer/impactor includes an installer/impactor tip having at least one installer/impactor ramp, at least one installer/impactor ridge formed on an interior of the at least one ramp and configured to engage the rear block detent, an installer/impactor aperture adjacent to the at least one ridge and configured to engage the rear block aperture, an installer/impactor channel extending from the aperture along a longitudinal axis of the installer/impactor, and an installer/impactor handle disposed on an end opposite the installer/impactor tip.

According to another embodiment, a kit for intervertebral delivery of bone graft is provided, and includes an expandable fusion cage configured to receive, allow for flow therethrough, and contain bone graft therein, the expandable fusion cage having at least one opening; an installer/impactor configured to removably engage the fusion cage and having an installer/impactor handle; an expansion driver configured to insertably engage the installer/impactor and having an expansion driver handle; a cannula configured to fit over the installer/impactor and having a proximate end and a distal end configured to removably engage the fusion cage; a plunger configured to insertably engage the cannula to move bone graft material through the cannula and outward into a surgical site via the at least one opening; and a funnel configured to removably engage the proximate end of the cannula, and to receive bone graft material therein.

According to another embodiment, a method for delivering bone graft material into a surgical site is provided, and includes the steps of engaging an expandable fusion cage configured to receive, allow for flow therethrough, and contain bone graft therein and having at least one opening with an installer/impactor configured to removably engage the fusion cage; positioning the fusion cage within the surgical site using the installer/impactor; inserting an expansion driver through the installer/impactor and engaging the fusion cage with the expansion driver; moving the fusion cage from an unexpanded state to an expanded state using the expansion driver; removing the expansion driver from the fusion cage and installer/impactor; fitting a cannula over the installer/impactor and removably engaging the fusion cage with the cannula; removing the installer/impactor from the fusion cage and the cannula; moving bone graft material through the cannula, into the fusion cage and through the at least one opening into the surgical site; and removing the cannula from the fusion cage.

One having skill in the art will appreciate that the fusion cage may be selectably detachable to the delivery device, for example, by means that mechanically grasp the head, means that attach by vacuum, and means that attach by friction, or other means known to those of skill in the art for attaching the head of an apparatus to the shaft of an apparatus.

The present invention can be used in veterinary conditions, in the thoracic spine or can be used for insertion of a laterally based disk replacement.

In addition, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 4,863,476 to Shepperd; U.S. Pat. No. 6,743,255 to Ferree; U.S. Pat. No. 6,773,460 to Jackson; U.S. Pat. No. 6,835,206 to Jackson; U.S. Pat. No. 6,972,035 to Michelson; U.S. Pat. No. 7,771,473 to Thramann; U.S. Pat. No. 7,850,733 to Baynham; U.S. Pat. No. 8,506,635 to Palmatier; U.S. Pat. No. 8,556,979 to Glerum; U.S. Pat. No. 8,628,576 to Triplett; U.S. Pat. No. 8,709,086 to Glerum; U.S. Pat. No. 8,715,351 to Pinto; U.S. Pat. No. 8,753,347 to McCormack; U.S. Pat. No. 8,753,377 to McCormack; U.S. Design Pat. No. D708,323 to Reyes; U.S. Pat. No. 8,771,360 to Jimenez; U.S. Pat. No. 8,778,025 to Ragab; U.S. Pat. No. 8,778,027 to Medina; U.S. Pat. No. 8,808,383 to Kwak; U.S. Pat. No. 8,814,940 to Curran; U.S. Pat. No. 8,821,396 to Miles; U.S. Patent Application Publication No. 2006/0142858 to Colleran; U.S. Patent Application Publication No. 2008/0086142 to Kohm; U.S. Patent Application Publication No. 20100286779 to Thibodean; U.S. Patent Application Publication No. 20110301712 to Palmatier; U.S. Patent Application Publication No. 20120022603 to Kirschman; U.S. Patent Application Publication No. 20120035729 to Glerum; U.S. Patent Application Publication No. 20120089185 to Gabelberger; U.S. Patent Application Publication No. 20120123546 to Medina; U.S. Patent Application Publication No. 20120197311 to Kirschman; U.S. Patent Application Publication No. 20120215316 to Mohr; U.S. Patent Application Publication No. 20130158664 to Palmatier; U.S. Patent Application Publication No. 20130178940; U.S. Patent Application Publication No. 20140012383 to Triplett; U.S. Patent Application Publication No. 20140156006; U.S. Patent Application Publication No. 20140172103 to O'Neil; U.S. Patent Application Publication No. 20140172106 to To; U.S. Patent Application Publication No. 20140207239 to Barreiro; U.S. Patent Application Publication No. 20140228955 to Weiman; U.S. Patent Application Publication No. 20140236296 to Wagner; U.S. Patent Application Publication No. 20140236297 to Iott; U.S. Patent Application Publication No. 20140236298 to Pinto.

Furthermore, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 7,803,159 to Perez-Cruet et al.; U.S. Pat. No. 8,852,282 to Farley et al.; U.S. Pat. No. 8,858,598 to Seifert et al.; U.S. Pat. No. D714,933 to Kawamura; U.S. Pat. No. 8,795,366 to Varela; U.S. Pat. No. 8,852,244 to Simonson; U.S. Patent Application Publication No. 2012/0158146 to Glerum et al.; U.S. Pat. No. 8,852,242 to Morgenstern Lopez et al.; U.S. Pat. No. 8,852,281 to Phelps; U.S. Pat. No. 8,840,668 to Donahoe et al.; U.S. Pat. No. 8,840,622 to Vellido et al.; U.S. Patent Application Publication No. 20140257405; U.S. Patent Application Publication No. 20140257490 to Himmelberger et al.; U.S. Pat. No. 8,828,019 to Raymond et al.; U.S. Patent Application Publication No. 20140288652 to Boehm et al.; U.S. Patent Application Publication No. 20140287055 to Kunjachan; U.S. Patent Application Publication No. 20140276896 to Harper; U.S. Patent Application Publication No. 20140277497 to Bennett et al.; U.S. Patent Application Publication No. 20120029635 to Schoenhoeffer et al.; U.S. Patent Application Publication No. 20140303675 to Mishra; U.S. Patent Application Publication No. 20140303731 to Glerum; U.S. Patent Application Publication No. 20140303732 to Rhoda et al.; U.S. Pat. No. 8,852,279 to Weiman; PCT WO2012031267 to Weiman; U.S. Pat. No. 8,845,731 to Weiman; U.S. Pat. No. 8,845,732 to Weiman; U.S. Pat. No. 8,845,734 to Weiman; U.S. Patent Application Publication No. 20140296985 to Balasubramanian et al.; U.S. Patent Application Publication No. 20140309268 to Arnou; U.S. Patent Application Publication No. 20140309548 to Merz et al.; U.S. Patent Application Publication No. 20140309697 to Iott et al.; U.S. Patent Application Publication No. 20140309714 to Mercanzini et al.; U.S. Pat. No. 8,282,683 to McLaughlin et al.; U.S. Pat. No. 8,591,585 to McLaughlin et al; U.S. Pat. No. 8,394,129 to Morgenstern Lopez et al.; U.S. Patent Application Publication No. 20110208226 to Fatone et al.; U.S. Patent Application Publication No. 20100114147 to Biyani; U.S. Patent Application Publication No. 20110144687 to Kleiner; U.S. Pat. No. 8,852,243 to Morgenstern Lopez et al.; U.S. Pat. No. 8,597,333 to Morgenstern Lopez et al.; U.S. Pat. No.

8,518,087 to Lopez et al.; U.S. Patent Application Publication No. 20120071981 to Farley et al.; U.S. Patent Application Publication No. 20130006366 to Farley et al.; U.S. Patent Application Publication No. 20120065613 to Pepper et al.; U.S. Patent Application Publication No. 20130006365 to Pepper et al.; U.S. Patent Application Publication No. 20110257478 to Kleiner et al.; U.S. Patent Application Publication No. 20090182429 to Humphreys et al.; U.S. Patent Application Publication No. 20050118550 to Turri; U.S. Patent Application Publication No. 20090292361 to Lopez; U.S. Patent Application Publication No. 20110054538 to Zehavi et al.; U.S. Patent Application Publication No. 20050080443 to Fallin et al.; U.S. Pat. No. 8,778,025 to Ragab et al.; U.S. Pat. No. 8,628,576 to Triplett et al; U.S. Pat. No. 8,808,304 to Weiman; U.S. Pat. No. 8,828,019 to Raymond; and U.S. Pat. No. 9,949,841 to Glerum et al.

One of ordinary skill in the art will appreciate that embodiments of the present disclosure may have various sizes. The sizes of the various elements of embodiments of the present disclosure may be sized based on various factors including, for example, the anatomy of the implant patient, the person or other device operating the apparatus, the implant location, physical features of the implant including, for example, with, length and thickness, and the size of operating site or the size of the surgical tools being used with the device.

One or ordinary skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, rubber, latex, synthetic rubber, and other fiber-encased resinous materials, synthetic materials, polymers, and natural materials. In another embodiment, some or all elements of the device, or portions of some or all of the elements, are luminescent. Also, in another embodiment, some or all elements of the device, or portions of some or all of the elements, include lighting elements.

In one embodiment of the fusion cage, the fusion cage comprises a polymer, such as PEEK, titanium and composite materials.

One of ordinary skill in the art will appreciate that embodiments of the present disclosure may be controlled by means other than manual manipulation. Embodiments of the present disclosure may be designed and shaped such that the apparatus may be controlled, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

Embodiments of the present disclosure present several advantages over the prior art including, for example, the speed of the procedure, the minimally invasive aspect of the procedure, the ability to introduce implant material to an implant site with minimal risk and damage to the surrounding tissue, the lower risk of infection, more optimally placed implant material, a more stable delivery device which is designed to reduce the likelihood of the implant material becoming dislodged prior to fixation, and fewer tools in a surgical site due to the integration of several components required to provide bone graft to a bone graft receiving area. Further, the lower profile of the device allows improved viewing of the surgical area, and use of a reduced set and size of elements therein provides a less expensive device.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

FIGS. 9A and 9B are illustrations of a tip of an embodiment of a disc space and/or end plate preparation tool in "bent" and "straight" configurations, respectively;

FIGS. 10A, 10B and 10C are illustrations of a flat Nitinol or other shape-metal portion of a tip of an embodiment of a disc space and/or end plate preparation tool, and rings mating therewith;

REFERENCE NO. COMPONENT

Figure 1A:
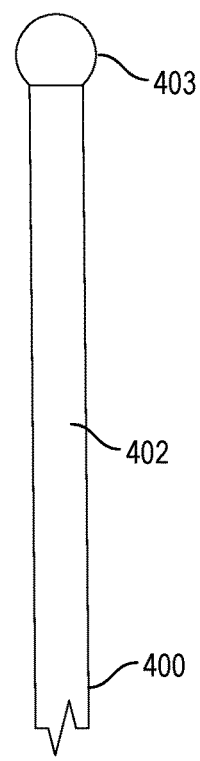
FIGS. 1A and 1B are illustrations of a plurality of sharp-edged blades of an embodiment of a disc space preparation tool in a first configuration and a second configuration, respectively.

2 Cannula
3 Cannula first exterior surface
4 Opening (of Cannula)
6 First end (of Cannula)
8 Second end (of Cannula)
12 Plunger
30 Funnel
60 Fusion Cage
237 Rear block aperture
239 Rear block detent
250 Installer/Impactor
252 Installer/Impactor Tip
253 Installer/Impactor Aperture
254 Installer/Impactor Ridge
255 Installer/Impactor Channel
256 Installer/Impactor Ramp
258 Installer/Impactor Handle
260 Expansion Driver 268 Expansion Driver Handle
270 Removal Pliers
280 Cannula External Ramp
282 Cannula Notch
284 Cannula Slot
285 Cannula Slot Aperture
300 Insertion Tool
301 Slidable Rectangular Shaft
302 Window
303 Wingnut
304 Tab(s)
305 Fusion Cage
306 Trigger
307 Insertion Plunger
308 Handle
309 Ratcheting Screwdriver Handle
310 Quick Connect Device
311 Screwdriver Shaft
313 Bone Graft Application Funnel
314 Bone Graft Plunger
315 Expansion Site
316 Plate
317 Groove, slot, or track
318 Tab
319 Tab attachment
400 Disc space preparation tool
401 Sharp-edged blade
402 Cannula
403 Stop or other terminal element
404 Grip
405 Plastic ring
406 User-operable trigger
407 "Spine"
408 Tip
409 Tip attachment
410 Control knob
411 Flat portion of Nitinol blade
412 Nitinol blade
413 Bore or thru-hole
414 Rotational bias feature
415 Window
416 Handle
417 Lock-and-key feature
418 Threaded or toothed shaft
419 Threaded or toothed insert
420 Pin It should be understood that the drawings are not necessarily to scale. In certain instances, details that are not necessary for an understanding of the invention or that render other details difficult to perceive may have been omitted from these drawings. It should be understood, of course, that the invention is not limited to the particular embodiments illustrated in the drawings.

DETAILED DESCRIPTION

As used herein, the term "whisk structure" refers to a plurality of loops of wire or other substantially rigid material, each of the loops bowing outward from, and being affixed at each end to, a handle, shaft, cannula, or other connective element. Collectively, the loops of material of a whisk structure define and surround a void space, and the whisk structure may be especially suitable for scraping, aggregating, or collecting a surrounding material.

In one embodiment of a disc space preparation tool according to the present invention, the disc space preparation tool comprises a cylindrical cannula, a grip, and a plurality of sharp-edged blades. Preferably, the grip is a T-type grip, but other types of grip, including by way of non-limiting example a pistol-type grip and a handlebar-type grip, are contemplated and are within the scope of the invention. Preferably, the plurality of sharp-edged blades comprises four sharp-edged blades, but any number of blades, including two, three, five, or more, may be suitable for a desired application and is within the scope of the invention.

The sharp-edged blades may be made of any suitable material, as will be understood by those of ordinary skill in the art, but may preferably be made of a nickel-titanium alloy, also known as Nitinol. Nitinol exhibits various advantageous mechanical properties, including shape memory and superelasticity, and is biocompatible and therefore already widely used in surgical tools and other medical devices.

The sharp-edged blades may be open at a distal end, or they may loop back and be affixed to the cannula at both ends, thereby providing a whisk structure. In some applications, particularly where preparation of the intervertebral disk space requires excavation and removal of tissue or other material, the whisk structure may be advantageous.

The disc space preparation tool of the present invention may be an angled tool, i.e. the grip and the cylindrical cannula, and/or the cylindrical cannula and the plurality of sharp-edged blades, may be offset from each other by an angle such that they do not lie in the same plane. The angle between the grip and the cylindrical cannula, and/or between the cylindrical cannula and the plurality of sharp-edged blades may, in embodiments, be any whole number of degrees that is no more than about 45 degrees, preferably between about 3 degrees and about 25 degrees, and more preferably between about 5 degrees and about 15 degrees.

The sharp-edged blades of disc space preparation tools of the present invention may be reconfigurable. By way of non-limiting example, the sharp-edged blades may be substantially linearly shaped in the first configuration, but have an arcuate shape in the second configuration. As a result, a void space defined and surrounded by the plurality of sharp-edged blades may be approximately cylindrical in the first configuration, but "rounder," i.e. spheroid or approximately spheroid, in the second configuration. A rounder void space may be desirable in many applications, including, by way of non-limiting example, where it is desirable to expand the intervertebral disc space during a spinal surgery.

The reconfiguration of the plurality of sharp-edged blades may be accomplished by any of several means, but will most advantageously be achieved by a user imparting a force on the grip. By way of non-limiting example, a user may impart a pulling force to the grip to maneuver the disc space preparation tool in the first configuration, and then a pushing force to reconfigure the plurality of sharp-edged blades into the second configuration. In other embodiments, the user may impart a rotational force to the grip to reconfigure the plurality of sharp-edged blades into the second configuration. The reconfiguration force imparted on the grip by the user may be communicated to the plurality of sharp-edged by the cylindrical cannula itself, or by a shaft or other element disposed within the cylindrical cannula. The sharp-edged blades, or a proximal portion thereof, may be retracted into or disposed within an interior of the cylindrical cannula when the sharp-edged blades are in the first configuration.

The disc space preparation tool may comprise additional features. By way of non-limiting example, a spring may be interconnected to a proximal end of the plurality of sharp-edged blades and permit displacement of the plurality of sharp-edged blades relative to an axis of the cylindrical cannula. Where the disc space preparation tool comprises this spring, it may, but need not, further comprise a hollow connective element and one or more stays, interconnected to the grip and permitting the user to selectively move the plurality of sharp-edged blades in a desired direction.

One of ordinary skill in the art will recognize that prior to insertion of an implantable cage and/or other procedures to be performed within the workspace, it is necessary or desirable to remove various tissue and debris from a workspace and a vertebral end plate. Accordingly, in various embodiments, the present invention contemplates a plurality of sharp-edged blades, which may but need not form a whisk structure, adapted for removing debris from and cleaning an intervertebral endplate.

In various embodiments, the present invention comprises features and devices for physically sealing, closing, or otherwise containing receiving apertures. For example, receiving apertures or fenestrations which are generally open during spinal procedures may be selectively sealed or closed by a user through the use of features disposed at a proximal end of the device.

A variety of known vacuum pumps and devices may be utilized in combination with aspects of the present invention. By way of example, U.S. Pat. No. 5,282,744 to Meyer, U.S. Pat. No. 4,580,978 to Motola et al., U.S. Pat. No. 4,991,570 to Bullard, U.S. Pat. No. 5,311,640 to Holland, and U.S. Patent Application Publication No. 2007/0172790 to Doucette, Jr. et al., which are incorporated by reference in their entireties herein, generally relate to the field of dentistry. However, various features and aspects described in these references may be incorporated into aspects of the present invention.

In various embodiments, a positive pressure may be applied to a disc space through portions of a disc space preparation tool. For example, air or other gases and/or fluids may be provided to a disc space to blast or clear an area to be cleaned. U.S. Pat. No. 6,004,191 to Schur et al., U.S. Pat. No. 4,430,062 to Henrichsen et al., U.S. Pat. No. 4,877,399, which are incorporated by reference herein in their entireties relate to various devices and methods for delivering a volume of air or fluid to a desired location. In various embodiments, the present invention comprises delivering forced or pressurized air, gas, fluids, and various combinations thereof to a disc space and a distal end of a disc space preparation tool. For example, ambient air, inert gases, oxygen, water, saline, and various combinations thereof may be directed to a disc space through features of the present invention (e.g. channels housed within a disc space preparation tool). One of skill in the art will recognize that such features may direct such substances to a portion of a disc space (e.g. a disc end plate) and/or to a portion of the tool which has become contaminated with various fluid, tissue, debris, etc. (e.g. a distal end).

One of ordinary skill in the art will appreciate that embodiments of the present disclosure may have various sizes. The sizes of the various elements of embodiments of the present disclosure may be sized based on various factors including, for example, the anatomy of the patient, the person or other device operating the apparatus, the surgical location, physical features of the implant including, for example, width, length and thickness, and the size of other surgical tool(s) being used.

Grips, cylindrical cannulas, and/or sharp-edged blades of embodiments of the present disclosure may be constructed of materials known to provide, or predictably manufactured to provide the various aspects of the present disclosure. These materials may include, for example, nickel-titanium alloy, stainless steel, titanium alloy, aluminum alloy, chromium alloy, and other metals or metal alloys. These materials may also include, for example, PEEK, carbon fiber, ABS plastic, polyurethane, rubber, latex, synthetic rubber, and other fiber-encased resinous materials, synthetic materials, polymers, and natural materials, and any kind of material suitable for surgical use, such as aluminum, iron, titanium, steel, medical grade plastic, surgical stainless steel of the general alloy type of iron, carbon, chromium (12-20%), molybdenum (0.2-3%), and nickel (8-12%); martensitic steel; 316L or 316LVM austenitic steel; and/or 316 surgical steel. In particular, it may be desirable to form the cylindrical cannula of a flexible material such that the cylindrical cannula is resiliently deformable.

In various embodiments, suction may be applied to a device through a hollow cylindrical cannula or hollow portion of a cylindrical cannula. A vacuum pressure may apply one or more forces capable of withdrawing material from a disc space and/or biasing material that has been dislodged by portions of the tool against or toward a proximal portion of the tool. As used herein, a proximal portion will generally be understood to mean the portion of the tool proximal to a user/surgeon in operation.

Disc space preparation tools according to embodiments of the present invention may, but need not, be connected to a conduit or tubing adapted for transmitting a gas or fluid from a pump and/or gas or fluid source. A gas or fluid source may comprise any number of known receptacles and sources of fluid including, but not limited to, one or more storage tanks containing various types and quantities of fluid or gas (e.g. medical grade gas or fluid). In various embodiments, a pump is provided for transmitting a gas or fluid to portions of a disc space preparation device 8 at a given pressure. In various embodiments, a user-operable control device (e.g. a trigger mechanism) is provided for selectively directing air to portions of a disc space preparation tool and a disc space.

Figure 1B:
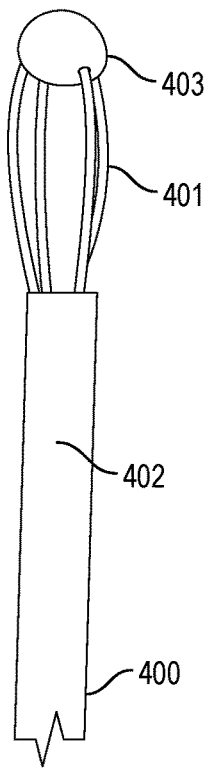

FIGS. 1A and 1B are illustrations of one embodiment of the plurality of sharp-edged blades 401 of a disc space preparation tool 400 in a first configuration and a second configuration, respectively. In FIG. 1A, the sharp-edged blades 401 in the first configuration are in a compressed or retracted state and are housed entirely within the distal end of the cannula 402; in this embodiment, a stop or other connective or terminal element 403, to which each of the sharp-edged blades 401 is interconnected, is provided to maintain the plurality of sharp-edged blades 401 inside the cannula 402 and prevent them from extending beyond the cannula 402 until a user-operable trigger 406 is actuated. In FIG. 1B, a user has actuated the user-operable trigger 406 of the disc space preparation tool 400, and the sharp-edged blades 401 in the second configuration are in an expanded or extended state and extend beyond the distal end of the cannula 402 and form a whisk structure. As illustrated, the sharp-edged blades 401 have an arcuate shape in the second configuration. As a result, a void space defined and surrounded by the plurality of sharp-edged blades 401 is spheroid, approximately spheroid, oblate spheroid, or prolate spheroid in the second configuration. A rounder void space may be desirable in many applications, including, by way of non-limiting example, where it is desirable to expand the intervertebral disc space during a spinal surgery.

Figure 2:
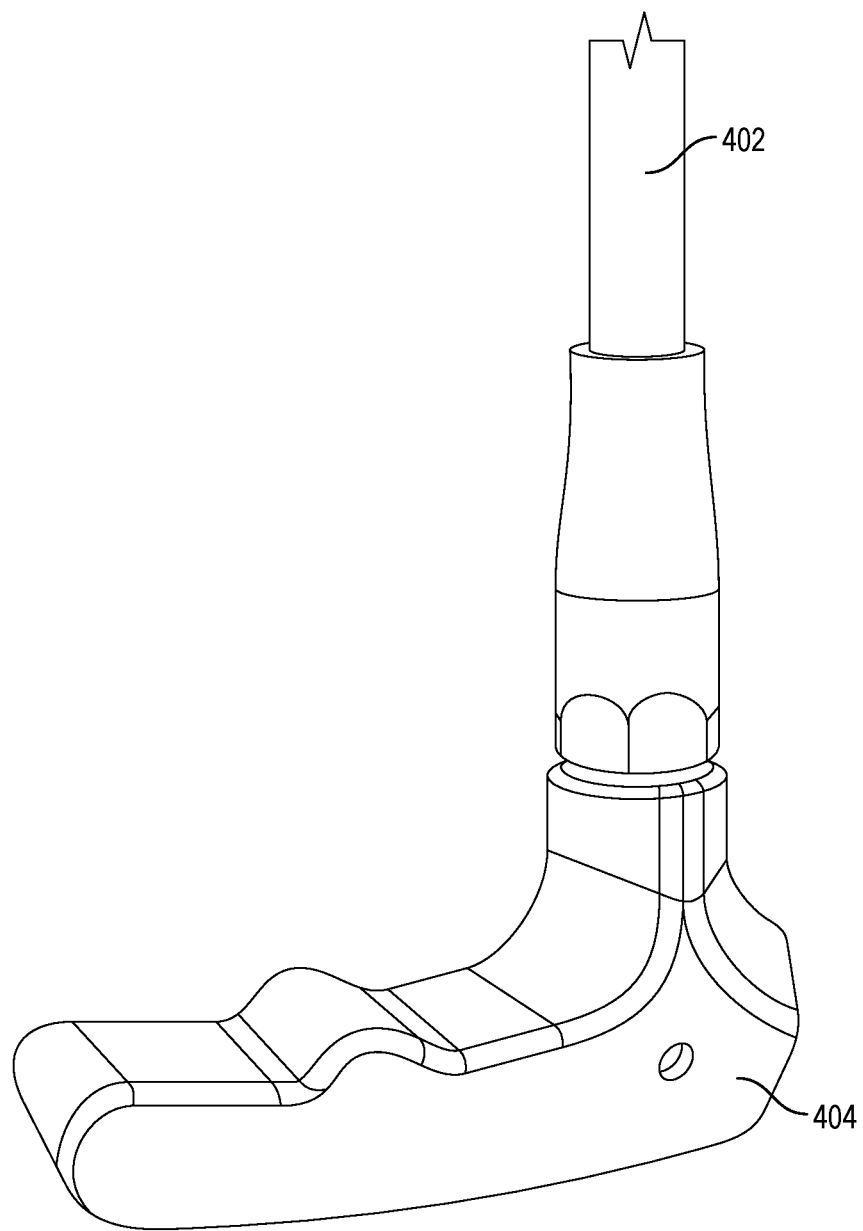
FIG. 2 is an illustration of a pistol-type grip in an embodiment of a disc space preparation tool.

FIG. 2 illustrates a pistol-type grip 404 for use in the positioning handle of a disc space preparation tool 400 according to an embodiment of the present invention. This grip 404 is adapted such that a user may comfortably and precisely operate the disc space preparation tool 400 with one hand, if desired.

In embodiments of a disc space preparation tool according to the present invention, the plurality of sharp-edged blades 401 may be interconnected to the cannula 402 by a section of rigid connecting material taking the form of a coil or "slinky"-like shape, hereinafter referred to as a coil. When not reinforced by any other element, the coil permits the plurality of sharp-edged blades 401 to extend outwardly from the distal end of the cannula 402 at an angle relative to a longitudinal axis of the cannula 402; a user of the disc space preparation tool 400 can therefore maneuver the plurality of sharp-edged blades 401 at least semi-independently of the cannula 402 by imparting a force on the coil in a desired direction. The coil may permit the plurality of sharp-edged blades 401 to be displaced in any direction relative to the longitudinal axis of the cannula 402, including upwardly, downwardly, to the left, and/or to the right. In such embodiments, the cannula 402 may permit insertion of a linear or curved stay, made of a stiff metal or any other suitable material, that reinforces the coil and forces it into a desired position so that it no longer permits displacement of the plurality of sharp-edged blades 401. The stay may be straight, such that the plurality of sharp-edged blades 401 is in line with the longitudinal axis of the cannula 402, or it may be curved, such that the coil is forced to displace the plurality of sharp-edged blades 401 at an angle relative to the longitudinal axis of the cannula 402; in embodiments, the angle between the plurality of sharp-edged blades 401 and the cannula 402 when the coil is reinforced by the stay may be any suitable angle, including any whole number of degrees up to and including 180°, and preferably and most commonly will be between about 10° and about 20°. The use of the flexible coil and stay allows a surgeon or other user to clear material from an intervertebral disc space both directly in the path of the disc space preparation tool 400, and at the margins of the disc space.

Figure 3:
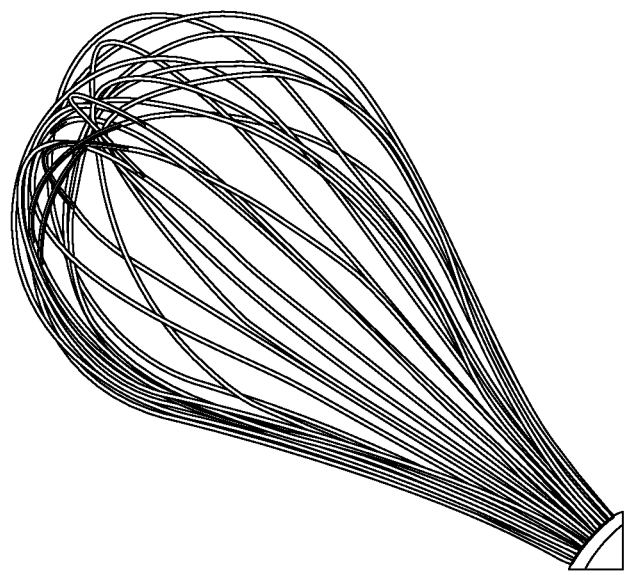
FIG. 3 is an illustration of a balloon whisk structure for the plurality of blades of an embodiment of a disc space preparation tool.
Figure 4:
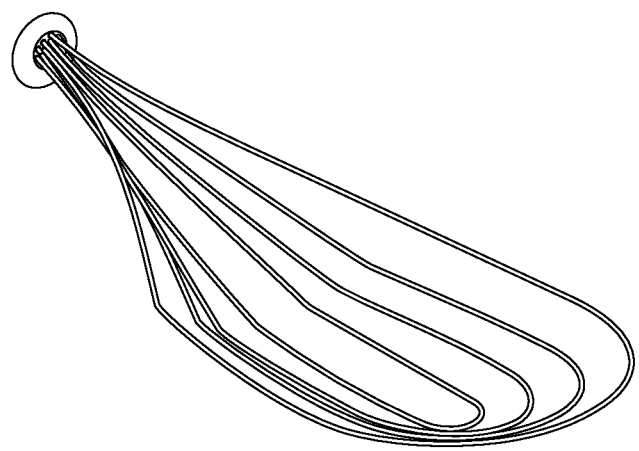
FIG. 4 is an illustration of a flat whisk structure for the plurality of blades of an embodiment of a disc space preparation tool.
Figure 5:
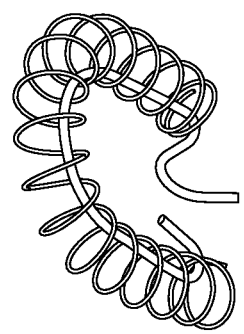
FIG. 5 is an illustration of a spiral whisk structure for the plurality of blades of an embodiment of a disc space preparation tool.
Figure 6:
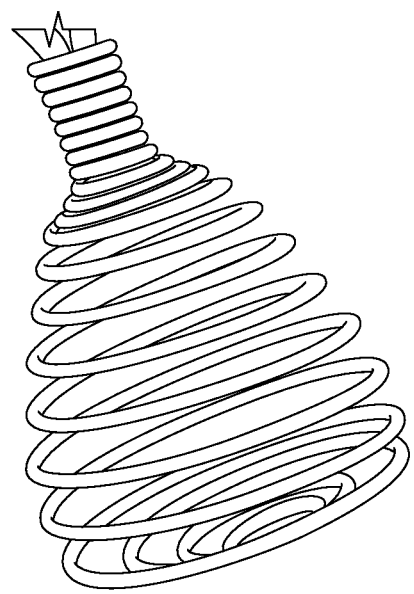
FIG. 6 is an illustration of a coil whisk structure for the plurality of blades of an embodiment of a disc space preparation tool.
Figure 7:
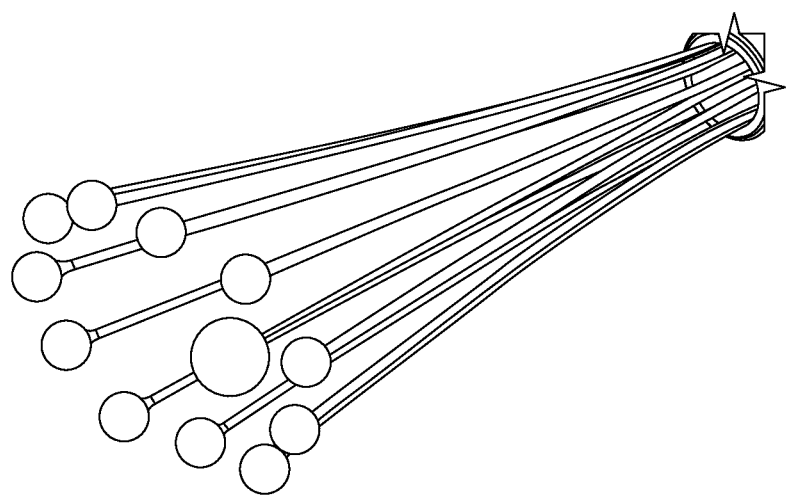
FIG. 7 is an illustration of a ball whisk structure for the plurality of blades of an embodiment of a disc space preparation tool.
Figure 8:
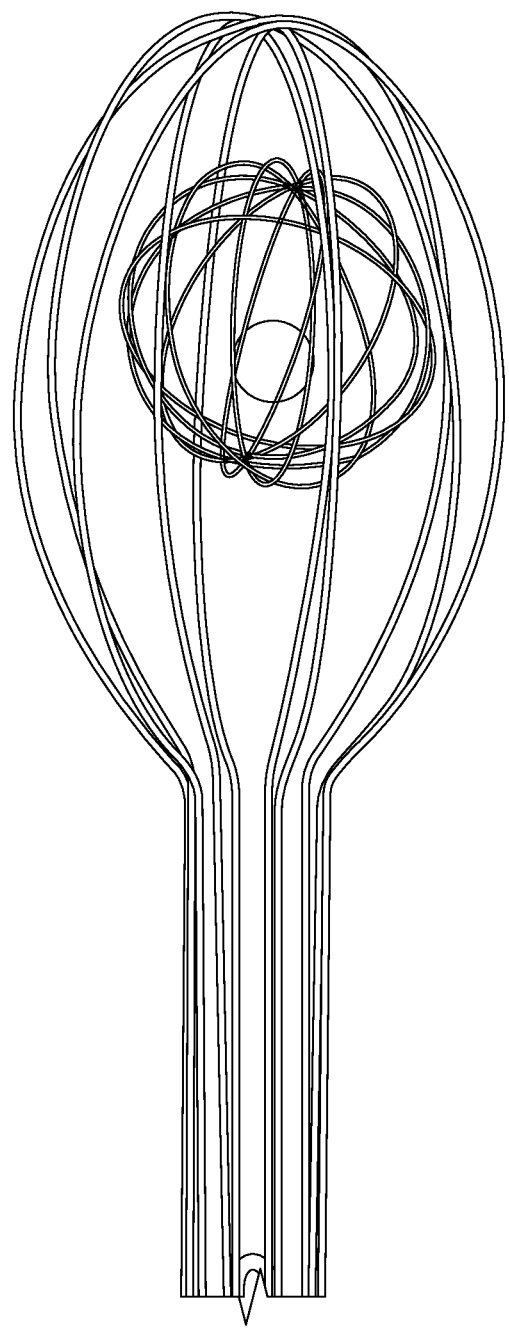
FIG. 8 is an illustration of a cage whisk structure for the plurality of blades of an embodiment of a disc space preparation tool.

The plurality of sharp-edged 401 blades of the present invention may, but need not, form a whisk structure, and where the plurality of sharp-edged blades 401 does form a whisk structure it may, but need not, form a French whisk structure as illustrated in FIG. 1B. FIGS. 3-8 illustrate alternative embodiments of whisk structures that may be suitable for use in the present invention. FIG. 3 illustrates a balloon whisk structure, in which the interior void space formed by the plurality of sharp-edged blades has a rounder, wider "teardrop" shape. FIG. 4 illustrates a flat whisk structure, in which the sharp-edged blades are arranged in a flat successive pattern. FIG. 5 illustrates a spiral whisk structure, in which one or more sharp-edged blades are coiled around a single main sharp-edged blade. FIG. 6 illustrates a coil whisk structure, in which a single sharp-edged blade is spiraled into a balloon shape. FIG. 7 illustrates a ball whisk structure, in which each of the sharp-edged blades does not form a closed loop but instead extends linearly away from the distal end of the cannula and terminates in a ball, stop, or other terminal element. FIG. 8 illustrates a cage whisk structure, in which the plurality of sharp-edged blades forms a balloon whisk structure, disposed inside of which is a cage containing a ball or other spherical or spheroid element.

End plate and disc space preparation tools 400 according to the present invention may be hygienic, disposable, and inexpensive. In certain embodiments, such tools may be generally characterized by a shaft and a head comprising a plurality of flexible blades 401, interconnected by a spring, coil, or similar mechanism. The spring or coil allows the head of the tool 400 to be rotatably articulated relative to a longitudinal axis of the shaft of the tool 400. The tool 400 may also comprise a straight and/or curved stay, which is stiff but flexible enough to fit over the shaft and spring/coil and fix the head at a desired angle relative to the longitudinal axis. In this way the head is selectively "steerable" within the disc space.

The head may comprise a plurality of expandable Nitinol blades, may reversibly expand and lock, and is adapted to trap debris contained within the disc space. The head, and the disc space preparation tool 400 as a whole, may also be adapted to interconnect with and/or operate in conjunction with a suction means for removing debris from the intervertebral space via suction.

Figure 9A:
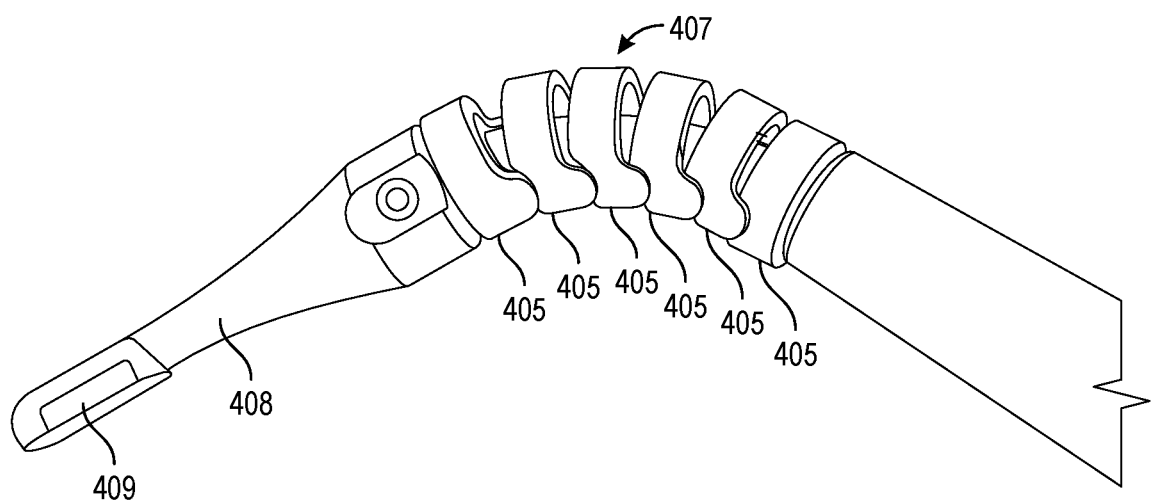
Figure 10C:
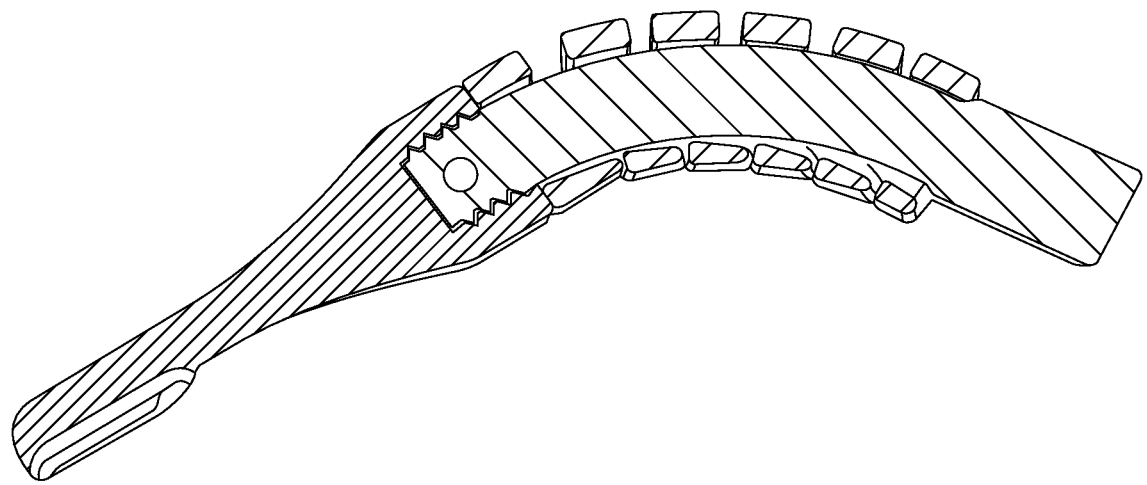

Additionally, the disc space preparation tool 400 may, in embodiments, comprise a series of plastic rings 405 around a Nitinol wire, such that the plastic rings form a "spine" 407 and are pre-bent to a desired angle, e.g. 60 degrees, relative to a longitudinal axis of the tool 400, as illustrated in FIG. 9A. A tip 408 of the tool 400, which may comprise any one or more types of tip attachment 409, is applied to a handle, allowing the tip 408 to be straightened by tightening a control knob 410 that draws a shaft of the tip 408 toward the handle and locks the position of the tip 408 via the plastic rings 405.

Once the device 400 is inserted into the disc space, the control knob 410 can be gradually released, allowing the tip 408 to return to its pre-bent angle, as illustrated in FIG. 9B; thus, unlike previous disc space preparation tools, embodiments of the present invention allow for in situ alteration of the shape of the disc space preparation tool 400, entrance of a tool 400 which would otherwise not fit within an exposure portal to be placed in the disc space, and (most importantly) debridement of disc material on a side contralateral to a side of the annulotomy.

Figure 12A:
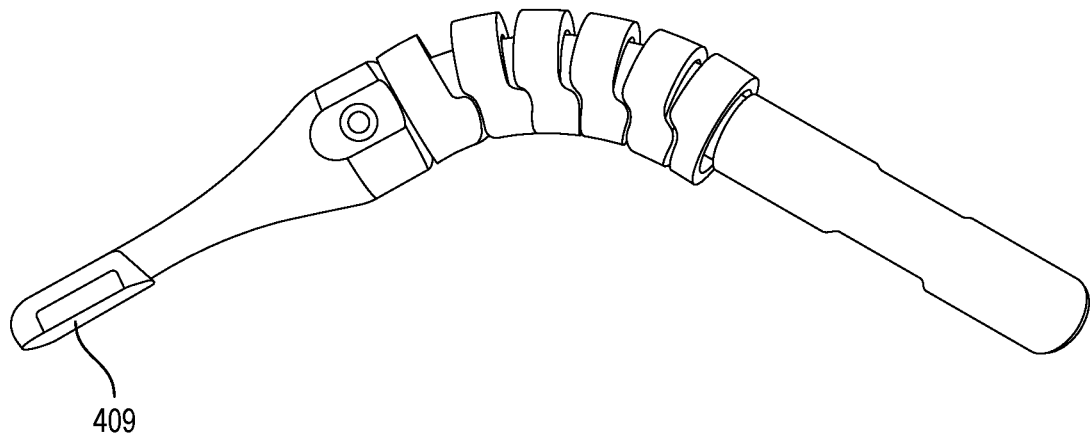
FIGS. 12A, 12B, 12C, and 12D are illustrations of a curette tip attachment, an Epstein tip attachment, a rasp tip attachment, and a ring curette tip attachment, respectively, for an embodiment of a disc space and/or end plate preparation tool.
Figure 12B:
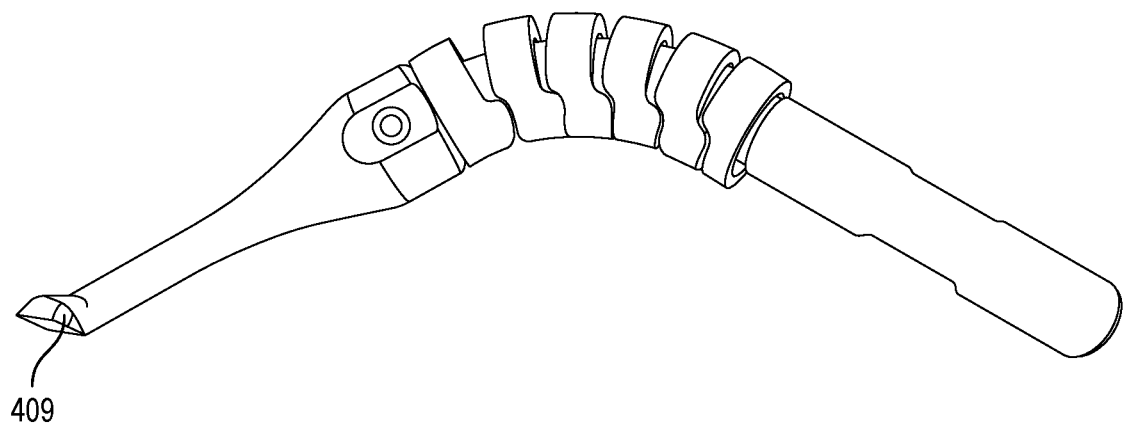
Figure 12C:
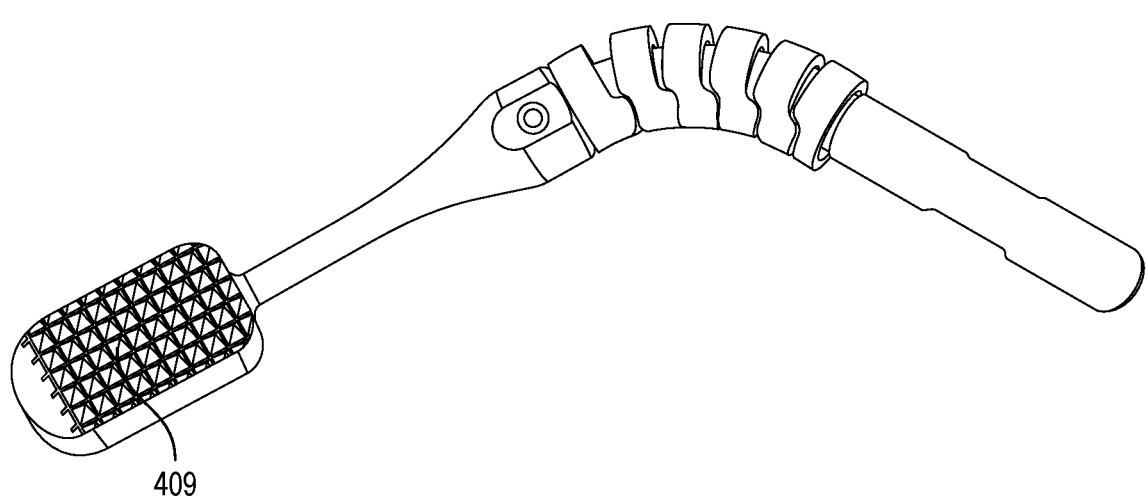
Figure 12D:
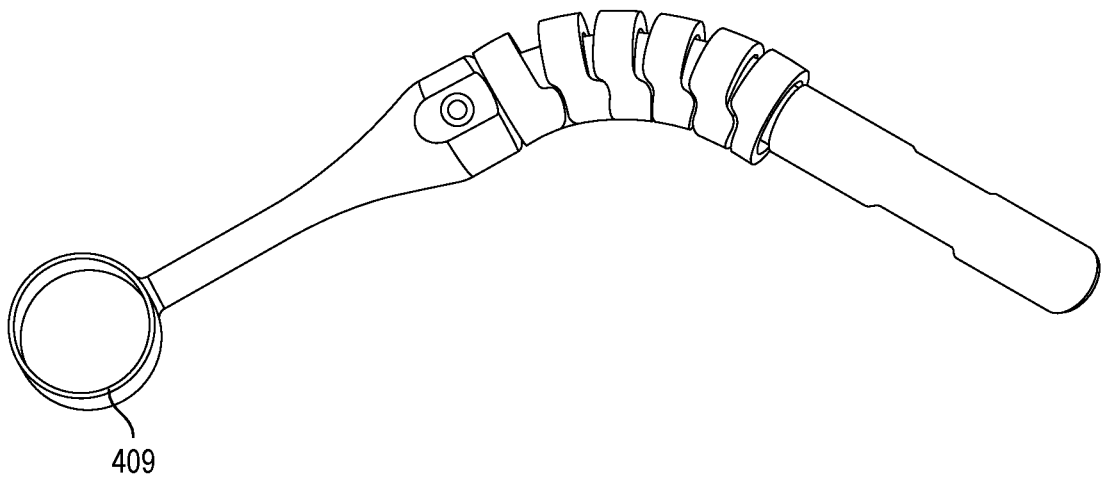

The tips 408 of the disc space preparation tools 400 of the present invention, in various embodiments, may be disposable, and may comprise any one or more of several known tip attachments 409. Non-limiting examples of tip attachments 409 that may be provided with disc space preparation tools of the present invention are #3 curettes (FIGS. 9A, 9B, and 12A), #5 curettes, Epstein curettes (FIG. 12B), ring curettes (FIG. 12D), flat rasps (FIG. 12C), curved rasps, square-ended periosteal elevators, and round-ended periosteal elevators, each of which may be provided in any suitable size.

Figure 11A:
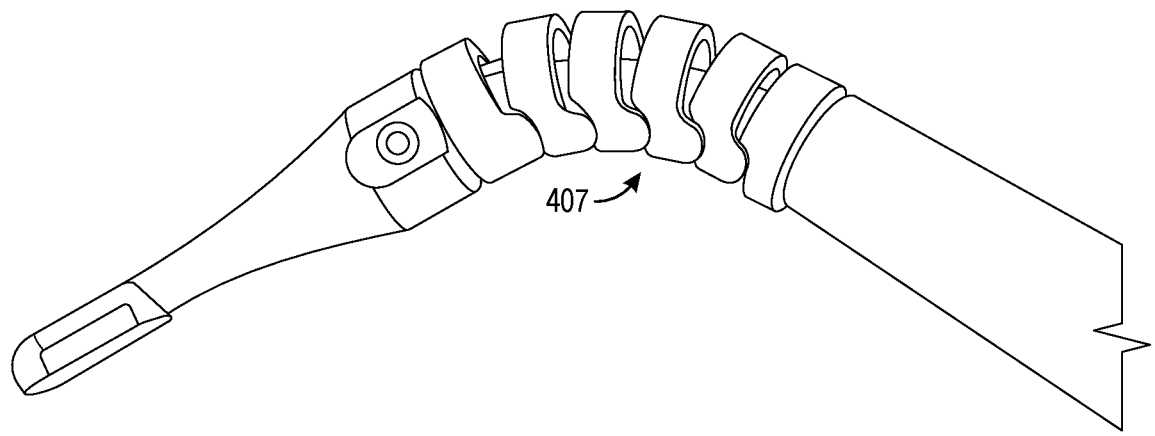
FIG. 11A is an illustration of a tip of an embodiment of a disc space and/or end plate preparation tool that has been "pre-bent" via a "spine" and/or rotational bias feature.
Figure 11B:
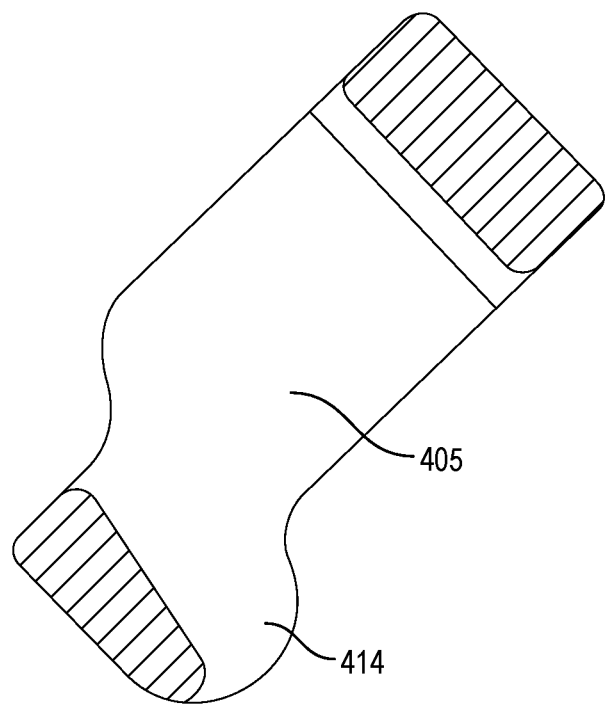
FIG. 11B is another illustration of the rotational bias feature illustrated in FIG. 11A.
Figure 11C:
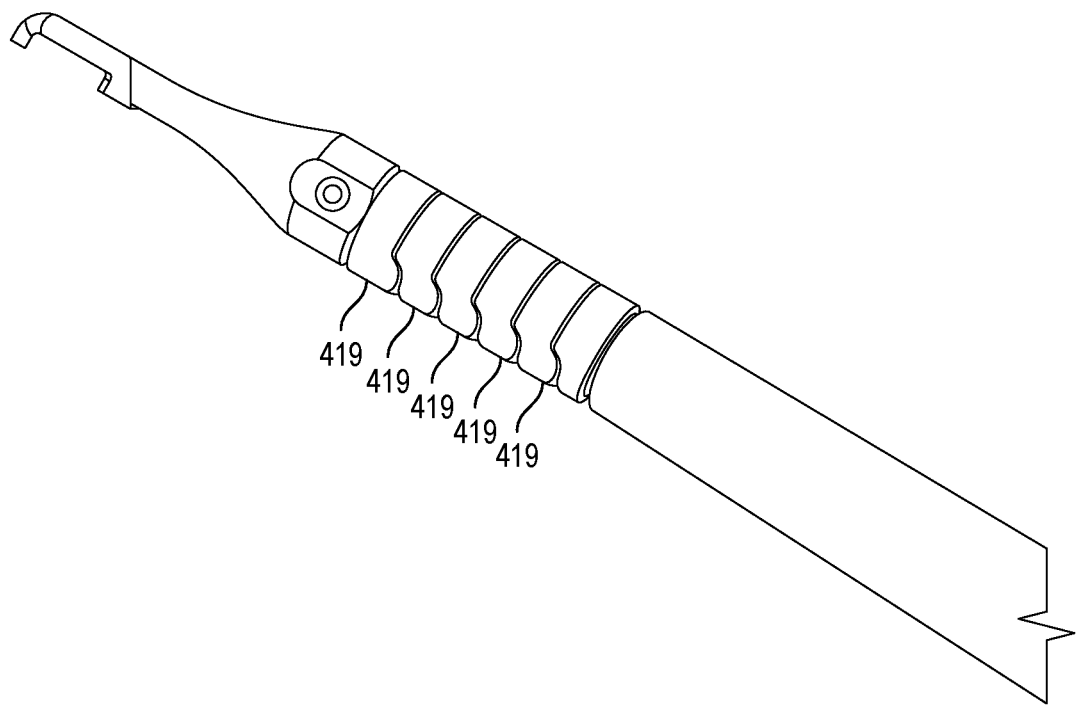
FIG. 11C is an illustration of the embodiment illustrated in FIG. 11A, in which the rings of the "spine" have been interlocked to straighten the tip of the tool.

As illustrated in FIGS. 10A through 11C, rings 405 making up the "spine" 407 of the disc space preparation tool 400 allow for biasing of the tip 408 and therefore a mechanical advantage during rotation of the tool 400 due to the shape of the ring 405. Particularly, in certain embodiments, a flat portion 411 of a Nitinol blade 412 may mate with a flat portion of a bore or thru-hole 413 in each ring 405, thus preventing rotation of the ring 405 with respect to the Nitinol blade 412. As depicted in FIGS. 11A through 11C, one or more rings 405 (shown in a cut/linear form in FIG. 11B) may comprise a rotational bias feature 414 such as a tab or protrusion, such that the rings interlock and prevent movement when the "spine" 407 is in a bent configuration.

Figure 13:
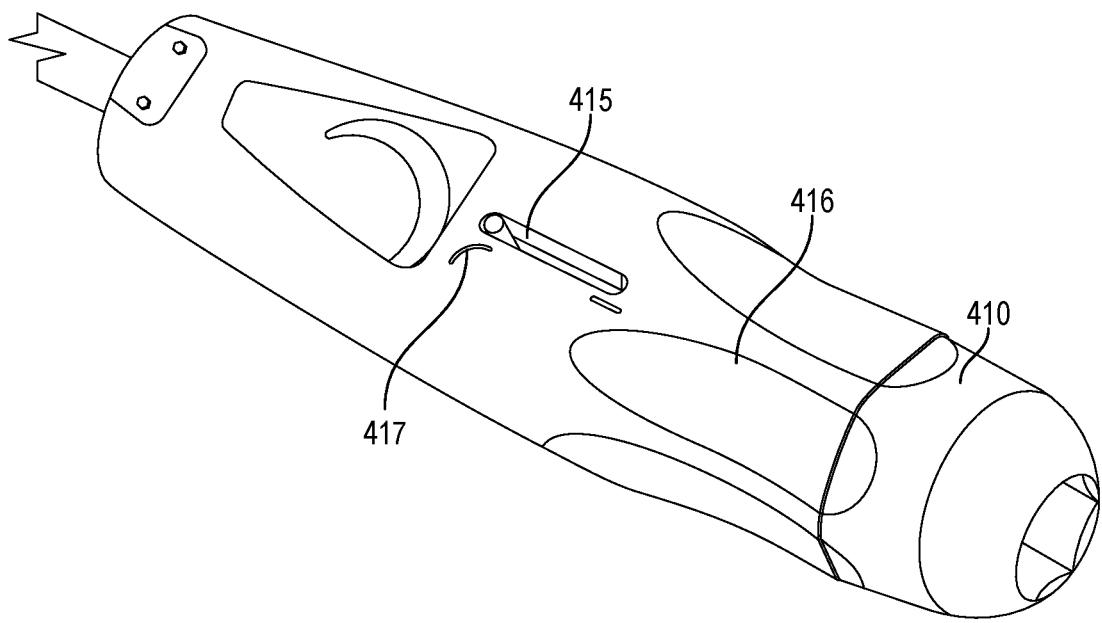
FIG. 13 is an illustration of a handle of an embodiment of a disc space and/or end plate preparation tool, having a window and a lock-and-key feature.

In embodiments of disc space preparation tools 400 of the present invention, as illustrated in FIG. 13, a window 415 in a handle 416 of the tool 400 may allow visualization of the degree of curvature of the tip 408 while the control knob 410 is rotated. This feature may be provided on each of two opposing sides of the handle 416 to permit a surgeon to visualize the rotation regardless of which side of a patient's body the surgeon is working on. As illustrated, the disc space preparation tool 400 may also include a lock-and-key feature 417, by which a key must be inserted to exchange tip attachments 409, thereby preventing accidental release of the tip attachment 409 within the disc space.

Figure 14A:
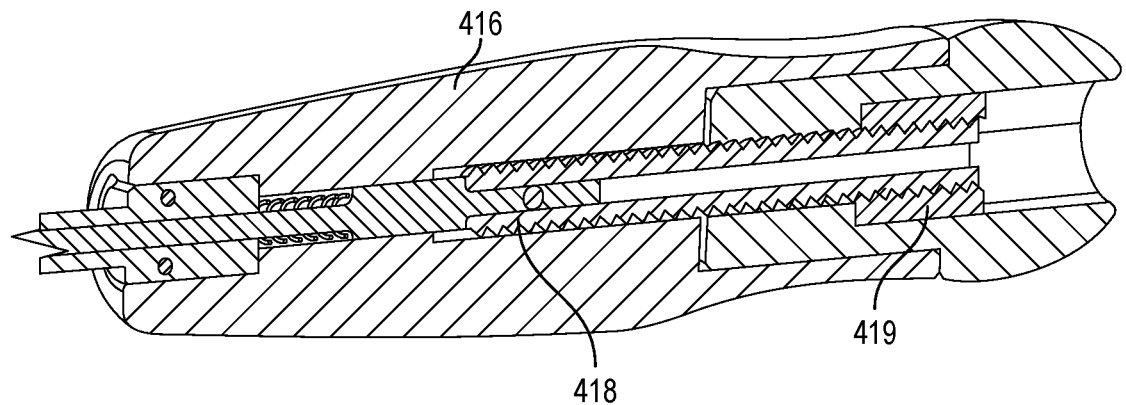
FIG. 14A is an illustration of a threaded or toothed shaft and threaded or toothed insert of an embodiment of a disc space and/or end plate preparation tool.
Figure 14B:
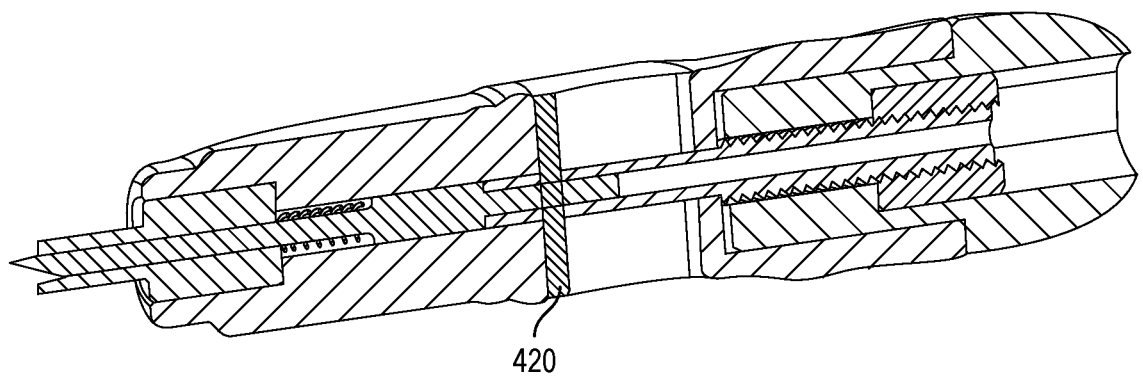
FIG. 14B is an illustration of a pin within the shaft illustrated in FIG. 14A.

In embodiments of disc space preparation tools 400 of the present invention, as illustrated in FIG. 14A, a threaded or toothed shaft 418 may engage with a threaded or toothed insert 419 to provide axial movement, causing the "spine" 407 to straighten. As illustrated in FIG. 14B, a pin 420 within the handle 416 may act as a "keystone" to hold the device together and/or to provide a visual indicator of the tip 408 position (i.e. curved or straight). Flat portions on the threaded shaft 418 may engage with flat portions of the handle 416 to prevent rotation of the shaft 418 with respect to the handle body 416.

Figure 15A:
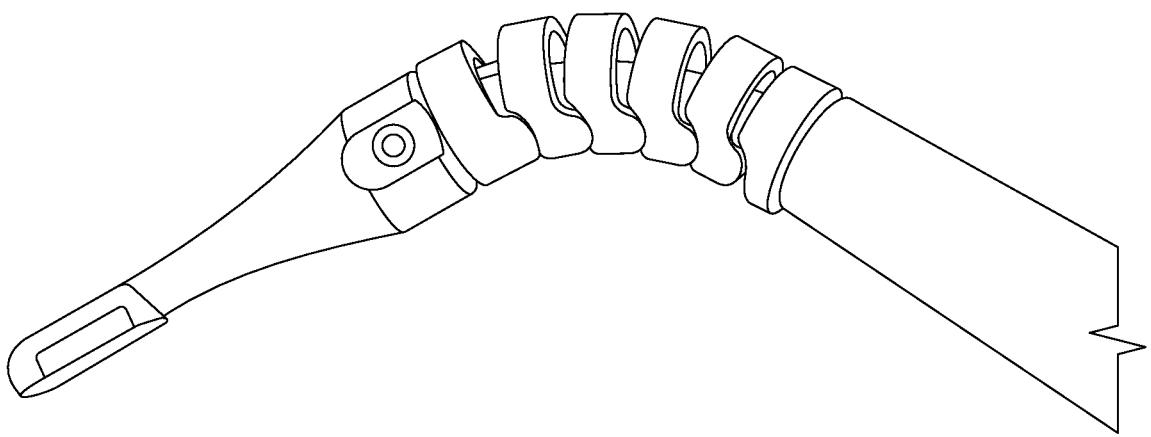
FIGS. 15A and 15B are illustrations of an orientation of a tip attachment of an embodiment of a disc space and/or end plate preparation tool in "bent" and "straight" tip configurations, respectively.
Figure 15B:
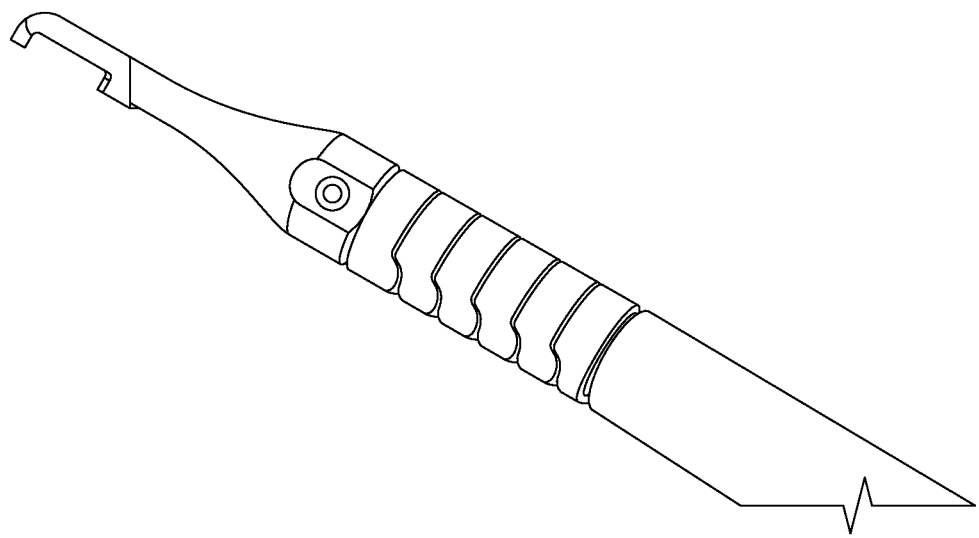
Figure 16:
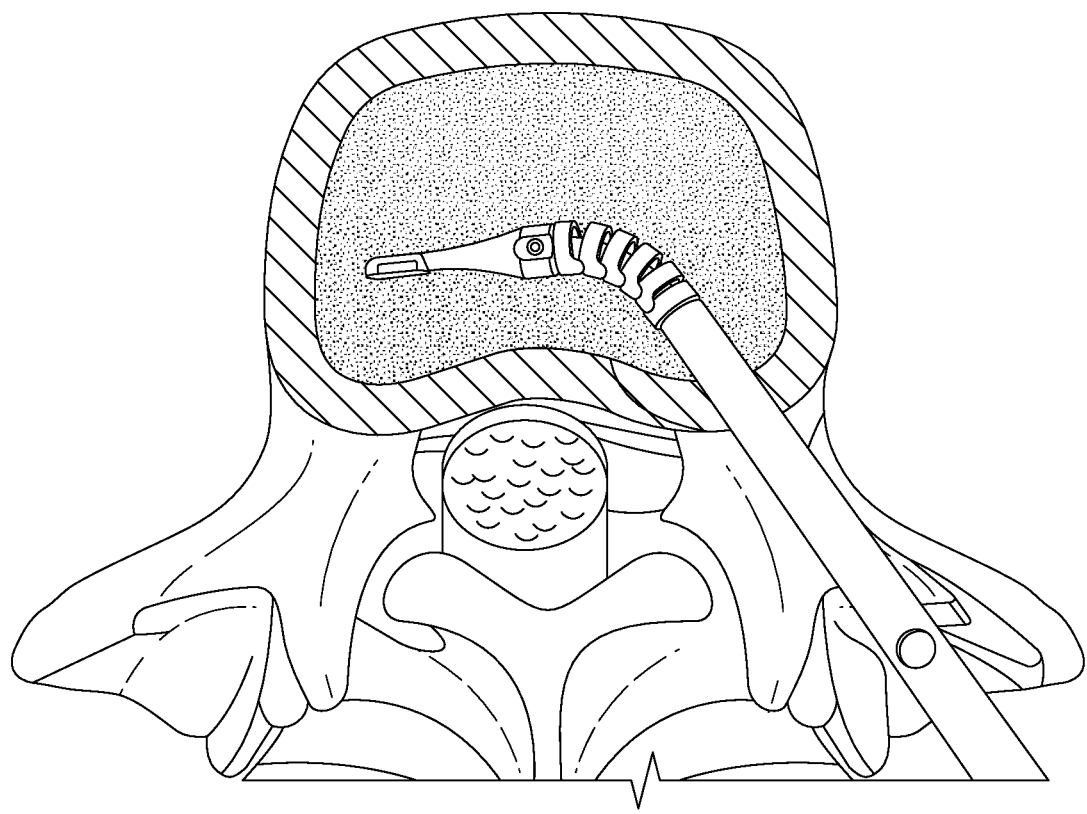
FIG. 16 is an illustration of an embodiment of a disc space and/or end plate preparation tool of the present invention, with a tip in a "bent" configuration, in use to debride a contralateral aspect of a disc space.

Adjustment of the control knob 410 of disc space preparation tools 400 of the present invention allows a surgeon to select and customize the angle of the tip 408 of the tool 400 relative to the handle 415 or shaft 416 of the tool. Meanwhile, the "spine" 407 ensures that the tip attachment 409 always maintains a consistent orientation relative to the handle 415 of the tool, as illustrated in FIGS. 15A and 15B. These features permit the surgeon to debride the contralateral aspects of the disc space, as illustrated in FIG. 16, which is not possible with previous disc space preparation tools.

Figure 17A:
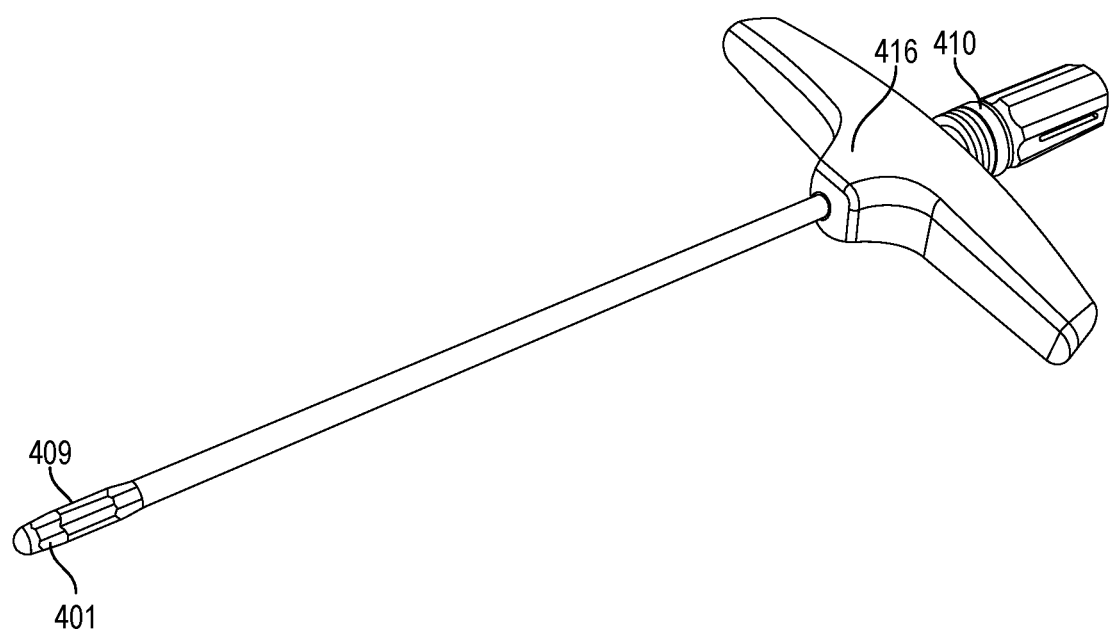
FIGS. 17A, 17B, and 17C are illustrations of an embodiment of an "eggbeater"- or "whisk"-type disc space and/or end plate preparation tool, with a tip attachment in collapsed, "hybrid" or "intermediate," and expanded configurations, respectively.
Figure 17B:
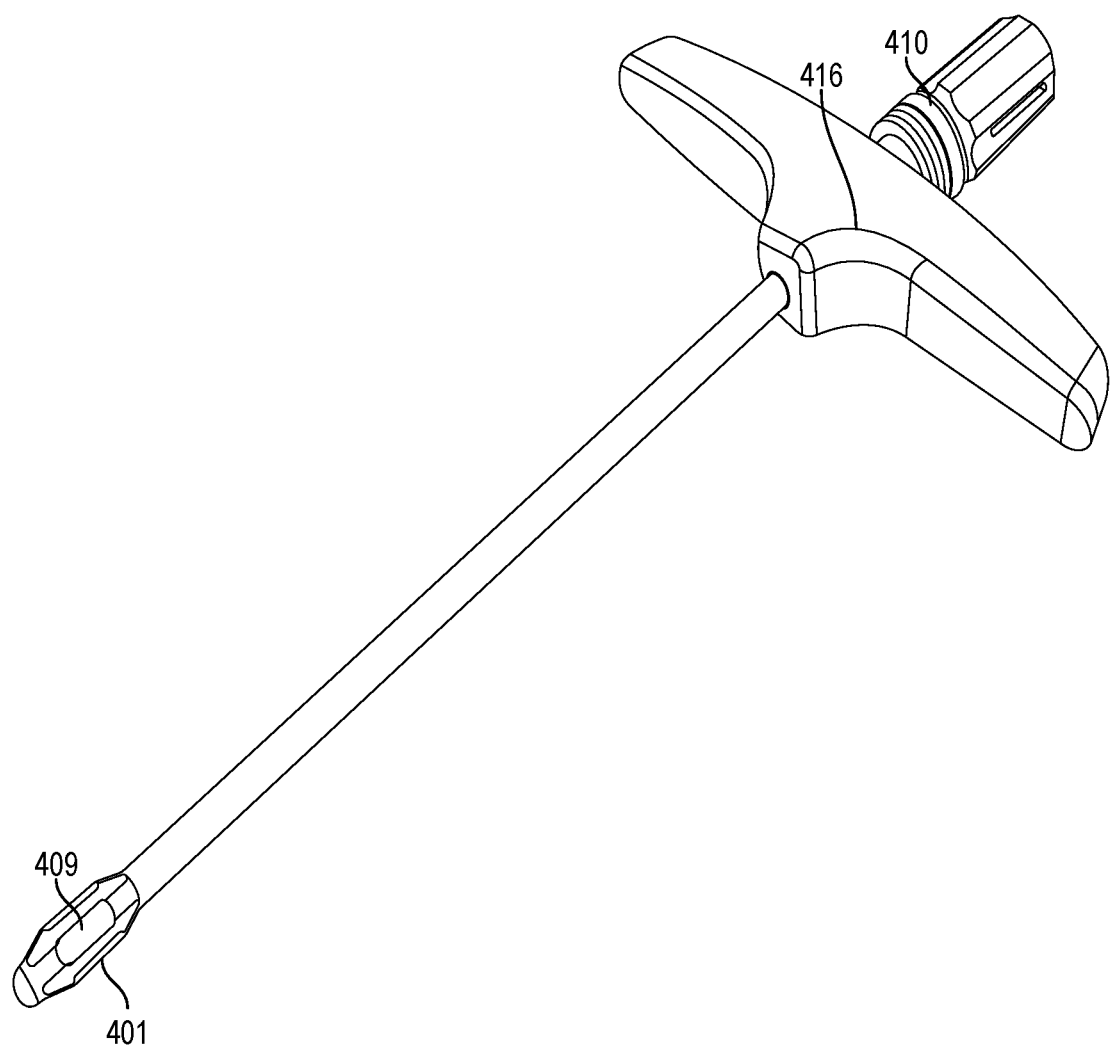
Figure 17C:
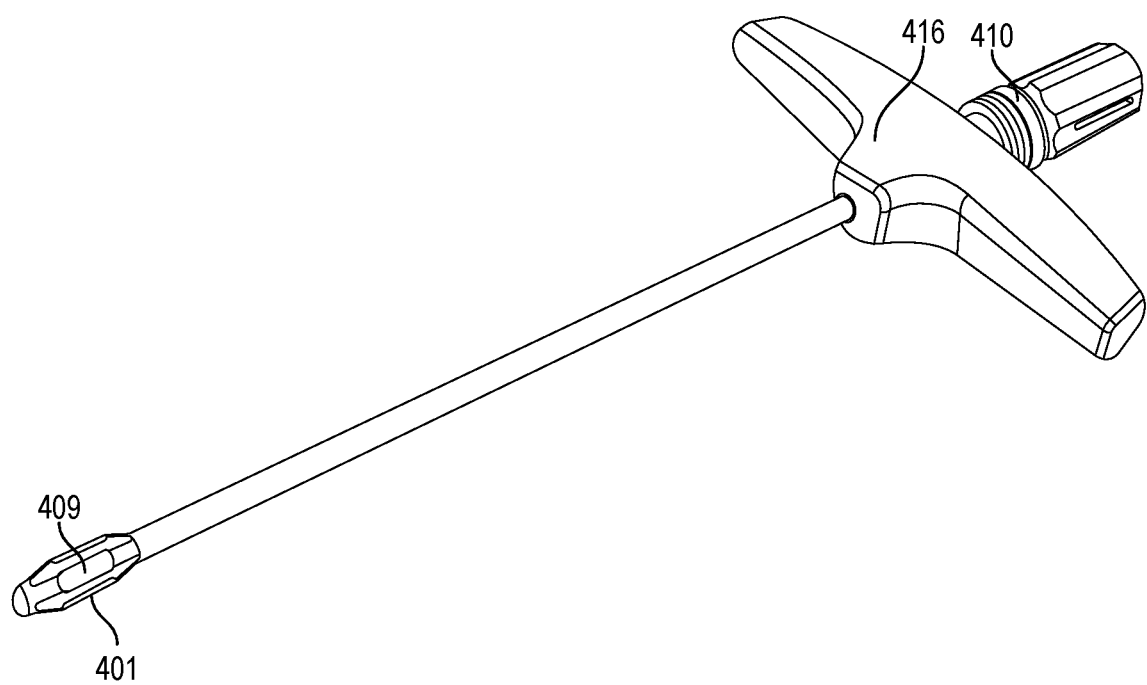
Figure 18A:
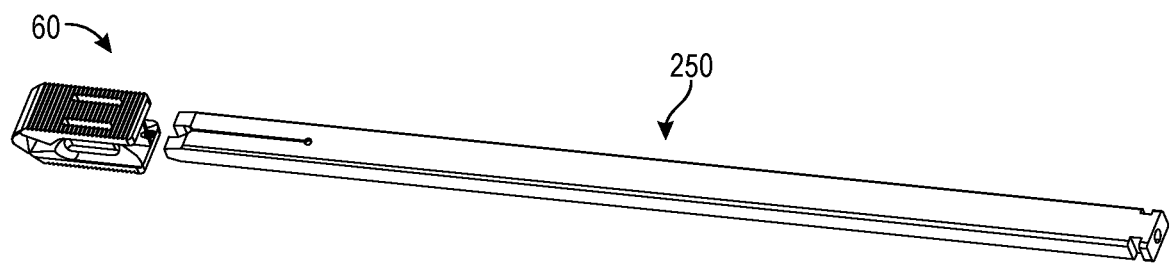
FIG. 18A is a left rear perspective view of a fusion cage with expandable fusion cage feature configured to communicate with an installer/impactor component according to yet another embodiment.
Figure 18B:
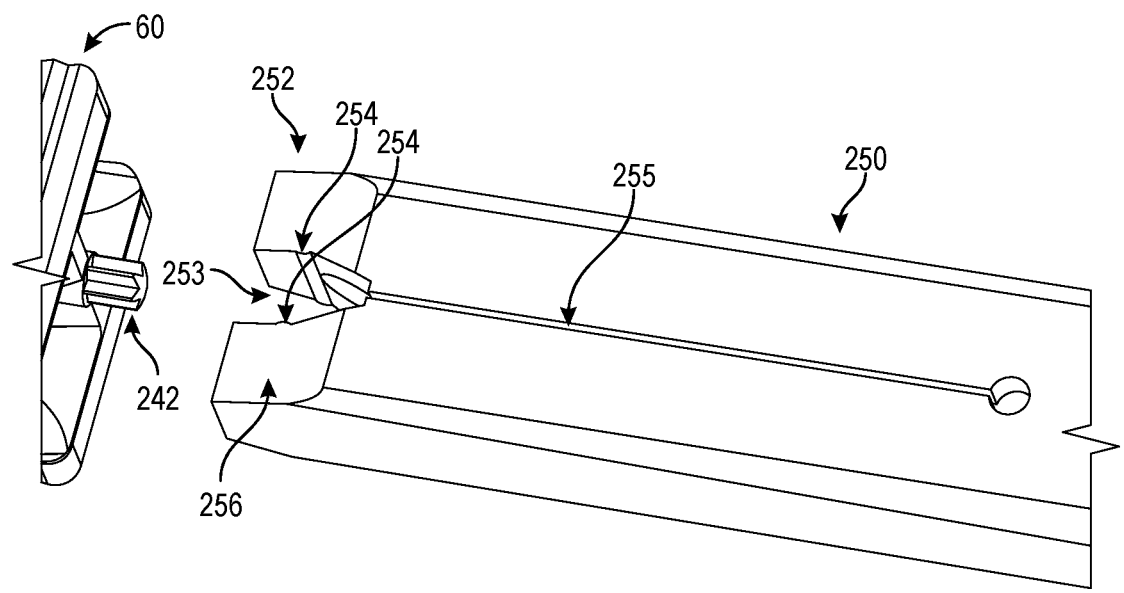
FIG. 18B is a close-up partial left rear perspective view of the devices of FIG. 18A.
Figure 19:
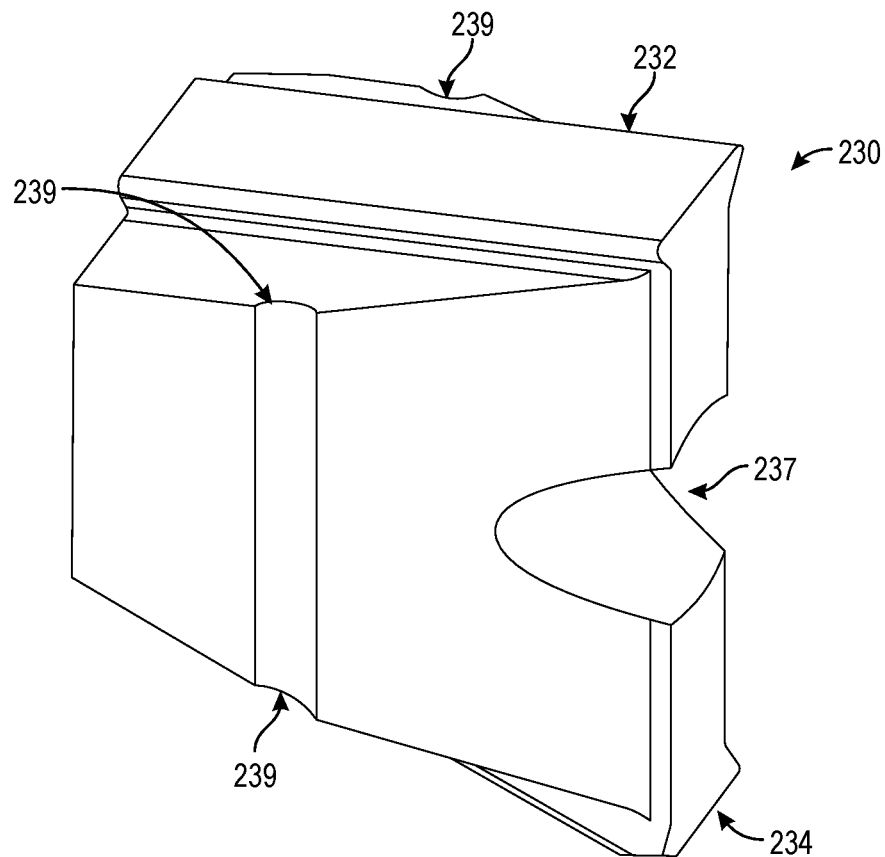
FIG. 19 is a left rear perspective view of the rear block component of the fusion cage of FIG. 18A.

In certain embodiments, the tip attachment 409 may be expandable; by way of non-limiting example, the tip attachment 409 may comprise a cannula 402 and/or a plurality of blades 401, e.g. as illustrated in FIGS. 1B, 3-8, and 17A-C, that is selectively expandable in situ from a collapsed position (e.g. with a diameter of 7 mm, as in FIG. 17A) to an expanded position (e.g. with a diameter of 16 mm, as in FIG. 17C). Embodiments of this type may also be expandable, collapsible, and/or configurable into a "hybrid" or "intermediate" position, as illustrated in FIG. 17B. This selective expansion of the tip attachment 409 allows a surgeon to insert a device of appropriate size into the disc space, and improves the efficiency and safety of endplate preparation. In embodiments comprising an expandable tip attachment 409, e.g. an "eggbeater" or "whisk"-type debridement tool such as those illustrated in FIGS. 1B, 3-8, and/or 17A-C, rotation of the control knob 410 may allow for precise and uniform expansion of the tip attachment 409, and the surgeon may continuously rotate the head within the disc space by rotating the handle 416, and therefore the shaft 418, of the tool.

Embodiments of the present invention relates to devices and methods for implanting a spinal fusion cage or other surgical implant, and particularly to tools comprising a leaf, tab, or other element by which a user may selectively attach and detach the implant. Thus, for example, the foregoing description of the various embodiments contemplates delivery to, for example, a window cut in a bone, where access to such window for bone grafting is difficult to obtain because of orientation of such window, presence of muscle tissue, risk of injury or infection, etc. The delivery device or tool is formed such that the spinal fusion cage or other surgical implant can be accurately, easily, and quickly placed in the window, or in any other target location, by selectively attaching and detaching the implant from the device. The same concept applies to other areas of a patient, whether or not a window has been cut in a bone, for example in a vertebral disc space, and may be used whether this is a first surgery to the area or a follow-up surgery.

In embodiments of a surgical implant delivery device according to the present invention, the surgical implant delivery device may comprise a cannula, a positioning handle, and an engaging portion. The positioning handle preferably comprises a pistol-like grip, but other types of grip, including by way of non-limiting example a pistol-type grip and a handlebar-type grip, are contemplated and are within the scope of the invention. The positioning handle may be permanently affixed to the cannula, or it may be selectively removable from the cannula. The engaging portion may comprise at least one flexible strip at least partially disposed within at least one track or groove in a distal end of the cannula. In one preferred embodiment, the engaging portion comprises two flexible strips, but any number of flexible strips, including one, three, or more, may be suitable for a desired application and is within the scope of the invention. Where there is more than one flexible strip and therefore more than one groove in the distal end of the cannula, the several grooves and flexible strips may, but need not, be distributed in a rotationally symmetric orientation about the outer surface of the cannula.

The engaging elements of the engaging portion of embodiments of the present invention may selectively engage and disengage corresponding engaging elements of the spinal fusion cage or other surgical implant, based on user inputs to the trigger of the surgical implant delivery device. Specifically, the engaging elements of the surgical implant delivery device may engage corresponding engaging elements of the surgical implant when the trigger is not actuated, or is in a neutral position, and may disengage the corresponding elements of the surgical implant when the trigger is actuated, or is in an activated position.

The flexible strips may be made of any suitable material, as will be understood by those of ordinary skill in the art, but may preferably be made of a nickel-titanium alloy, also known as Nitinol. Nitinol exhibits various advantageous mechanical properties, including shape memory and superelasticity, and is biocompatible and therefore already widely used in surgical tools and other medical devices.

The flexible strips of surgical implant delivery devices of the present invention are reconfigurable, and in particular may be reconfigured such that the engaging elements of the flexible strips have expanded or bowed outward relative to a starting configuration. This reconfiguration may be accomplished by actuation of a user-operable trigger. In general, the user-operable trigger may be operable with one hand, and preferably with one finger, and in particular may be configured to be actuated by compressing, pulling, or squeezing. In many embodiments, the engaging elements comprise a leaf or tab extending outwardly from a longitudinal axis of each flexible strip, but other engaging elements, as disclosed and described elsewhere herein, may also be suitable for use in the present invention.

The cannula itself will generally be cylindrical, or have a rectangular cross-section, but any shape of the cannula suitable for surgical use may be employed. Often, the cannula will have an inner or outer diameter of about eight millimeters, especially where the surgical implant delivery device is operable to receive and convey bone graft material to a surgical site. Other shapes and dimensions for the cannula and other components of the surgical implant delivery device may be employed as suitable for a particular application. Particularly, the cannula may be curved or angled such that the distal end, or a portion of the distal end, of the cannula is offset from or lies in a different plane than the proximal end, or a portion of the proximal end. The cannula will frequently be made of a biocompatible metal or metal alloy, and may especially comprise a ferrous material, but any material suitable for use in surgical tools and other medical devices may be employed.

The relative orientations and configurations of the cannula and engaging portion may take any suitable form for a desired application, but in general, the flexible strips of the engaging portion will be disposed at least partially within corresponding tracks or grooves in an external surface of a distal end of the cannula. In many cases it may be desirable for the flexible strips to extend beyond the distal end of the cannula, while in other cases the distal end of the flexible strips and the distal end of the cannula may be coterminous or in close proximity. In embodiments in which the surgical implant delivery device is operable to receive and convey bone graft material, it is generally desirable for the flexible strips not to impede an opening in the distal end of the cannula, and in these embodiments the flexible strips may terminate proximally (closer to a user) relative to the opening in the distal end of the cannula.

Additional or alternative components that are configured to engage a fusion cage 60 are provided in FIGS. 18-27. Generally, the additional components comprise those that allow the fusion cage 60 to be positioned at or within a surgical site, to expand and/or contract the fusion cage 60, and to detach the fusion cage 60.

With attention to FIGS. 18-24, a fusion cage 60 with an expandable fusion cage feature is depicted with an installer/impactor 250 component. The installer/impactor 250 comprises installer/impactor tip 252, installer/impactor aperture 253, installer/impactor ridge 254, installer/impactor channel 255, installer/impactor ramp 256 and installer/impactor handle 258. More particularly, in some embodiments, the installer/impactor 250 includes an installer/impactor tip 252 having at least one installer/impactor ramp 256, at least one installer/impactor ridge 254 formed on an interior of the at least one ramp 256, an installer/impactor aperture 253 adjacent to the at least one ridge 254, an installer/impactor channel 255 extending from the aperture along a longitudinal axis of the installer/impactor 250, and an installer/impactor handle 258 disposed on an end opposite the installer/impactor tip 252. The installer/impactor aperture 253 is configured to engage the rear block aperture 237 and the installer/impactor ridges 254 are configured to engage the rear block detent 239; once these elements are engaged, the fusion cage 60 may be accurately and reliably positioned at the surgical site. The installer/impactor handle 258, with integrated striking plate, may be used to assist in guiding the fusion cage 60 into place, and further allows a "persuading" with a mallet. The installer/impactor handle 258 attaches in place with, for example, a ball detent or similar feature that secures the installer/impactor handle 250 in place yet allows quick and easy removal.

Figure 20A:
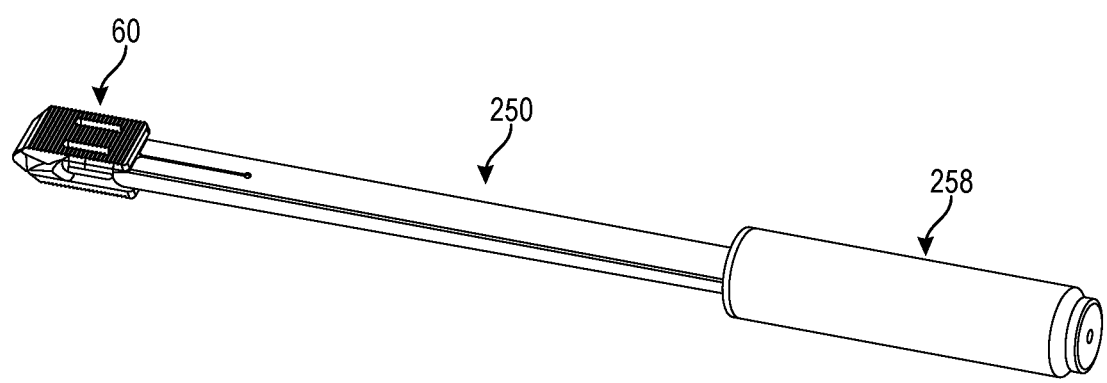
FIG. 20A is a left rear perspective view of the devices of FIG. 18A, shown with the fusion cage and installer/impactor components in an engaged state, and the installer/impactor comprising an installer/impactor handle.
Figure 20B:
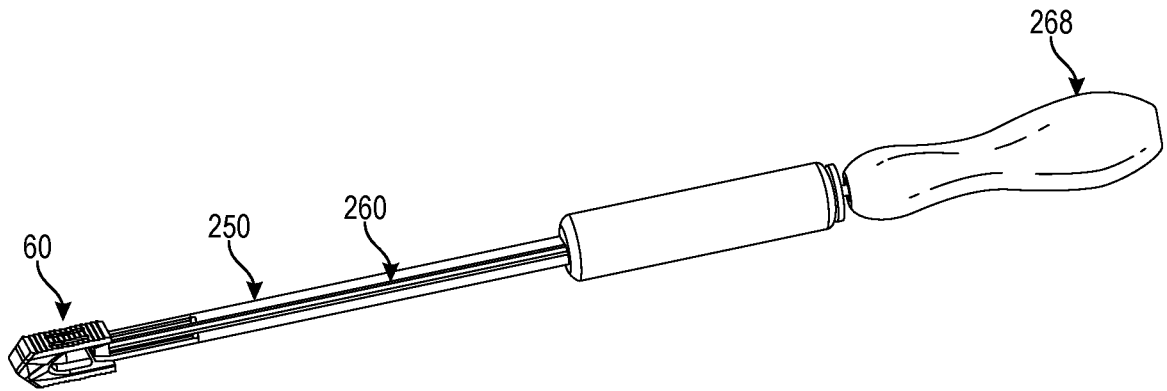
FIG. 20B is a left front perspective partial cross-sectional view of the devices of FIG. 18A in the state of FIG. 20A, shown with the fusion cage and installer/impactor components in an engaged state, the devices engaged with an expansion driver component, the installer/impactor component shown in partial cross-section to partially show the expansion driver fitted within the interior of the installer/impactor.
Figure 21:
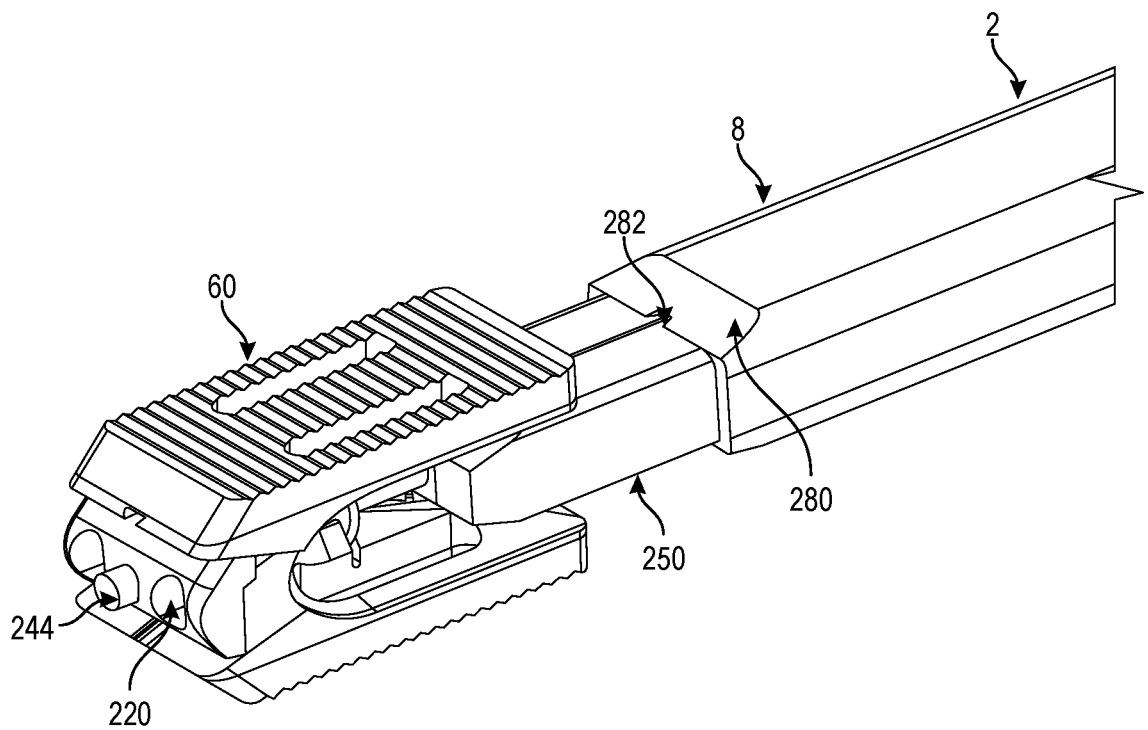
FIG. 21 is a left front perspective view of the devices of FIG. 18A, shown with the fusion cage and installer/impactor components in an engaged state, with the cannula component engaged with the installer/impactor component.

FIG. 20A details the installer/impactor 250 engaged with the fusion cage 60, the fusion cage 60 in an unexpanded state. FIG. 20B details the same system and configuration of FIG. 20A, except that the expansion driver 260, with expansion driver handle 268, is engaged with the fusion cage 60. More specifically, the expansion driver 260, which fits within the installer/impactor 250, engages the expansion screw head 242 (e.g. the expansion screw head 242 is a male star or Torx™ screw head that engages with the female star or Torx™ screwdriver end of the expansion driver 260.) FIG. 21 details the installer/impactor 250 engaged with the fusion cage 60, the fusion cage 60 in an expanded state (as a result of the expansion driver 260 engaging the expansion screw head 242 and, through rotation of the expansion screw head 242, expanding the fusion cage 60), and the cannula 2 fitted over the installer/impactor 250.

Figure 22:
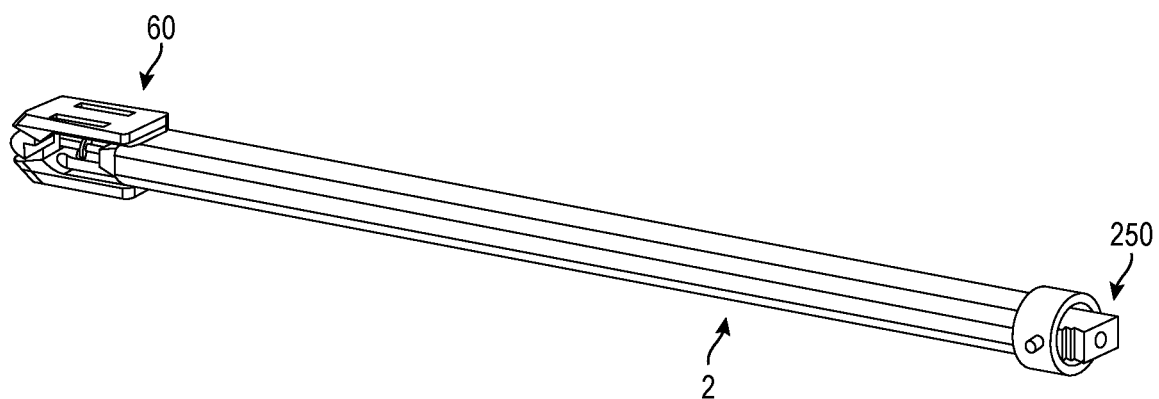
FIG. 22 is a left rear perspective view of the devices of FIG. 18A, shown with the fusion cage and installer/impactor components in an engaged state, and shown with the fusion cage and cannula in an engaged state.

After the fusion cage 60 is expanded to the desired degree, i.e. height, the expansion driver 260 disengages from the expansion screw head 242 and is removed. The cannula 2 is then slid downward or distally so as to engage the fusion cage 60, and the installer/impactor 250 may be removed, for example to allow bone graft material to be delivered via cannula 2 into the fusion cage 60 and the surrounding surgical site. FIG. 22 details the installer/impactor 250 engaged with the fusion cage 60, the fusion cage 60 in an expanded state, and the cannula 2 fitted over the installer/impactor 250 and engaged with the fusion cage 60. In an alternate embodiment, the installer/impactor 250 is not used, and instead the cannula 2 is used to position the fusion cage 60 by way of the cannula external ramp 280 and/or cannula notch 282. The cannula external ramp 280 may form a press-fit with the fusion cage 60. The cannula may also engage the fusion cage 60 via the cannula notch 282, the cannula notch 282 configured to engage the rear block aft 238 portion above and below the rear block aperture 237.

Figure 23A:
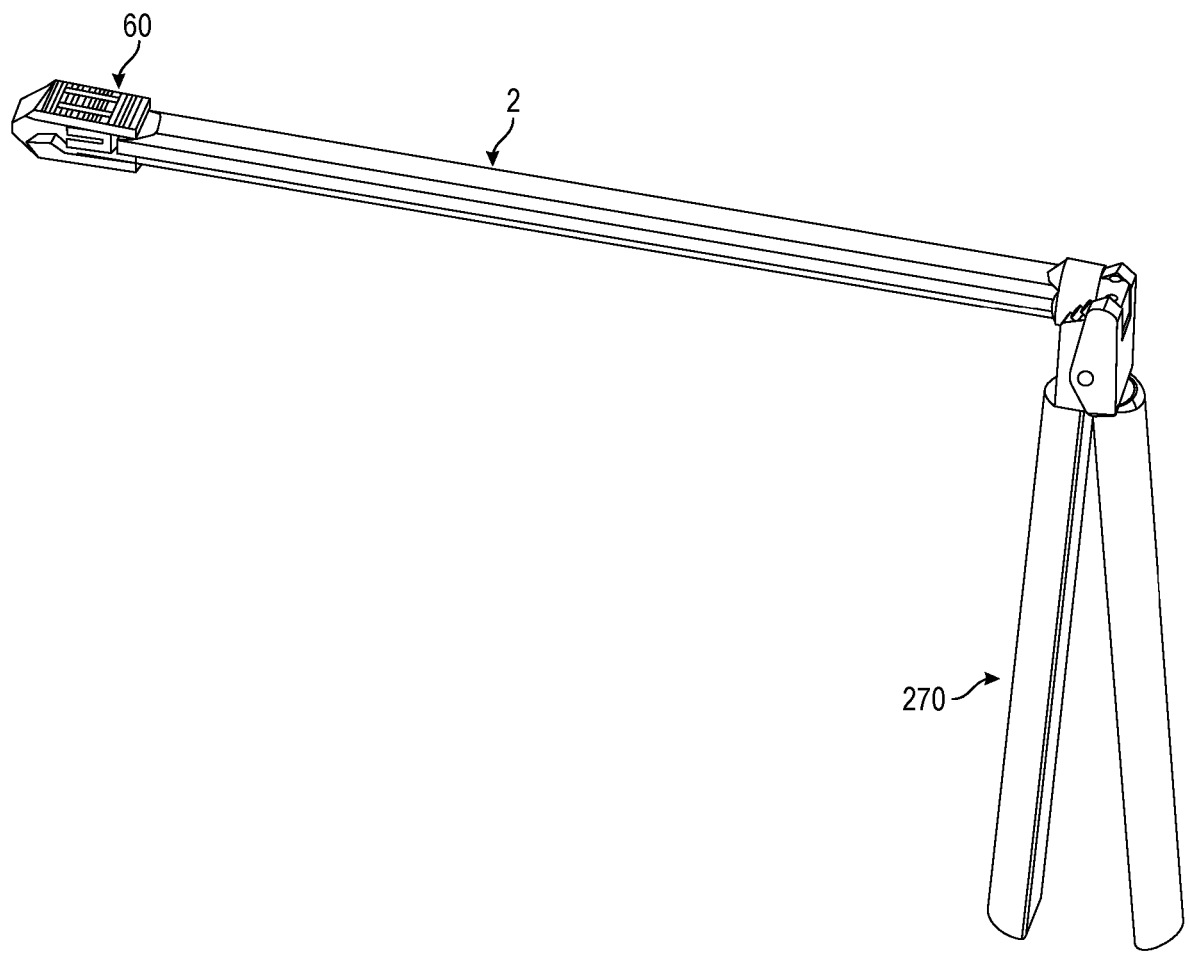
FIG. 23A is a left rear perspective view of the devices of FIG. 18A, shown in the configuration of FIG. 22, with a removal pliers component engaged with the cannula component.
Figure 23B:
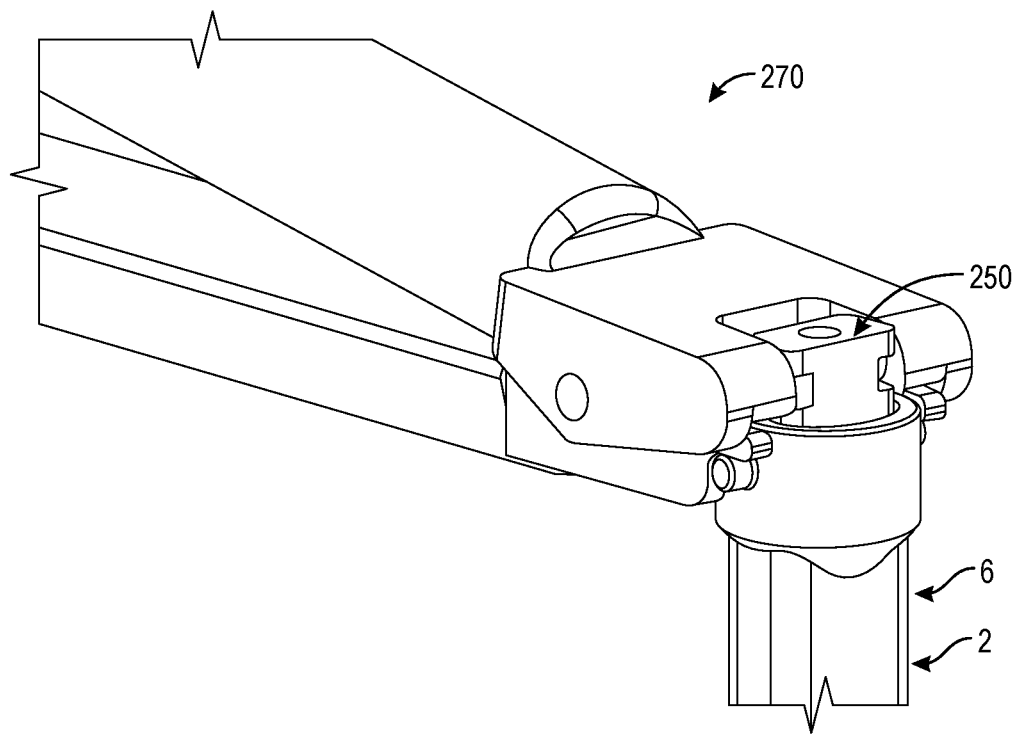
FIG. 23B is a close-up partial perspective view of the devices of FIG. 23A.

FIGS. 23A-B detail a means with which the installer/impactor 250 may be removed by use of removal pliers 270. The removal pliers 270 are configured to engage the first end 6 of cannula and the proximal end of the installer/impactor 250, so as to pull the installer/impactor 250 from engagement with the fusion cage 60. Note that the installer/impactor 250 is configured to allow the installer/impactor tip 252 to spread apart over the rear block detent 239 groove, as facilitated by the installer/impactor channel 255.

Figure 24:
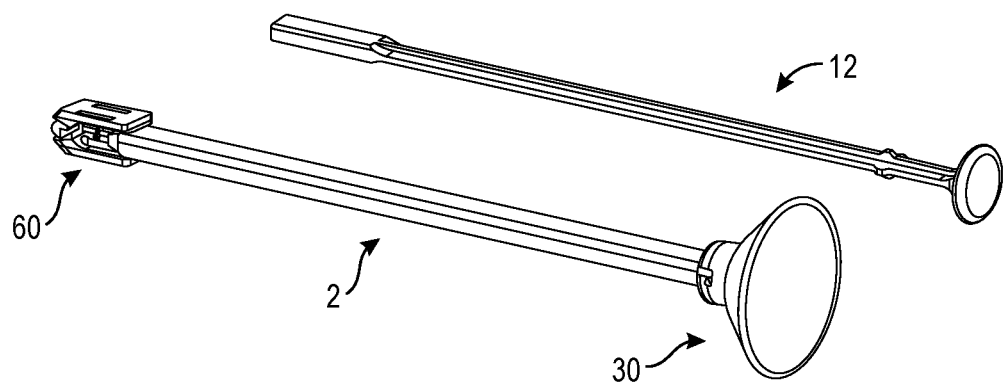
FIG. 24 is a left rear exploded perspective view of a fusion cage with expandable fusion cage feature engaged with a cannula component and a funnel component, as configured to engage with a plunger component.

After the fusion cage 60 has been positioned in the surgical site and expanded as required, bone graft material may be inserted into the fusion cage 60 and into the surrounding surgical site. FIG. 24 presents an exploded perspective view of the fusion cage 60 with expandable fusion cage feature engaged with the cannula 2 component and funnel 30 component, as configured to engage with the plunger 12 component. As described previously, bone graft material is placed into the funnel 30 and advanced down the cannula 2 by the plunger 12, whereby bone graft material flows into the fusion cage 60 and outward into the surgical site via one or more of the upper plate openings 203, lower plate openings 213, and lateral openings distal to the front block 230.

Figure 25:
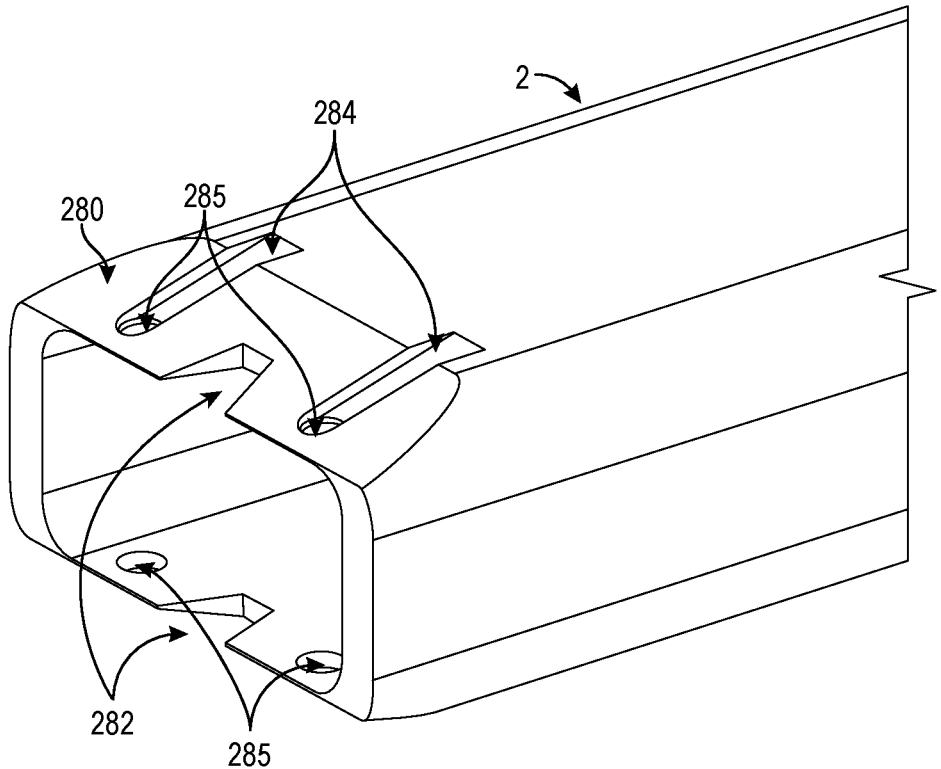
FIG. 25 is a left front partial perspective view of another embodiment of the cannula component configured to engage a fusion cage with expandable fusion cage feature, the cannula configured with cannula slot and cannula slot aperture features.
Figure 26:
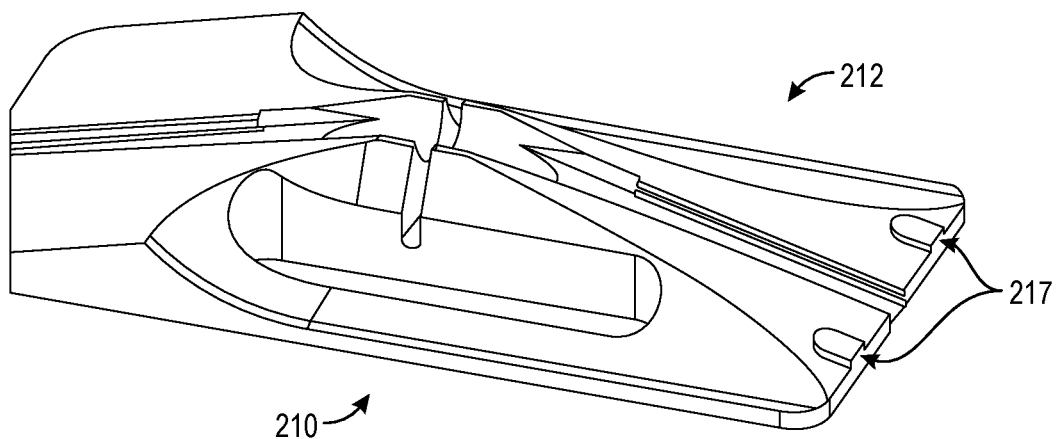
FIG. 26 is a left rear perspective view of another embodiment of the lower plate component of a fusion cage with expandable fusion cage feature, the lower plate configured with a plate tab feature configured to engage the cannula slot and cannula slot aperture features of FIG. 25.
Figure 27:
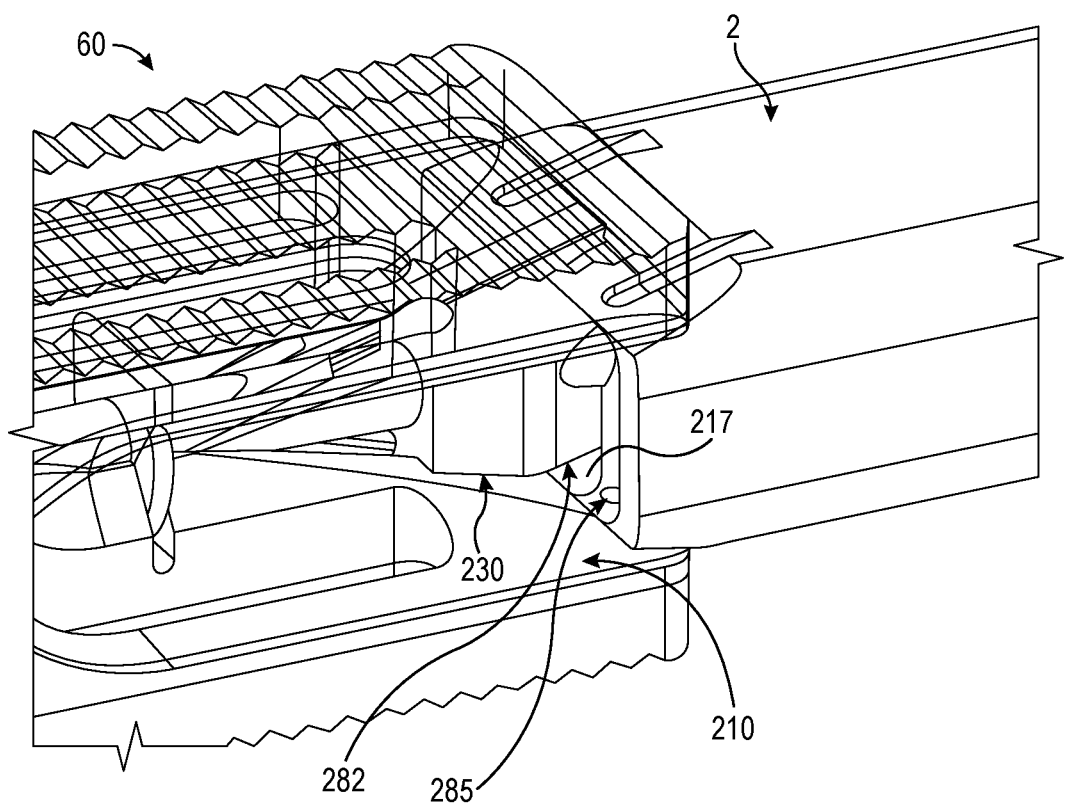
FIG. 27 is a left front partial cross-section perspective view of the devices of FIGS. 25 and 26, shown with the plate tab feature engaged with the cannula slot and cannula slot aperture features.
Figure 28:
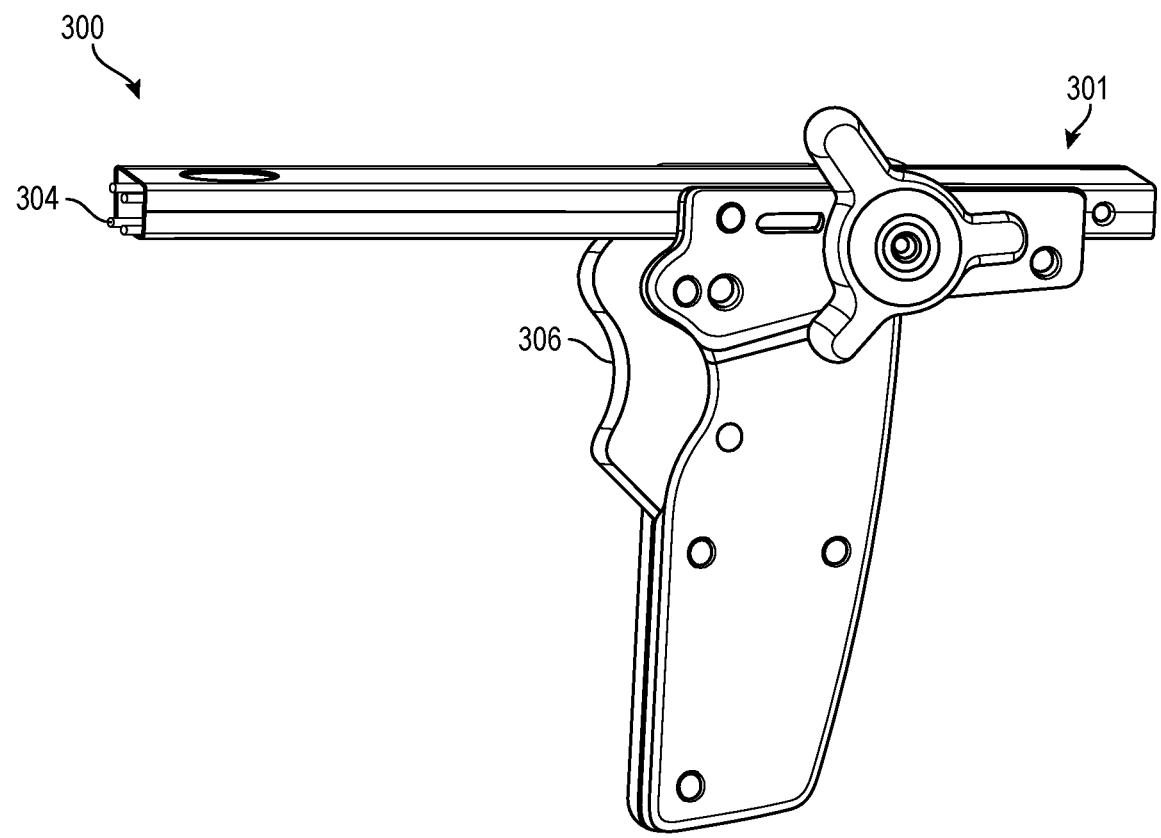
FIGS. 28-36 illustrate steps of one embodiment of a method for installing an expandable fusion cage or other surgical implant and providing bone graft material to the implant, according to the present invention.
Figure 29:
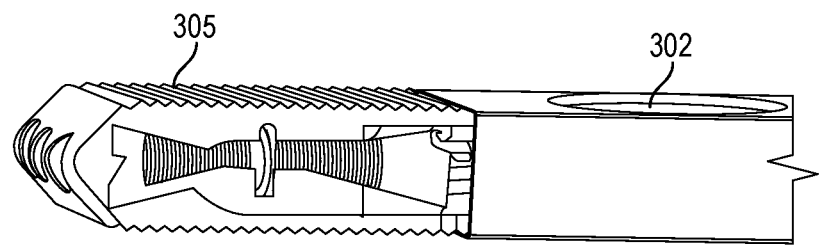
Figure 30:
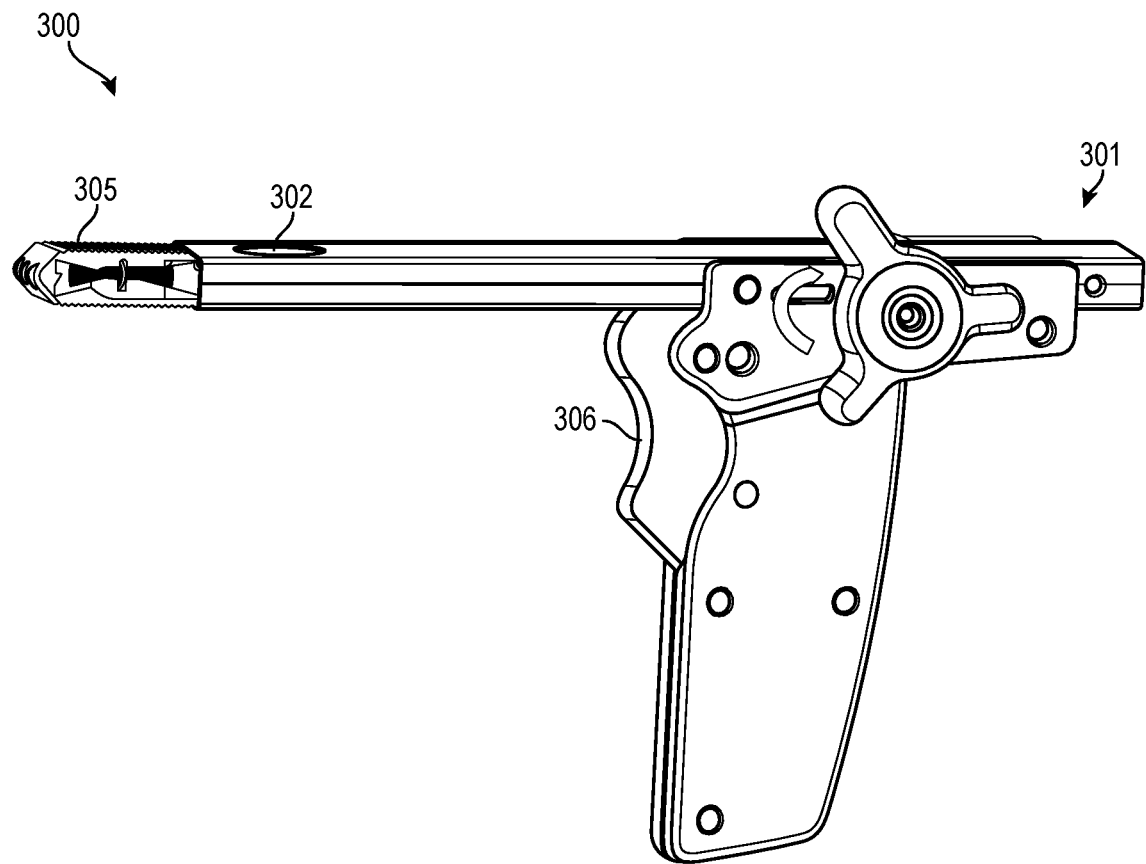
Figure 31:
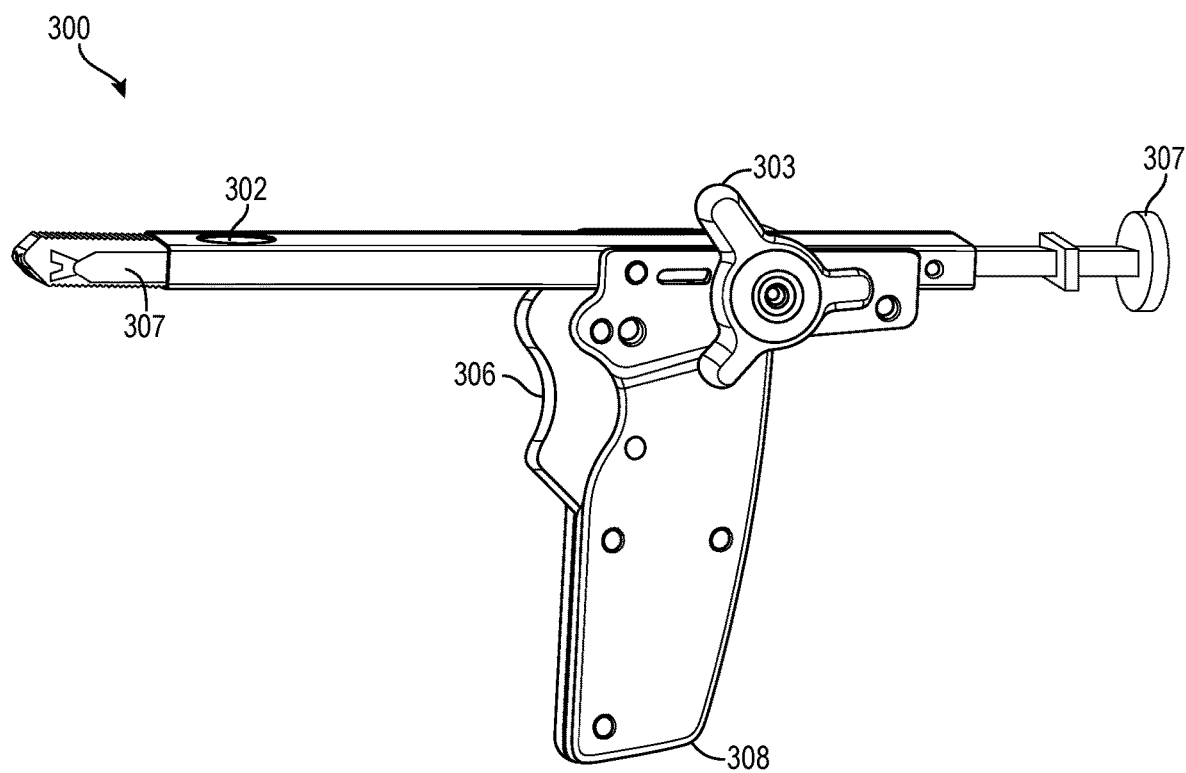
Figure 32:
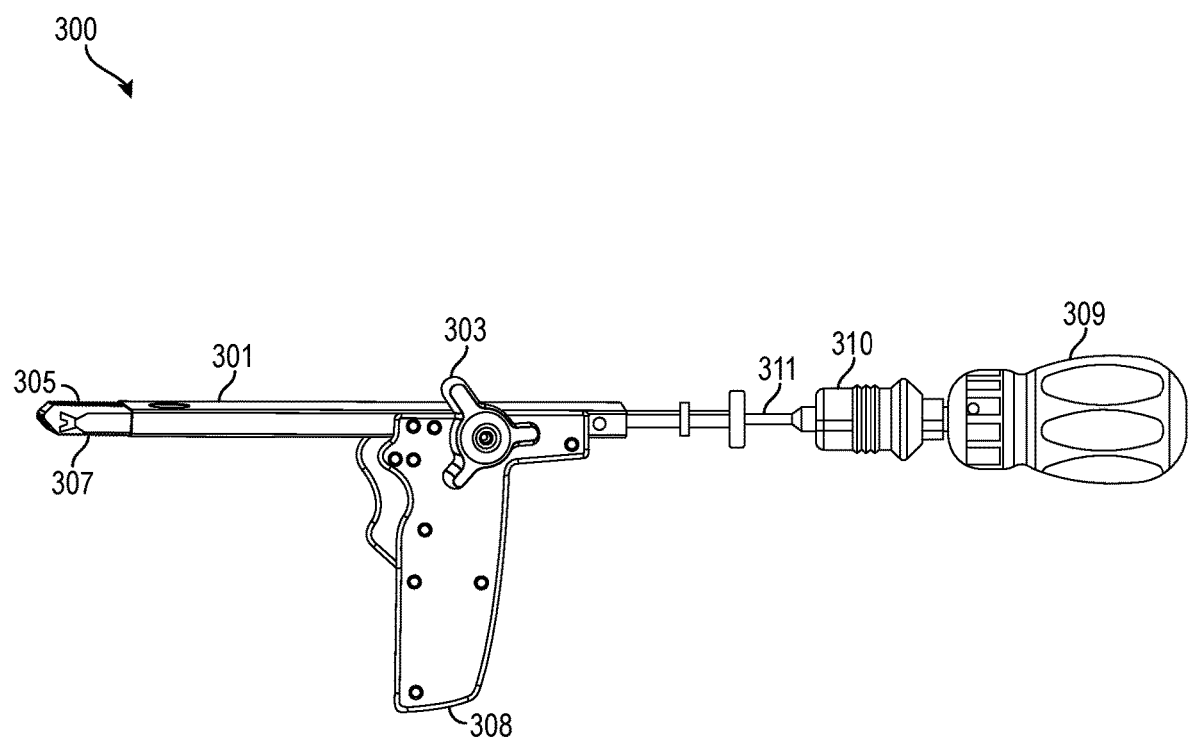
Figure 33:
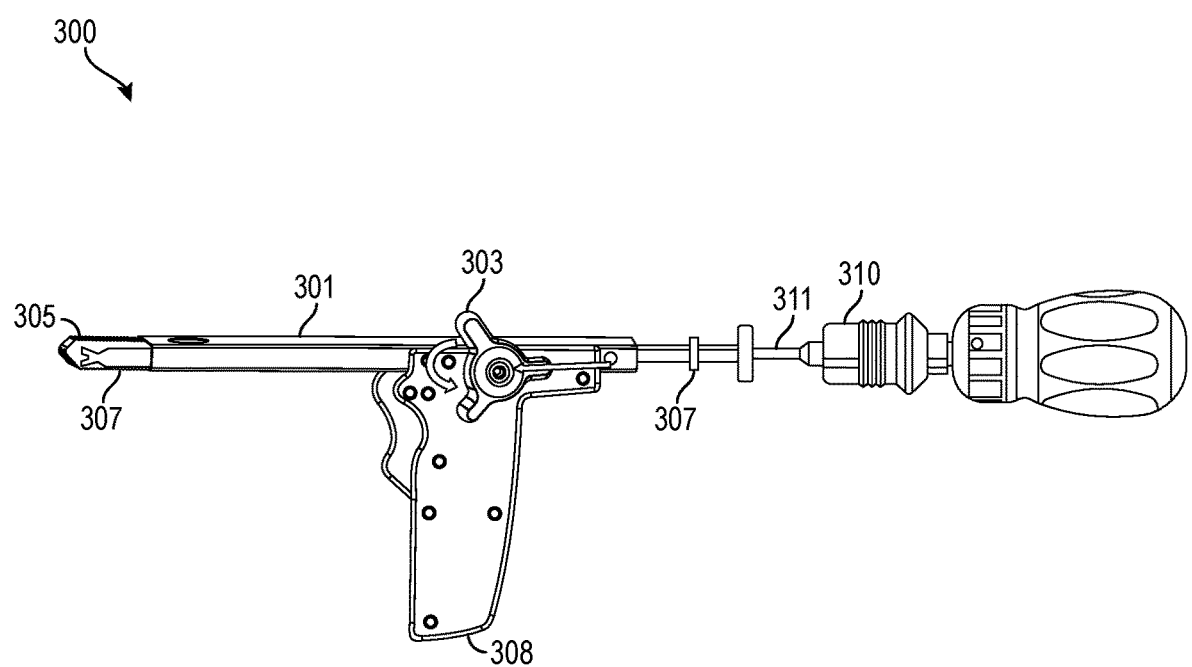
Figures 34A, 34B:
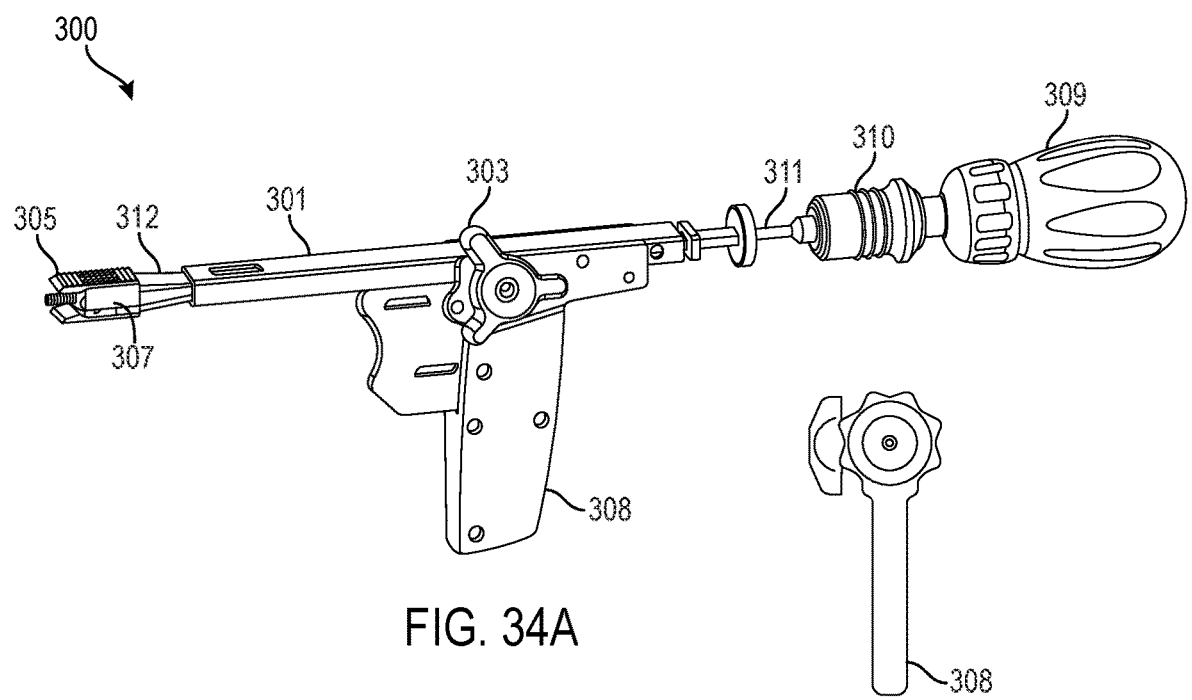
Figure 35:
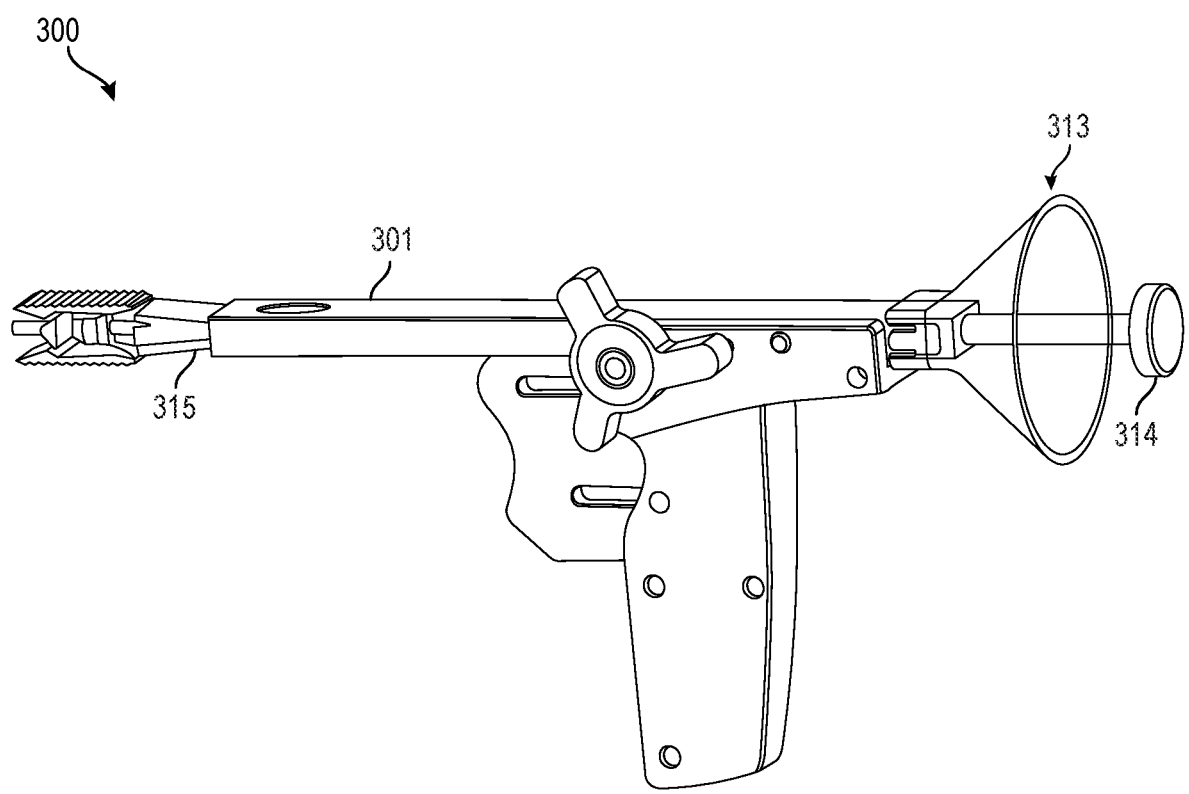
Figure 36:
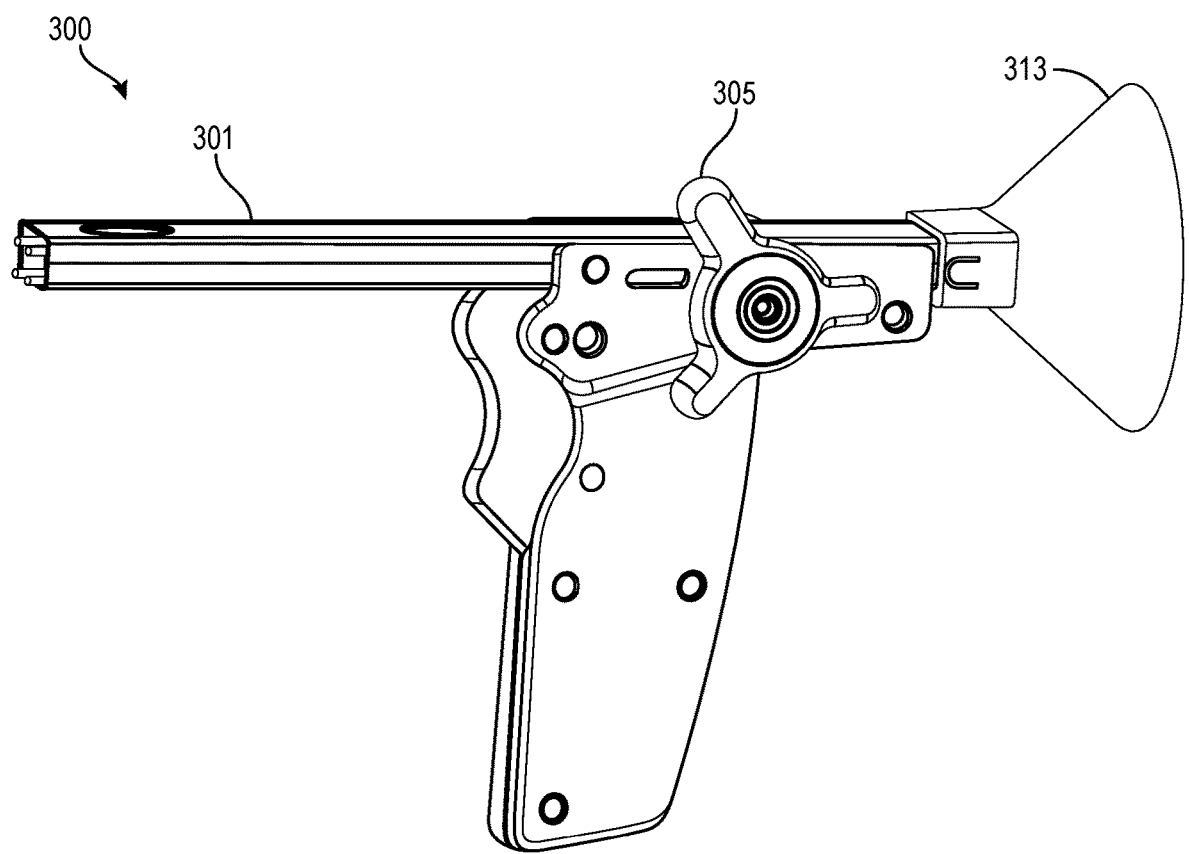

FIGS. 25-27 depict an alternate embodiment of cannula 2 and fusion cage 60 to enable the fusion cage 60 to be accurately and reliably positioned at a surgical site. The cannula 2 comprises two pairs of cannula slots 284, each with a cannula slot aperture 285 at the distal end. Each cannula slot 284 is disposed at least partially on the cannula external ramp 280. Each of the upper plate 200 and lower plate 210 comprise a pair of plate tabs 217, each of which engages one of the cannula slot apertures 285. When such an engagement occurs, the fusion cage 60 is slightly expanded as the cannula 2 is inserted into the fusion cage 60. In this arrangement, as the fusion cage 60 is expanded, the plate tabs 217 retreat or release from the cannula slot apertures 285; however, the cannula 2 still engages or registers with the fusion cage 60 via the cannula notches 282 which remain engaged with the rear block aft 238.

In one embodiment, the expansion screw 240 is configured to lock at defined expansion states of the fusion cage 60, to include at a maximum expansion state (as defined, e.g. as the maximum height dimension of which the fusion cage 60 may expand.)

Referring now to FIGS. 28-36, steps of one embodiment of a method for installing an expandable fusion cage or other surgical implant and providing bone graft material to the implant, via an insertion tool 300, are illustrated. In a first step of the method, illustrated in FIG. 28, a slidable rectangular shaft 301 of the insertion tool 300 provides for attachment of a bone graft application funnel 313 and, when retracted, expansion of a fusion cage 305. Expandable tabs 304 of the insertion tool 300 are compressed through a window 302, which allows reversible attachment of the fusion cage 305 to the insertion tool 300. In a second step of the method, illustrated in FIG. 29, the window 302 allows compression of the expandable tabs 304 so that tabs 304 can be inserted into corresponding receptacles of the fusion cage 305. In a third step of the method, illustrated in FIG. 30, when the fusion cage 305 is attached to the insertion tool 300, a trigger 306 of the insertion tool 300 is compressed against a handle 308 of the insertion tool 300, which pushes the slidable rectangular shaft 301 against the fusion cage 305 to provide tight compression between the shaft 301 and fusion cage 305 in preparation for insertion of the fusion cage 305 into a disk space of a patient. In a fourth step of the method, also illustrated in FIG. 30, a wingnut 303 of the insertion tool 300 is loosened to allow for sliding of the rectangular shaft 301 against the fusion cage 305, then tightened once appropriate compression and stabilization are achieved. The handle 308 allows for rotational control of the fusion cage 305 during the insertion process. In a fifth step of the method, illustrated in FIG. 31, a bifid insertion plunger 307, which has a central portal that communicates with a screw of the fusion cage 305, is inserted. The insertion plunger 307 serves as an impaction device to allow for driving of the fusion cage 305 into the disk space. In a sixth step of the method, illustrated in FIG. 32, the position of the insertion plunger 307 is maintained, and a ratcheting screwdriver handle 309, which is attached to a quick connect device 310, is further attached to a screwdriver shaft 311 and mated with the screw of the fusion cage 305. The wingnut 303 is released, allowing the slidable rectangular shaft 301 to be pulled back and permit expansion of the fusion cage 305 via operation of the screwdriver shaft 311. In a seventh step of the method, illustrated in FIG. 33, the slidable rectangular shaft 301 is locked into position by tightening the wingnut 303. In an eighth step of the method, illustrated in FIGS. 34A (side view) and 34B (end view), the slidable rectangular shaft 301 is pulled back and tightened into position via the wingnut 303. An expansion tool complex, consisting of the ratcheting screwdriver handle 309, the quick connect device 310, and the screwdriver shaft 311, is rotated to engage the screw of the fusion cage 305, causing the fusion cage 305 to expand within the disk space. In a ninth step of the method, illustrated in FIG. 35, the insertion plunger 307 and the expansion tool complex 309, 310, 311 are removed, and the bone graft application funnel is attached to the slidable rectangular shaft 301 so that bone graft material can be inserted into, and applied a long a length of, the slidable rectangular shaft 301 into the fusion cage 305 and thence into the disk space. A bone graft plunger 314 having a pliably extendable tip allows insertion of the bone graft material up to and/or beyond an expansion site 315 of the fusion cage 305. In a tenth step of the method, illustrated in FIG. 36, the bone graft plunger 314 is removed and a plug (not pictured) is slid over the screw of the inserted fusion cage 305 to prevent extrusion of the bone graft material. The wingnut 303 is loosened and the slidable rectangular shaft 301 is pushed toward the fusion cage 305, which in turn causes compression of the tabs 304 and releases the cage 305 from the insertion tool 300.

Figure 37A:
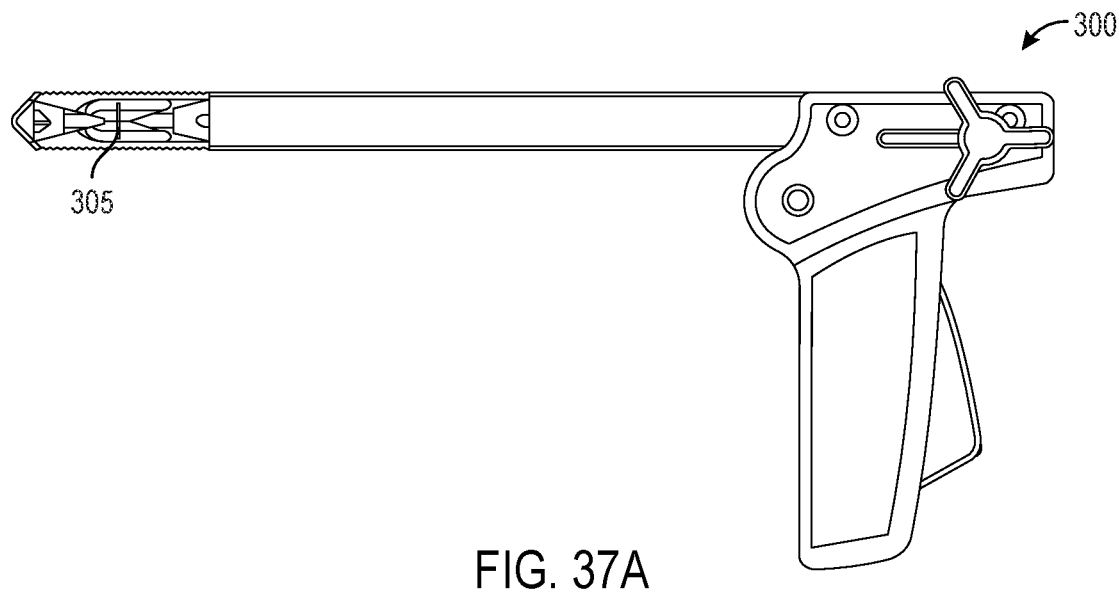
FIGS. 37A and 37B are side and perspective views, respectively, of one embodiment of a surgical implant delivery device suitable for use in the method illustrated in FIGS. 28-36.
Figure 37B:
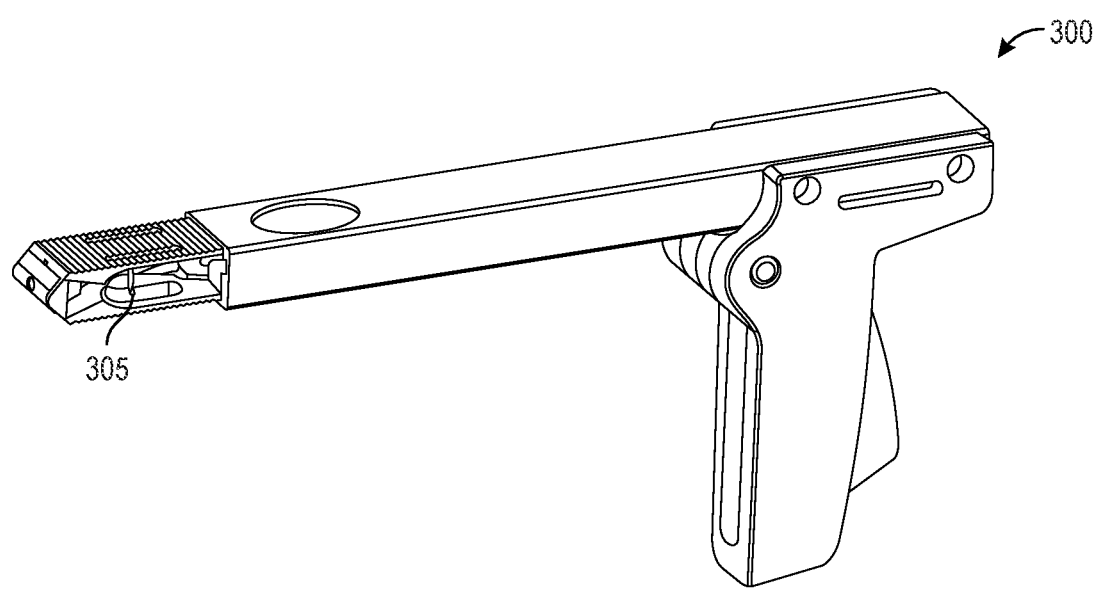

FIGS. 37A and 37B are side and perspective views, respectively, of one embodiment of an insertion tool 300 suitable for use in the method illustrated in FIGS. 28-36. In FIGS. 37A and 37B, the insertion tool 300 is shown with an attached expandable spinal fusion cage 305.

Figure 38A:
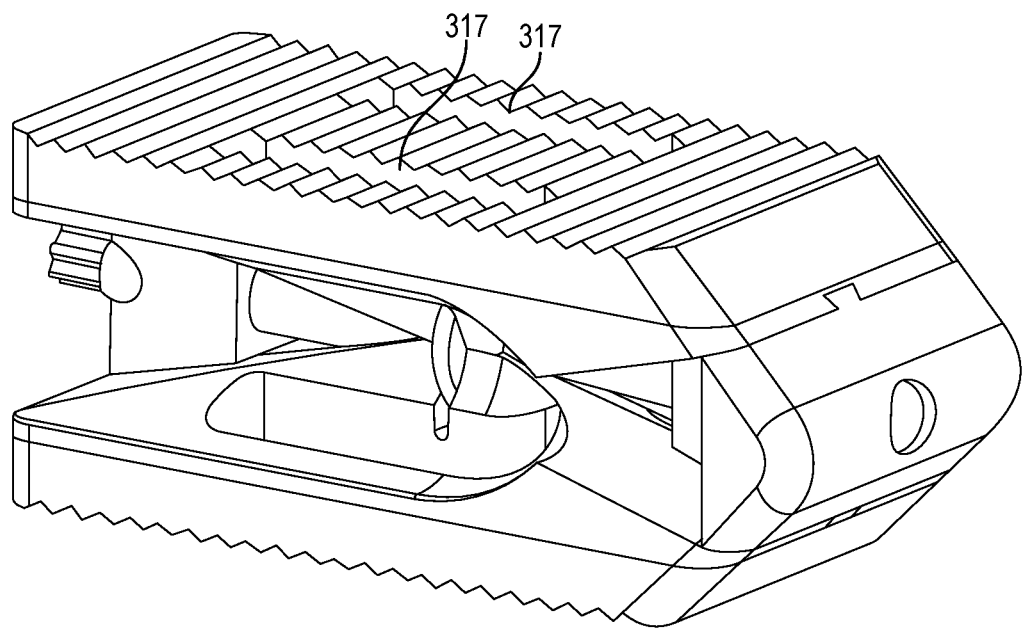
FIGS. 38A and 38B are illustrations of expandable spinal fusion cages suitable for use in embodiments of the present invention.
Figure 38B:
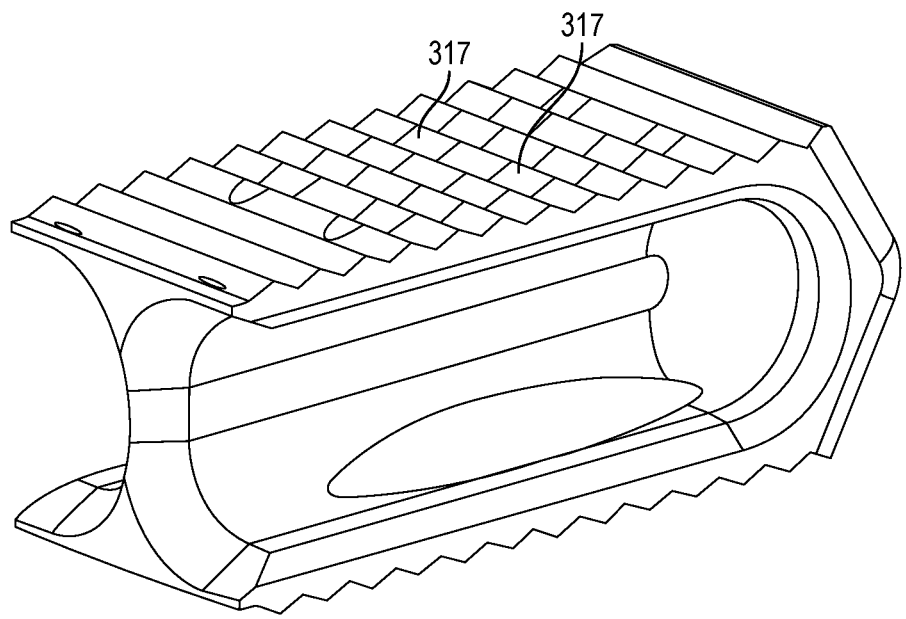

Referring now to FIGS. 38A and 38B, two embodiments of a fusion cage 305 are illustrated. These and other spinal fusion cages 305 are suitable for use in the systems and methods of the present invention, and may be adapted for use with a selectively attachable and detachable plate 316 as described below, and/or may be configured to selectively engage or disengage with cannulas, engaging elements, and/or surgical implant delivery devices as disclosed herein. Particularly, fusion cages 305, especially expandable fusion cages, as illustrated in FIGS. 38A and 38B may be provided with a groove, slot, track, or other element 317 that allows the fusion cage 305 to be securely attached to, and selectively detached from, a plate 316, cannula, and/or engaging element of a surgical implant delivery device.

Figure 39:
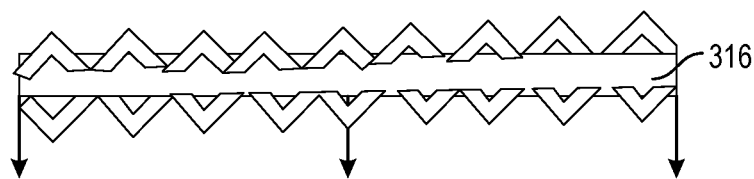
FIG. 39 is an end view of a selectively attachable and detachable plate according to embodiments of the present invention.

Referring now to FIG. 39, a selectively attachable and detachable plate 316 for use in conjunction with the fusion cages of FIGS. 38A and 38B is illustrated. In the embodiment illustrated in FIG. 39, at least one surface of the plate 316 has a roughened or "sawtooth" structure to secure purchase with corresponding ridges of a surface of the body of the fusion cage 305; it should be noted that a roughened or ridged surface may be provided for other purposes (such as to engage a bone surface) as well. The plate 316 illustrated in FIG. 39 is configured to selectively attach and detach from the fusion cage of FIGS. 38A and 38B, such that a bottom surface of the plate 316 may be in flush contact with a top surface of the fusion cage 305, and/or such that a top surface of the plate 316 may be in flush contact with a bottom surface of the fusion cage 305.

In the embodiment illustrated in FIG. 39, the means by which the plate 316 is selectively attachable and detachable is a snug-fit or "snap-on" mechanism enabled by the sawtooth structures of the plate 316 and fusion cage 305, such that the plate 316 can be quickly and easily affixed to the fusion cage 305 by application of manual force by a technician, and such that the plate 316 is in flush contact with the fusion cage 305 about substantially all of a perimeter of the plate. Other attachment/detachment mechanisms, including but not limited to quick key insertion, external snap detent, and magnetic attraction, are expressly contemplated and may be used by those of ordinary skill in the art in appropriate applications.

One primary purpose of the snap-on plate 316 as illustrated in FIG. 39 is to augment the height of the surgical fusion cage 305. By way of non-limiting example, where a height of the fusion cage 305 may be between about 8 millimeters and about 14 millimeters in the absence of the plate, with the plate 316 attached the total height of the cage 305 and plate 316 may be between about 14 millimeters and about 28 millimeters. This height augmentation is highly desirable in that it provides the capability to snugly fit into a larger than usual intervertebral space, such as that of a particularly tall patient, without the need to provide multiple fusion cages of various heights.

Although not illustrated in FIG. 39, where the fusion cage 305 comprises an attachment element configured to selectively engage and disengage an engaging element of a cannula or other surgical implant delivery device or system, a similar and/or corresponding feature may be provided on the plate. By way of non-limiting example, where the attachment element of the fusion cage 305 is a groove, slot, or track 317 in the top face of the fusion cage 305, a corresponding groove, slot, or track 317 may be provided in the top and/or bottom faces of the plate 316 to facilitate attachment of the cage 305 and plate 316 to an engaging element of the implant delivery device. Alternatively, or additionally, the plate 316 may be provided with a tab, leaf, or detent to securely interconnect to the groove, slot, or track 317 of the fusion cage. Features may be provided that enable a user of a cannula, surgical implant delivery device, or other implement to simultaneously engage or disengage the fusion cage 305 from the implement, the fusion cage 305 from the plate 316, and/or the plate 316 from the implement.

Figure 40A:
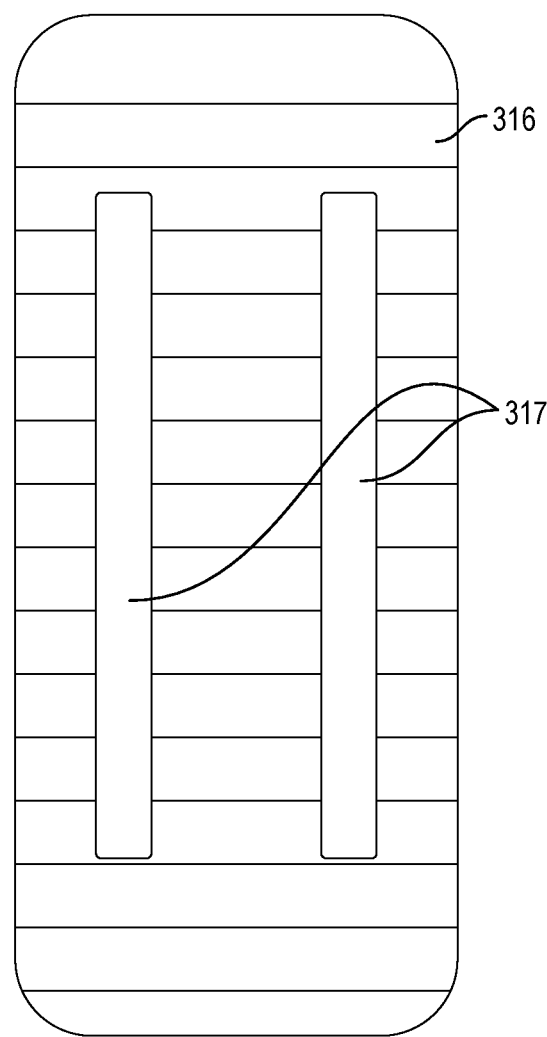
FIG. 40A is a top view of a selectively attachable and detachable plate according to embodiments of the present invention.
Figure 40B:
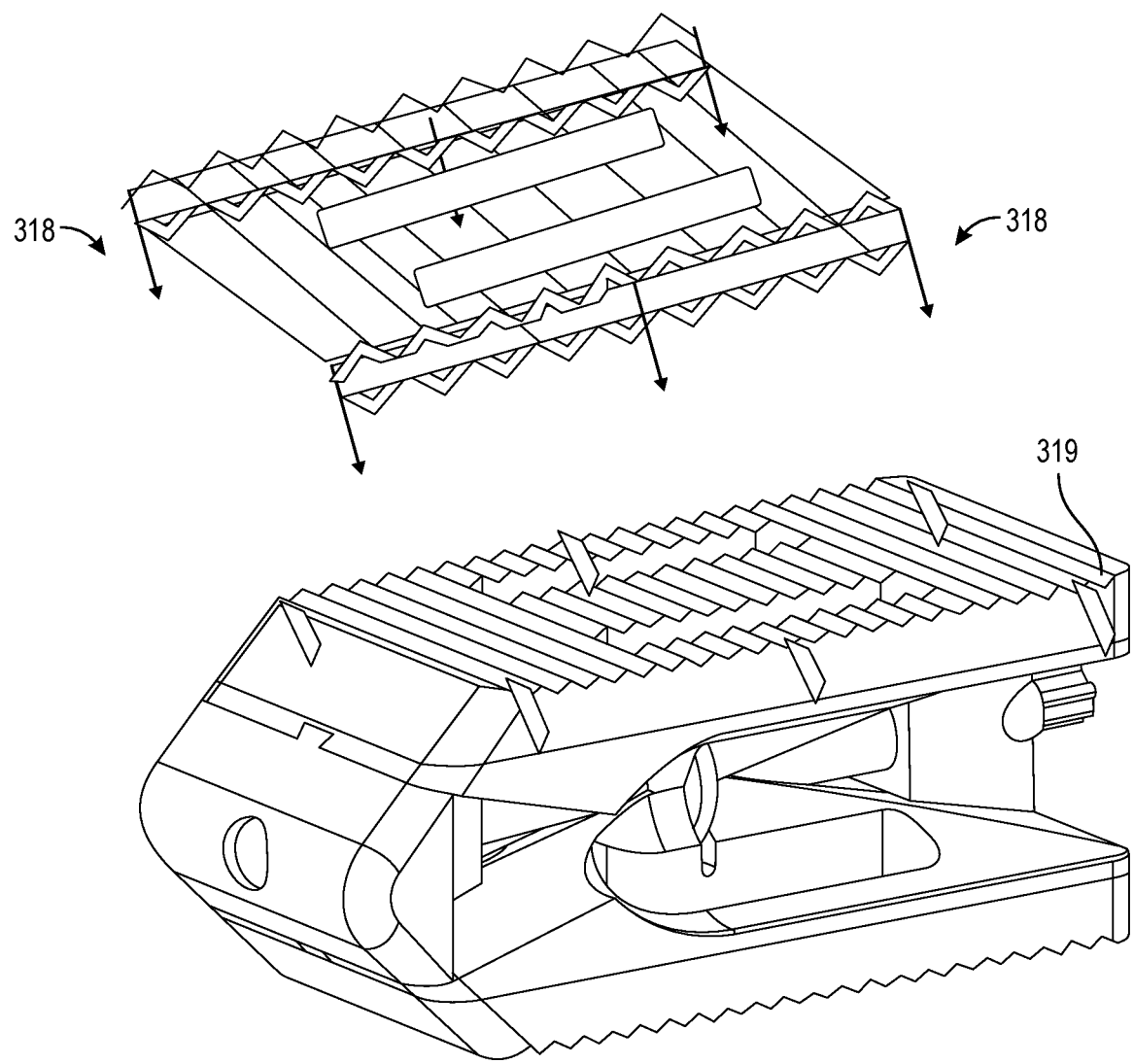
FIG. 40B is a perspective view of the selectively attachable and detachable plate illustrated in FIG. 40A, being selectively attached to a fusion cage suitable for use in conjunction therewith, according to embodiments of the present invention To provide further clarity to the Detailed Description provided herein in the associated drawings, the following list of components and associated numbering are provided as follows.

FIGS. 40A and 40B illustrate another embodiment of a selectively attachable and detachable plate 316 according to the present invention, and a fusion cage 305 associated therewith. In the embodiment of the selectively attachable and detachable plate 316 illustrated in FIGS. 40A and 40B, a "sawtooth" top and/or bottom surface of the plate 316 is adapted to mate with the existing surface of the fusion cage 305. The plate 316 further comprises two grooves, slots, or tracks 317, which may, by way of non-limiting example, be adapted to receive engaging elements of a surgical implant delivery device. As illustrated in FIG. 40B, the plate 316 of this embodiment still further comprises a plurality of tabs 318, which tab receptacles 319 disposed on one or more surfaces of the fusion cage 305 are adapted to receive to provide a more secure attachment of the plate 316 to the cage 305. It is to be expressly understood that the selectively attachable and detachable plate 316 and fusion cage 305 may be provided with or without the grooves, slots, or tracks 317, and/or without the tabs 318 and tab receptacles 319, commensurate with the scope of the invention.

In embodiments of a surgical implant delivery device according to the present invention, the surgical implant delivery device may comprise a cannula and at least one engaging element. The at least one engaging element may comprise a shape-memory material, disposed at least partially within an interior volume of a distal end of the cannula. The at least one engaging element may comprise two components made of shape-memory material, but any number of shape-memory components and/or engaging elements, including one, three, or more, may be suitable for a desired application and is within the scope of the invention. Where there is more than one component made of shape-memory material, the several components may, but need not, be distributed in a rotationally symmetric orientation about the inner surface of the cannula.

The engaging elements of the embodiments of the surgical implant delivery device may selectively engage and disengage corresponding attachment elements of the spinal fusion cage or other surgical implant. Specifically, the engaging elements of the surgical implant delivery device may engage corresponding attachment elements of the surgical implant when the engaging elements are in a first configuration, and disengage from the attachment elements of the surgical implant when the engaging elements are in a second configuration. The engaging elements may be reconfigurable between the first and second configurations and may be reconfigurable, by way of non-limiting example, by actuation of a user-operable trigger of the surgical implant delivery device.

The engaging elements may comprise any suitable shape-memory material, as will be understood by those of ordinary skill in the art, but may preferably be made of a nickel-titanium alloy, also known as Nitinol. Nitinol exhibits various advantageous mechanical properties, including shape memory and superelasticity, and is biocompatible and therefore already widely used in surgical tools and other medical devices.

Engaging elements may be configured such that they extend beyond, and outwardly from, the distal end of the cannula. In embodiments, the engaging elements may comprise a leaf or tab extending outwardly from a longitudinal axis of each shape-memory component, but other engaging elements, as disclosed and described elsewhere herein, may also be suitable for use in the present invention. The engaging elements may, but need not, retract, or be retractable, such that they are completely within the interior volume of the cannula when not engaging a spinal fusion cage or other surgical implant.

The cannula itself will generally be cylindrical, or have a rectangular cross-section, but any shape of the cannula suitable for surgical use may be employed. Often, the cannula will have an inner or outer diameter of about eight millimeters, especially where the surgical implant delivery device is operable to receive and convey bone graft material to a surgical site. Other shapes and dimensions for the cannula and other components of the surgical implant delivery device may be employed as suitable for a particular application. Particularly, the cannula may be curved or angled such that the distal end, or a portion of the distal end, of the cannula is offset from or lies in a different plane than the proximal end, or a portion of the proximal end. The cannula will frequently be made of a biocompatible metal or metal alloy, and may especially comprise a ferrous material, but any material suitable for use in surgical tools and other medical devices may be employed.

The relative orientations and configurations of the cannula and engaging portion may take any suitable form for a desired application, but in general, the shape-memory component of the engaging portion will be disposed at least partially within an interior volume of a distal end of the cannula, and may, but need not, reside within a groove, slot, or track in an interior surface of the cannula when not engaging a spinal fusion cage or other surgical implant. In many cases it may be desirable for the shape-memory components to extend beyond the distal end of the cannula, while in other cases the distal end of the shape-memory components and the distal end of the cannula may be coterminous or in close proximity. In embodiments in which the surgical implant delivery device is operable to receive and convey bone graft material, it is generally desirable for the shape-memory components not to impede an opening in the distal end of the cannula, and in these embodiments the flexible strips may terminate proximally (closer to a user) relative to the opening in the distal end of the cannula.

It is to be expressly understood that the components configured to engage the fusion cage 60 depicted in FIGS. 18-27 and the components configured to engage the fusion cage 60 depicted in FIGS. 28-36, as well as other components disclosed and described herein, may be provided separately or in combination. By way of non-limiting example, engaging elements comprising a flexible and/or shape-memory material that selectively engage or disengage a surgical implant, as described in this section; the installer/impactor system, as illustrated in FIGS. 18-27; and/or one or more features of the surgical implant delivery device illustrated in FIGS. 28-36, may be provided as separate embodiments of the invention, or may be provided in a single device, for example to provide redundancy to ensure that the spinal fusion cage or other surgical implant does not accidentally or prematurely detach from the device. Any or all of the above embodiments may be provided in conjunction with one or more features of the expandable spinal fusion cage and/or selectively attachable and detachable plate as described above and as illustrated in FIGS. 38-40.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g. the use of disposable components comprising some or all of the apparatus described herein, as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. An intervertebral bone graft delivery system comprising:
    a fusion cage configured to receive, allow for flow therethrough, and contain bone graft therein, the fusion cage being expandable, and having at least one opening therethrough and an expansion screw adapted to expand the fusion cage;
    an expansion tool complex having a distal end configured to rotatably engage the expansion screw, whereby the fusion cage is moveable from an unexpanded state to an expanded state; and
    an insertion instrument configured to reversibly attach to the fusion cage, the insertion instrument including a slidable rectangular shaft, a handle generally orthogonally oriented relative to the slidable rectangular shaft, and a trigger operably engaging the handle and configured to be squeezed against the handle in a first direction and to cause the slidable rectangular shaft to move in a second direction that is opposite to the first direction.

2. The system of claim 1, further comprising a funnel configured to removably engage a proximate end of the slidable rectangular shaft, and to receive bone graft material therein.

3. The system of claim 1, wherein the expansion tool complex includes a ratcheting screwdriver handle, a quick connect device, and a screwdriver shaft configured to rotatably engage the expansion screw of the fusion cage.

4. The system of claim 1, further comprising an insertion plunger configured as an impaction device for driving the fusion cage into a patient's disk space.

5. The system of claim 1, wherein the slidable rectangular shaft has a window and expandable tabs configured to be compressed through the window and inserted into the at least one opening of the fusion cage to attach the fusion cage to the insertion tool.

6. The system of claim 1, further comprising a locking mechanism operably attached to the slidable rectangular shaft to enable sliding and tightening of the rectangular shaft against the fusion cage.

7. An intervertebral bone graft delivery system comprising:
    an expandable fusion cage configured to receive, allow for flow therethrough, and contain bone graft therein, the expandable fusion cage having at least one opening and an expansion screw adapted to expand the fusion cage;
    an expansion tool complex having a distal end configured to rotatably engage the expansion screw, whereby the fusion cage is moveable from an unexpanded state to an expanded state; and
    an insertion instrument configured to reversibly attach to the fusion cage, the insertion instrument including:
        a slidable rectangular shaft having a window and expandable tabs configured to be compressed through the window and inserted into the at least one opening of the fusion cage to attach the fusion cage to the insertion tool;
        a handle generally orthogonally oriented relative to the slidable rectangular shaft;
        a trigger operably engaging the handle and configured to be squeezed against the handle in a first direction and to cause the slidable rectangular shaft to move in a second direction that is opposite to the first direction; and
        a locking mechanism operably attached to the slidable rectangular shaft to enable sliding and tightening of the rectangular shaft against the fusion cage.

8. The system of claim 7, further comprising a funnel configured to removably engage a proximate end of the slidable rectangular shaft, and to receive bone graft material therein.

9. The system of claim 7, wherein the expansion tool complex includes a ratcheting screwdriver handle, a quick connect device, and a screwdriver shaft configured to rotatably engage the expansion screw of the fusion cage.

* * * * *